United States Patent
Teuber et al.

(10) Patent No.: US 6,936,613 B2
(45) Date of Patent: Aug. 30, 2005

(54) BENZIMIDAZOLE DERIVATIVES AND PHARMACEUTICAL COMPOSITIONS COMPRISING THESE COMPOUNDS

(75) Inventors: Lene Teuber, Vaerlose (DK); Frank Watjen, Farum (DK)

(73) Assignee: Neurosearch A/S, Ballerup (DK)

( * ) Notice: Subject to any disclaimer, the term of this patent is extended or adjusted under 35 U.S.C. 154(b) by 65 days.

(21) Appl. No.: 10/618,727

(22) Filed: Jul. 15, 2003

(65) Prior Publication Data

US 2004/0097570 A1 May 20, 2004

Related U.S. Application Data

(62) Division of application No. 10/012,490, filed on Dec. 12, 2001, now Pat. No. 6,649,609.

(51) Int. Cl.$^7$ .................... A61K 31/495; A61K 31/415; C07D 403/00; C07D 235/24
(52) U.S. Cl. .................. 514/252.19; 514/393; 544/370; 548/309.4
(58) Field of Search ...................... 548/309.4; 544/370; 514/393, 252.19

(56) References Cited

U.S. PATENT DOCUMENTS

| | | | | |
|---|---|---|---|---|
| 3,951,920 A | * | 4/1976 | Senoo et al. ................. 210/654 |
| 5,149,814 A | * | 9/1992 | Cooper et al. .............. 546/118 |
| 5,294,631 A | * | 3/1994 | Franz et al. ................. 514/381 |
| 5,401,738 A | * | 3/1995 | Mederski et al. ........ 514/222.5 |
| 5,554,630 A | | 9/1996 | Teuber et al. |
| 5,554,632 A | | 9/1996 | Teuber et al. |
| 5,693,633 A | * | 12/1997 | Boyd et al. ............. 514/210.18 |
| 5,864,043 A | * | 1/1999 | Narr et al. ................ 548/307.1 |
| 5,922,725 A | | 7/1999 | Teuber et al. |
| 5,977,101 A | * | 11/1999 | Ali et al. ..................... 514/221 |
| 6,034,114 A | * | 3/2000 | Hill ............................. 514/381 |
| 6,124,463 A | * | 9/2000 | Beck et al. .............. 546/273.4 |
| 6,503,925 B1 | * | 1/2003 | Teuber et al. ............... 514/307 |
| 6,649,609 B2 | * | 11/2003 | Teuber et al. ............. 514/228.2 |
| 6,686,384 B2 | * | 2/2004 | Hofmeister et al. ........ 514/398 |
| 6,710,044 B2 | * | 3/2004 | Teuber et al. ............ 514/235.8 |

FOREIGN PATENT DOCUMENTS

| | | |
|---|---|---|
| EP | 0 616 807 A1 | 9/1994 |
| WO | 96/33191 A1 | 10/1996 |
| WO | 96/33192 A1 | 10/1996 |
| WO | 96/33194 A1 | 10/1996 |
| WO | 98/17651 A1 | 4/1998 |
| WO | 98/34923 A1 | 8/1998 |
| WO | 99/19323 A1 | 4/1999 |

OTHER PUBLICATIONS

Wiklund et al., The New England Journal of Medicine, vol. 337, No. 16, pp. 1132–1141 (1997).

* cited by examiner

*Primary Examiner*—Deborah C. Lambkin
(74) *Attorney, Agent, or Firm*—Birch, Stewart, Kilasch & Birch, LLP

(57) ABSTRACT

The present invention relates to novel benzimidazole derivatives, pharmaceutical compositions containing these compounds, and methods of treatment therewith. The compounds of the invention are useful in the treatment of central nervous system diseases and disorders, which are responsive to modulation of the GABA$^A$ receptor complex, and in particular for inducing and maintaining anesthesia, sedation and muscle relaxation, as well as for combating febrile convulsions in children. The compounds of the invention may also be used by veterinarians.

10 Claims, No Drawings

BENZIMIDAZOLE DERIVATIVES AND PHARMACEUTICAL COMPOSITIONS COMPRISING THESE COMPOUNDS

This application is a division of Ser. No. 10/012,490 filed Dec. 12, 2001, now U.S. Pat. No. 6,649,609.

TECHNICAL FIELD

The present invention relates to novel benzimidazole derivatives, pharmaceutical compositions containing these compounds, and methods of treatment therewith.

The compounds of the invention are useful in the treatment of central nervous system diseases and disorders, which are responsive to modulation of the $GABA_A$ receptor complex, and in particular for inducing and maintaining anaesthesia, sedation and muscle relaxation, as well as for combating febrile convulsions in children.

The compounds of the invention may also be used by veterinarians.

BACKGROUND ART

Agents that bind or interact with the modulatory sites on the $GABA_A$ receptor complex, such as for example the benzodiazepine receptor, can have either enhancing effect on the action of GABA, i.e. a positive modulatory effect of the receptor (agonists, partial agonists), an attenuating effect on the action of GABA, i.e. negative modulation of the receptor (inverse agonists, partial inverse agonists), or they can block the effect of both agonists and inverse agonists (antagonists or ligands without intrinsic activity).

Agonists generally produce muscle relaxant, hypnotic, sedative, anxiolytic, and/or anticonvulsant effects, while inverse agonists produce pro-convulsive, anti-inebriant or anxiogenic effects. Compounds with anxiolytic effects, but with or without reduced muscle relaxant, hypnotic and sedative effects, are characterised as partial agonists. Partial inverse agonists are considered to be useful as cognition enhancers.

Full agonists of the benzodiazepine receptor are considered useful as anaesthetics. However, many drugs presently available as anaesthetics, and specially pre-anaesthetics, give rise to hang-over effects as well as long awakening times, wherein careful monitoring of the patient is necessary. Anaesthetics with a long half-life may also impose difficulties during incidents of overdosing i.e. prolonged respiratory depression. Furthermore, some currently used drugs cannot be used for anaesthetising children as deaths have been reported in children after prolonged use of Propofol. Some anaesthetics are gasses which inherently possesses a contamination problem for the medical staff.

A well known anaesthetic, Propofol, is administered as a mixture of soybean oil, glycerol and purified egg phosphatide, which mixture nourish bacterial growth. Administration of bacterially contaminated Propofol has been reported to cause sepsis and death [Wiklund et al; *The New England Journal of Medicine* 1997 337 (16) 1132–1141]. Further, compounds with a long in vivo half-life will give problems with accumulation during and after prolonged treatment e.g. when administered to patients constrained to a respirator. Short half-lives wherein the compounds are metabolised to inactive metabolites allow for a predictable correlation of dose and duration of pharmacological effect.

Ideally the anaesthestising effect should be observed shortly after a bolus injection or infusion of the compound. A rapid onset of action minimises the period of anxiety and uneasiness experienced by patients going into surgery.

Patients suffering from severe and continuous epileptic attacks presently treated with large amounts of sedatives, e.g. benzodiazepines, will benefit from shorter acting compounds with no hang-over or long lasting sedating effect.

As the preferred route of administration is by intravenous injection or infusion, the anaesthestising compounds should preferably be water soluble.

EP 616807 describes benzimidazole compounds for use as benzodiazepine receptor ligands.

WO 96/33194, WO 96/33191 and WO 96/33192 describe benzimidazole compounds having affinity for the GABA receptor complex.

WO 98/34923 describes phenylbenzimidazole derivatives as ligands for the GABA receptor complex.

WO 98/17651 describes benzimidazole compounds for use as e.g. anaesthetics. However, the presently disclosed compounds are superior to the compounds previously described.

SUMMARY OF THE INVENTION

It is an object of the invention to provide novel compounds useful as anaesthetics and/or pre-anaesthetics, sedatives, muscle relaxants, and for the treatment of febrile convulsions in children, status epilepticus, for use to patients constrained to a respirator as well as for veterinarian uses.

In its first aspect, the invention provides a benzimidazole derivative represented by the general Formula I,

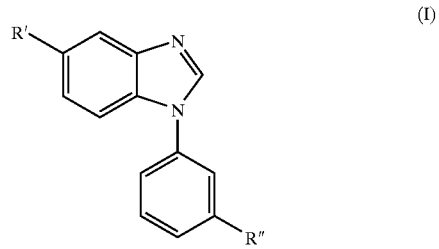

(I)

or a pharmaceutically acceptable salt thereof, wherein,

R' represents a group of the formula $-(alk)_q-R^1$, wherein (alk) represents alkyl, alkenyl or alkynyl, q is 0 or 1, $R^1$ represents a group of the formula $-CO_2R^2$, wherein $R^2$ represents hydrogen, alkyl, hydroxy-alkyl, alkoxy-alkyl, thioalkoxy-alkyl, alkyl-"Heterocycle", or -alkyl-$NR^3R^4$, wherein "Heterocycle" represents a mono- or polycyclic heterocyclic group, which heterocyclic group is optionally substituted one or more times with substituents selected from the group consisting of halogen, alkyl, hydroxy, oxo, cyano, hydroxy-alkyl, alkoxy-alkyl, carboxyl and acyl, and a group of the formula $-(alkyl)_p-CN$, $-(alkyl)_p$-aryl, $-(alkyl)_p$-"Heterocycle", $-(alkyl)_p-CO_2$-"Heterocycle" or $-(alkyl-CO_2)_s-(alkyl)_t-COR^5$, in which formulas p, s and t independently of each another is 0 or 1, "Heterocycle" represents a mono- or polycyclic heterocyclic group, which heterocyclic group is optionally substituted one or more times with substituents selected from the group consisting of halogen, alkyl, hydroxy, oxo, cyano, hydroxy-alkyl, alkoxy-alkyl, carboxyl and acyl, $R^5$ represents hydroxy, alkoxy, hydroxy-alkoxy, alkoxy-alkoxy, thioalkoxy-alkoxy, or a group of the formula —$NR^6R^7$ or —O-alkyl-$NR^6R^7$, in which formulas $R^6$ and $R^7$ independently of each another represent hydrogen, alkyl, cycloalkyl or a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl, or $R^6$ and $R^7$ together with the nitrogen to which they are attached form a mono- or polycyclic heterocyclic group, which heterocyclic group may be substituted one or more times with substituents selected from the group consisting of halogen, alkyl, hydroxy, oxo, hydroxy-alkyl, alkoxy-alkyl, carboxyl and acyl; and $R^3$ and $R^4$ independently of each another represent hydrogen, alkyl or cycloalkyl, or $R^3$ and $R^4$ together with the nitrogen to which they are attached form a mono- or poly-cyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl; or $R^1$ represents a group of the formula

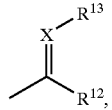

wherein

X represents N or CH, $R^{12}$ represents hydrogen, alkyl, alkoxy or hydroxy-alkyl, and $R^{13}$ represents hydrogen, hydroxy, alkyl, alkoxy or hydroxy-alkyl; or $R^1$ represents a mono- or polycyclic heterocyclic group, which heterocyclic group is optionally substituted one or more times with substituents selected from the group consisting of alkyl, hydroxy-alkyl, alkoxy-alkyl, carboxyl, and acyl, and a group of the formula -(alkyl)$_p$-aryl, -(alkyl)$_p$-"Heterocycle", -(alkyl)$_p$—CN or -(alkyl-$CO_2$)$_s$-(alkyl)$_t$-$COR^5$, in which formulas p, s and t independently of each another is 0 or 1, "Heterocycle" represents a mono- or polycyclic heterocyclic group, which heterocyclic group is optionally substituted one or more times with substituents selected from the group consisting of halogen, alkyl, hydroxy, oxo, cyano, hydroxy-alkyl, alkoxy-alkyl, carboxyl and acyl, $R^5$ represents hydroxy, alkoxy, hydroxy-alkoxy, alkoxy-alkoxy, thioalkoxy-alkoxy, or a group of the formula —$NR^6R^7$ or —O-alkyl-$NR^6R^7$, in which formulas $R^6$ and $R^7$ independently of each another represent hydrogen, alkyl, cycloalkyl or a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl, or $R^6$ and $R^7$ together with the nitrogen to which they are attached form a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl; and $R"$ represents -(alkyl)$_o$-"Heterocycle" or -(alkyl)$_o$-$CO_2$-(alkyl)$_u$-"Heterocycle", wherein o and u independently of each another is 0 or 1, and "Heterocycle" represents a mono- or polycyclic heterocyclic group, which heterocyclic group is optionally substituted one or more times with substituents selected from the group consisting of halogen, alkyl, hydroxy, oxo, cyano, hydroxy-alkyl, alkoxy-alkyl, carboxyl, and acyl, and a group of the formula -(alkyl)$_p$-CN, -(alkyl)$_p$-aryl, -(alkyl)$_p$-aralkyl, -(alkyl)$_p$-O-aryl, -(alkyl)$_p$-O-aralkyl, -(alkyl)$_p$-$CO_2$-aryl, -(alkyl)$_p$-$CO_2$-aralkyl, -(alkyl)$_p$-"Heterocycle", -(alkyl)$_p$-$CO_2$-"Heterocycle" or -(alkyl-$CO_2$)$_s$-(alkyl)$_t$-$COR^5$, in which formulas p, s and t independently of each another is 0 or 1, "Heterocycle" represents a mono- or polycyclic heterocyclic group, which heterocyclic group is optionally substituted one or more times with substituents selected from the group consisting of halogen, alkyl, hydroxy, oxo, cyano, hydroxy-alkyl, alkoxy-alkyl, carboxyl and acyl, $R^5$ represents hydrogen, hydroxy, alkyl, alkoxy, hydroxy-alkyl, hydroxy-alkoxy, alkoxy-alkyl, alkoxy-alkoxy, thioalkoxy-alkyl, thioalkoxy-alkoxy, or a group of the formula —$NR^6R^7$ or —O-alkyl-$NR^6R^7$, in which formulas $R^6$ and $R^7$ independently of each another represent hydrogen, alkyl, cycloalkyl or a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl, or $R^6$ and $R^7$ together with the nitrogen to which they are attached form a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl; or $R"$ represents -(alkyl)$_m$-$CO_2R^8$, wherein m is 0 or 1, and $R^8$ represents hydrogen, alkyl, hydroxy-alkyl, alkoxy-alkyl, thioalkoxy-alkyl, or a group of the formula -(alkyl)$_p$-$NR^9R^{10}$, wherein p is 0 or 1, and $R^9$ and $R^{10}$ independently of each another represent hydrogen, alkyl, cycloalkyl, or a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl, or $R^9$ and $R^{10}$ together with the nitrogen to which they are attached form a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl.

In its second aspect, the invention provides a pharmaceutical composition containing a therapeutically effective amount of a benzimidazole derivative according to the invention, or a pharmaceutically acceptable addition salt thereof, together with at least one pharmaceutically acceptable carrier, excipient or diluent.

In its third aspect, the invention provides a use of a benzimidazole derivative according to the invention for the manufacture of a medicament for the treatment, prevention or alleviation of a disease or a disorder or a condition of a mammal, including a human, which disease, disorder or condition is responsive to modulation of the GABA receptor complex.

In its fourth aspect, the invention provides a method for treatment, prevention or alleviation of a disease or a disorder or a condition of a living animal body, including a human, which disorder, disease or condition is responsive to modulation of the GABA receptor complex, which method comprises the step of administering to such a living animal body in need thereof a therapeutically effective amount of a benzimidazole derivative according to the invention.

Other objects of the invention will be apparent to the person skilled in the art from the following detailed description and the working examples.

DETAILED DISCLOSURE OF THE INVENTION
Benzimidazole Derivatives

In its first aspect the invention provides novel benzimidazole derivatives. The benzimidazole derivatives of the invention are represented by the general Formula I,

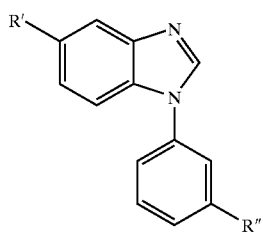

(I)

or a pharmaceutically acceptable salt thereof,
wherein,
R' represents a group of the formula -(alk)$_q$-R$^1$,
wherein
(alk) represents alkyl, alkenyl or alkynyl,
q is 0 or 1,
R$^1$ represents a group of the formula —CO$_2$R$^2$, wherein
R$^2$ represents hydrogen, alkyl, hydroxy-alkyl, alkoxy-alkyl, thioalkoxy-alkyl, alkyl-"Heterocycle", or -alkyl-NR$^3$R$^4$,
wherein
"Heterocycle" represents a mono- or polycyclic heterocyclic group, which heterocyclic group is optionally substituted one or more times with substituents selected from the group consisting of halogen, alkyl, hydroxy, oxo, cyano, hydroxy-alkyl, alkoxy-alkyl, carboxyl and acyl, and a group of the formula -(alkyl)$_p$-CN, -(alkyl)$_p$-aryl, -(alkyl)$_p$-"Heterocycle", -(alkyl)$_p$-CO$_2$-"Heterocycle" or -(alkyl-CO$_2$)$_s$-(alkyl)$_t$-COR$^5$,
in which formulas
p, s and t independently of each another is 0 or 1,
"Heterocycle" represents a mono- or polycyclic heterocyclic group, which heterocyclic group is optionally substituted one or more times with substituents selected from the group consisting of halogen, alkyl, hydroxy, oxo, cyano, hydroxy-alkyl, alkoxy-alkyl, carboxyl and acyl,
R$^5$ represents hydroxy, alkoxy, hydroxy-alkoxy, alkoxy-alkoxy, thioalkoxy-alkoxy, or a group of the formula —NR$^6$R$^7$ or —O-alkyl-NR$^6$R$^7$,
in which formulas
R$^6$ and R$^7$ independently of each another represent hydrogen, alkyl, cycloalkyl or a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl, or
R$^6$ and R$^7$ together with the nitrogen to which they are attached form a mono- or polycyclic heterocyclic group, which heterocyclic group may be substituted one or more times with substituents selected from the group consisting of halogen, alkyl, hydroxy, oxo, hydroxy-alkyl, alkoxy-alkyl, carboxyl and acyl; and
R$^3$ and R$^4$ independently of each another represent hydrogen, alkyl or cycloalkyl, or
R$^3$ and R$^4$ together with the nitrogen to which they are attached form a mono- or poly-cyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl; or
R$^1$ represents a group of the formula

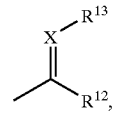

wherein
X represents N or CH,
R$^{12}$ represents hydrogen, alkyl, alkoxy or hydroxy-alkyl, and
R$^{13}$ represents hydrogen, hydroxy, alkyl, alkoxy or hydroxy-alkyl; or
R$^1$ represents a mono- or polycyclic heterocyclic group, which heterocyclic group is optionally substituted one or more times with substituents selected from the group consisting of alkyl, hydroxy-alkyl, alkoxy-alkyl, carboxyl, and acyl, and a group of the formula -(alkyl)$_p$-aryl, -(alkyl)$_p$-"Heterocycle", -(alkyl)$_p$-CN or -(alkyl-CO$_2$)$_s$-(alkyl)$_t$-COR$^5$,
in which formulas
p, s and t independently of each another is 0 or 1,
"Heterocycle" represents a mono- or polycyclic heterocyclic group, which heterocyclic group is optionally substituted one or more times with substituents selected from the group consisting of halogen, alkyl, hydroxy, oxo, cyano, hydroxy-alkyl, alkoxy-alkyl, carboxyl and acyl,
R$^5$ represents hydroxy, alkoxy, hydroxy-alkoxy, alkoxy-alkoxy, thioalkoxy-alkoxy, or a group of the formula —NR$^6$R$^7$ or —O-alkyl-NR$^6$R$^7$,
in which formulas
R$^6$ and R$^7$ independently of each another represent hydrogen, alkyl, cycloalkyl or a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl, or
R$^6$ and R$^7$ together with the nitrogen to which they are attached form a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl; and
R" represents -(alkyl)$_o$-"Heterocycle" or -(alkyl)$_o$-CO$_2$—(alkyl)$_o$-"Heterocycle", wherein o and u independently of each another is 0 or 1, and "Heterocycle" represents a mono- or polycyclic heterocyclic group, which heterocyclic group is optionally substituted one or more times with substituents selected from the group consisting of halogen, alkyl, hydroxy, oxo, cyano, hydroxy-alkyl, alkoxy-alkyl, carboxyl, and acyl, and a group of the formula -(alkyl)$_p$-CN, -(alkyl)$_p$-aryl, -(alkyl)$_p$-aralkyl, -(alkyl)$_p$-O-aryl, -(alkyl)$_p$-O-aralkyl, -(alkyl)$_p$-CO$_2$-aryl, -(alkyl)$_p$-CO$_2$-aralkyl, -(alkyl)$_p$-"Heterocycle", -(alkyl)$_p$-CO$_2$-"Heterocycle" or -(alkyl-CO$_2$)$_s$-(alkyl)$_t$-COR$^5$, in which formulas p, s and t independently of each another is 0 or 1, "Heterocycle" represents a mono- or polycyclic heterocyclic group, which heterocyclic group is optionally substituted one or more times with substituents selected from the group consisting of halogen, alkyl, hydroxy, oxo, cyano, hydroxy-alkyl, alkoxy-alkyl, carboxyl and acyl, R$^5$ represents hydrogen, hydroxy, alkyl, alkoxy, hydroxy-alkyl, hydroxy-alkoxy, alkoxy-alkyl, alkoxy-alkoxy, thioalkoxy-alkyl, thioalkoxy-alkoxy, or a group of the formula —NR$^6$R$^7$ or —O-alkyl-NR$^6$R$^7$, in which formulas R$^6$ and R$^7$ independently of each another represent hydrogen, alkyl, cycloalkyl or a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl, or R$^6$ and R$^7$ together with the nitrogen to which they are attached form a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl; or R" represents -(alkyl)$_m$-CO$_2$R$^8$, wherein m is 0 or 1, and R$^8$ represents hydrogen, alkyl, hydroxy-alkyl, alkoxy-alkyl, thioalkoxy-alkyl, or a group of the formula -(alkyl)$_p$-NR$^9$R$^{10}$, wherein p is 0 or 1, and R$^9$ and R$^{10}$ independently of each another represent hydrogen, alkyl, cycloalkyl, or a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl, or R$^9$ and R$^{10}$ together with the nitrogen to which they are attached form a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl.

In a preferred embodiment the benzimidazole derivative of the invention is represented by Formula I, wherein R" represents
2-(4-acetylpiperazin-1-yl)-ethoxy-carbonyl;
pyridin-2-yl-methoxy-carbonyl;
1-Methyl-2-pyrrolidyl-methoxy-carbonyl; or
3,5-dimethyl-1-piperazinyl-ethoxy-carbonyl.

In a most preferred embodiment, the benzimidazole derivative is
2-(1-Acetyl-4-piperazinyl)-ethyl 3-(5-(3-furanyl)-1-benzimidazolyl)-benzoate;
1-Methyl-2-pyrrolidylmethyl 3-(5-(3-furanyl)-1-benzimidazolyl)-benzoate;
or a pharmaceutically acceptable salt thereof.

In another preferred embodiment the benzimidazole derivative of the invention is a compound of Formula I, wherein R$^1$ represents a group of the formula —CO$_2$R$^2$, wherein R$^2$ represents alkyl, hydroxy-alkyl, alkoxy-alkyl, thioalkoxy-alkyl, alkyl-N(alkyl)$_2$; or R$^1$ represents a group of the formula

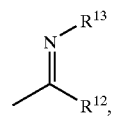

wherein

R$^{12}$ represents alkyl, and

R$^{13}$ represents hydroxy, or alkoxy; or

R$^1$ represents a furanyl group, a pyrazolyl group, an isoxazolyl group, an oxazolyl group, an oxadiazolyl group.

In a more preferred embodiment

R$^1$ represents a group of the formula —COOH, —CO$_2$—CH$_3$, —CO$_2$—C$_2$H$_5$, —CO$_2$—CH$_2$—CH(OH), —CO$_2$(CH$_2$)$_2$OCH$_3$, —CO$_2$(CH$_2$)$_2$SCH$_3$, —CO$_2$(CH$_2$)$_2$SC$_2$H$_5$, or —CO$_2$(CH$_2$)$_2$N(CH$_3$)$_2$; or R$^1$ represents a group of the formula

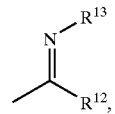

wherein

R$^{12}$ represents methyl or ethyl, and

R$^{13}$ represents hydroxy, methoxy or ethoxy; or

R$^1$ represents a 2- or 3-furanyl group.

In a most preferred embodiment, the benzimidazole derivative is
2-(3,5-dimethyl-1-piperazinyl)-ethyl 3-(5-acetylbenzimidazol-1-yl)-benzoate oxime; or
2-(2-pyridyl)-methyl 3-(5-acetylbenzimidazol-1-yl)-benzoate oxime;
or a pharmaceutically acceptable salt thereof.

In another preferred embodiment the benzimidazole derivative of the invention is represented by Formula I, wherein R" represents a group of the formula -(alkyl)$_o$-"Heterocycle", wherein o is 0 or 1, and "Heterocycle" represents a furanyl group, a 2H-furanyl group, a 4H-furanyl group, a thienyl group, a pyrrolyl group, a 2H-pyrrolyl (pyrrolinyl) group, a 4H-pyrrolyl (pyrrolidinyl) group, an imidazolyl group, an oxazolyl group, a 2H-oxazolyl (oxazolinyl) group, a 4H-oxazolyl (oxazolidinyl) group, an isoxazolyl group, a 2H-isoxazolyl (isoxazolinyl) group, a 4H-isoxazolyl (isoxazolidinyl) group, an oxadiazolyl group, a 2H-oxadiazolyl (oxadiazolinyl) group, a 4H-oxadiazolyl (oxadiazolidinyl) group, a morpholinyl group, a thiomorpholinyl group, a pyridinyl group, a piperidinyl group, a piperazine group, a homopiperazine group or a tetrazolyl group, which heterocyclic groups may be substituted one or more times with substituents selected from the group consisting of halogen, alkyl, oxo, acyl, alkyl-CO$_2$H, alkyl-CO$_2$-alkyl-(alkyl)$_p$-CO$_2$-aryl, -(alkyl)$_p$-CO$_2$-aralkyl and alkyl-CO$_2$-alkyl-CONR$^6$R$^7$, wherein R$^6$ and R$^7$ independently of each another represent hydrogen or alkyl.

In a more preferred embodiment,

"Heterocycle" represents a pyrrolidin-1-yl; a piperazin-1-yl; a homopiperazin-1-yl; an imidazol-1-yl; a pyridin-4-yl; a 4H-pyridin-4-yl, in particular a 1,2,5,6-tetrahydro-pyridin-4-yl; a piperidin4-yl; a 2H-isoxazol-3-yl, in particular a 4,5-dihydro-isoxazol-3-yl.

In a further preferred embodiment the benzimidazole derivative of the invention is represented by Formula I, wherein R"
4-ethoxycarbonyl-1-imidazolyl;
4-methoxycarbonyl-1-imidazolyl;
5-((N,N-Diethylcarbamoyl)-methoxy-carbonyl-methyl)-4,5-dihydroisoxazol-3-yl;
5-((N,N-Dimethylcarbamoyl)-methoxy-carbonyl-methyl)-4,5-dihydroisoxazol-3-yl;
1-imidazolylmethyl;
4-(1-methyl-5-tetrazolyl)-methyl-1-piperazinyl;
1-ethyl-1,2,5,6-tetrahydropyridin-4-yl;
4-(2-oxazolidinone-5-yl)-methyl)1-piperazinyl;
4-(5-methyloxadiazol-3-yl)-methyl)1-piperazinyl;
4-(3,5-dimethylisoxazol-4-yl)-methyl)1-piperazinyl;
4-(2-oxo-tetrahydrofuran-3-yl)-1-piperazinyl;
4-(2-chloro-5-thienyl)-methyl-1-piperazinyl; or
(1-methyl-2-pyrrolidyl)-methyl-carbonyl.

In a most preferred embodiment the benzimidazole derivative of the invention is
2-Methoxyethyl 1-(3-(4-methoxycarbonyl-1-imidazolyl)-phenyl)-benzimidazole-5-carboxylate;
(N,N-Diethylcarbamoyl)-methyl 2-(3-[3-(5-ethoxycarbonyl-1-benzimidazolyl)-phenyl]-4,5-dihydroxyisoxazol-5-yl)-acetate;
Methyl 1-(3-(1-imidazolylmethyl)-phenyl)-benzimidazole-5-carboxylate;
2-(Methylthio)-ethyl 1-(3-(1-imidazolylmethyl)-phenyl)-benzimidazole-5-carboxylate;
2-Methoxyethyl 1-(3-(4-(1-methyl-5-tetrazolyl)methyl-1-piperazinyl)-phenyl)-benzimidazole-5-carboxylate;
2-Methoxyethyl 1-(3-(1-ethyl-1,2,5,6-tetrahydropyridin-4-yl)-phenyl)-benzimidazole-5-carboxylate;
2-Methoxyethyl 1-(3-(4-(2-oxazolidinone-5-yl)-methyl)1-piperazinyl)-phenyl)-benzimidazole-5-carboxylate;
2-Methoxyethyl 1-(3-(4-(5-methyloxadiazol-3-yl)-methyl)1-piperazinyl)-phenyl)-benzimidazole-5-carboxylate;
2-Methoxyethyl 1-(3-(4-(3,5-dimethylisoxazol-4-yl)methyl)1-piperazinyl)-phenyl)-benzimidazole-5-carboxylate;
2-Methoxyethyl 1-(3-(4-(2-oxo-tetrahydrofuran-3-yl)-1-piperazinyl)-phenyl)-benzimidazole-5-carboxylate;
2-Methoxyethyl 1-(3-(4-(2-chloro-5-thienyl)-methyl-1-piperazinyl)-phenyl)-benzimidazole-5-carboxylate;
5-(3-Furanyl)-1-(3-(4-methoxycarbonyl-1-imidazolyl)-phenyl)-benzimidazole; or
N,N-Diethylcarbamoylmethyl 2-(3-(3-(5-(3-furanyl)-1-benzimidazolyl)-phenyl)-4,5-dihydroisoxazole-5-yl)-acetate;
or a pharmaceutically acceptable salt thereof.

In another preferred embodiment the benzimidazole derivative of the invention is represented by Formula I wherein
R" represents a group of the formula —CO$_2$-(alkyl)$_o$-"Heterocycle", wherein
o is 0 or 1, and
"Heterocycle" represents a pyrrolyl group, a 2H-pyrrolyl (pyrrolinyl) group, a 4H-pyrrolyl (pyrrolidinyl) group, an imidazolyl group, an oxazolyl group, an isoxazolyl group, a 2H-isoxazolyl (isoxazolinyl) group, a 4H-isoxazolyl (isoxazolidinyl) group, an oxadiazolyl group, a pyridyl group, a piperidinyl group, a piperazine group or a homopiperazine group, which heterocyclic groups may be substituted one or more times with substituents selected from the group consisting of alkyl, acyl, alkyl-CO$_2$H, alkyl-CO$_2$-alkyl and alkyl-CO$_2$-alkyl-CONR$^6$R$^7$, wherein
R$^6$ and R$^7$ independently of each another represent hydrogen or alkyl.

In a more preferred embodiment the benzimidazole derivative of the invention is represented by Formula I, wherein
R" represents a group of the formula

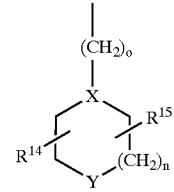

in which formula
o is 0 or 1,
n is 0, 1 or 2,
X represents N or CH,
Y represents O, NR$^{11}$ or CHR$^{11}$,
wherein R$^{11}$ represents hydrogen, alkyl, hydroxy-alkyl, alkoxy-alkyl, carboxyl or acyl, or a group of the formula -(alkyl)$_p$-CN, -(alkyl)$_p$-aryl, -(alkyl)$_p$-O-aryl, -(alkyl)$_p$-O-aralkyl, -(alkyl)$_p$-"Heterocycle", -(alkyl)$_p$-CO$_2$-"Heterocycle" or -(alkyl-CO$_2$)$_s$-(alkyl)$_t$-COR$^5$,
wherein
p, s and t independently of each another is 0 or 1,
"Heterocycle" represents a mono- or polycyclic heterocyclic group, which heterocyclic group is optionally substituted one or more times with substituents selected from the group consisting of halogen, alkyl, hydroxy, oxo, cyano, hydroxy-alkyl, alkoxy-alkyl, carboxyl and acyl,
R$^5$ represents hydroxy, alkoxy, hydroxy-alkoxy, alkoxy-alkoxy, thioalkoxy-alkoxy, aryl or aralkyl, or a group of the formula —NR$^6$R$^7$ or —O-alkyl-NR$^6$R$^7$, in which formulas
R$^6$ and R$^7$ independently of each another represents hydrogen, alkyl, cycloalkyl or a mono- or polycyclic heterocyclic group, which heterocyclic group is optionally substituted one or more times with substituents selected from the group consisting of alkyl, and acyl, or
R$^6$ and R$^7$ together with the nitrogen to which they are attached form a mono- or polycyclic heterocyclic group, which heterocyclic group may be substituted one or more times with substituents selected from the group consisting of alkyl and acyl, and
R$^{14}$ and R$^{15}$ independently of each another represent hydrogen, alkyl, hydroxy-alkyl, alkoxy-alkyl, carboxyl or acyl; or
R" represents a group of the formula —CO$_2$R$^8$, wherein R$^8$ represents alkyl-NR$^9$R$^{10}$, wherein
R$^9$ and R$^{10}$ together with the nitrogen to which they are attached form a pyrrolidine or a piperazine group, which group may be substituted one or more times with substituents selected from the group consisting of alkyl and acyl.

In an even more preferred embodiment the benzimidazole derivative of the invention is represented by Formula I, wherein R" represents
4-methoxycarbonyl-methyl-3,5-dimethyl-1-piperazinyl;
4-ethoxycarbonyl-methyl-3,5-dimethyl-1-piperazinyl;
4-methyl-3,5-dimethyl-1-piperazinyl;
4-ethyl-3,5-dimethyl-1-piperazinyl; or
3,5-dimethyl-1-piperazinyl.

In a most preferred embodiment the benzimidazole derivative of the invention is

2-Methoxyethyl 1-(3-(4-ethoxycarbonylmethyl-3,5-dimethyl-1-piperazinyl)-phenyl)-benzimidazole-5-carboxylate;
2-Methyl 1-(3-(4-ethoxycarbonylmethyl-3,5-dimethyl-1-piperazinyl)-phenyl)-benzimidazole-5-carboxylate;
2-Methoxyethyl 1-(3-(4-ethyl-3,5-dimethyl-1-piperazinyl)-phenyl)-benzimidazole-5-carboxylate;
2-Methoxyethyl 1-(3-(3,5-dimethyl-1-piperazinyl)-phenyl)-benzimidazole-5-carboxylate; or
2-(3,5-dimethyl-1-piperazinyl)-ethyl 3-(5-acetylbenzimidazol-1-yl)-benzoate oxime;
or a pharmaceutically acceptable salt thereof.

In yet another preferred embodiment the benzimidazole derivative of the invention is represented by Formula I wherein R" represents a group of the formula

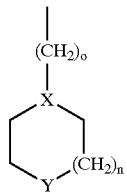

in which formula
o is 0 or 1,
n is 0, 1 or 2,
X represents N or CH, and
Y represents NR$^{11}$ or CHR$^{11}$, wherein
R$^{11}$ represents hydrogen, alkyl, hydroxy-alkyl, carboxy, acyl, or a group of the formula -(alkyl)$_p$-CN-(alkyl)$_p$-aryl, -(alkyl)$_p$-O-aryl, -(alkyl)$_p$-O-aralkyl, -(alkyl)$_t$-COR$^5$ or -(alkyl)$_t$-R$^5$,
wherein
p and t independently of each another is 0 or 1, and
R$^5$ represents hydroxy, alkoxy, NH$_2$, NH(alkyl) or N(alkyl)$_2$.

In a more preferred embodiment,
R" represents
4-(methoxy-carbonyl)-1-piperazinylmethyl;
4-(ethoxy-carbonyl)-1-piperazinylmethyl;
4-(methoxy-carbonyl-methyl)-1-piperazinyl;
4-(ethoxy-carbonyl-methyl)-1-piperazinyl;
4-(methoxy-carbonyl-methyl)-1-piperazinylmethyl;
4-(ethoxy-carbonyl-methyl)-1-piperazinylmethyl;
1-piperazinyl;
1-piperazinyl-methyl;
4-acetyl-1-piperazinyl;
4-methyl-1-piperazinyl;
4-ethyl-1-piperazinyl;
1-methyl-4-piperidinyl;
1-acetyl-4-piperidinyl;
1-methyl-4-piperidyl;
1-acetyl-4-piperidyl;
4-tert-butoxycarbonylmethyl-1-piperazinyl;
4-isopropoxycarbonylmethyl-1-piperazinyl;
4-carboxymethyl-1-piperazinyl;
4-benzyl-1-piperazinyl;
4-cyanomethyl-1-piperazinyl;
4-benzyloxy-ethyl-1-piperazinyl;
4-ethyl-1-homopiperazinyl;
4-(2-hydroxy-ethyl)-1-piperazinyl;
4-carbamoylmethyl-1-piperazinyl;
4-dimethylcarbamoylmethyl-1-piperazinyl; or
4-diethylcarbamoylmethyl-1-piperazinyl.

In a most preferred embodiment, the benzimidazole derivative of the invention is 2-Methoxyethyl 1-(3-(4-(ethoxy-carbonyl)-1-piperazinylmethyl)-phenyl)-benzimidazole-5-carboxylate;
2-Methoxyethyl 1-(3-(4-(ethoxy-carbonyl-methyl)-1-piperazinyl)-phenyl)-benzimidazole-5-carboxylate;
2-Methoxyethyl 1-(3-(4-carboxymethyl-1-piperazinyl)-phenyl)-benzimidazole-5-carboxylate;
2-Methoxyethyl 1-(3-(4-methyl-1-piperazinyl)-phenyl)-benzimidazole-5-carboxylate;
2-Methoxyethyl 1-(3-(4-acetyl-1-piperazinyl)-phenyl)-benzimidazole-5-carboxylate;
2-Methoxyethyl 1-(3-(1-methyl-4-piperidyl)phenyl)benzimidazole-5-carboxylate;
2-Methoxyethyl 1-(3-(1-acetyl-4-piperidyl)-phenyl)-benzimidazole-5-carboxylate;
2-Methoxyethyl 1-(3-(4-t-butoxycarbonylmethyl-1-piperazinyl)-phenyl)-benzimidazole-5-carboxylate;
2-Methoxyethyl 1-(3-(4-1-propoxycarbonylmethyl-1-piperazinyl)-phenyl)-benzimidazole-5-carboxylate;
2-[4-(3-(5-Methoxycarbonylbenzimidazol-1-yl)-phenyl)-1-piperazinyl]-acetic acid;
2-(Methylthio)-ethyl 1-(3-(4-methyl-1-piperazinyl)-phenyl)-benzimidazole-5-carboxylate;
2-(N,N-dimethylamino)-ethyl 1-(3-(1-carboxymethyl-4-piperazinyl)-phenyl)-benzimidazole-5-carboxylate;
2-Methoxyethyl 1-(3-(4-benzyl-1-piperazinyl)-phenyl)-benzimidazole-5-carboxylate;
Methyl 1-(3-(4-cyanomethyl-1-piperazinyl)-phenyl)-benzimidazole-5-carboxylate;
2-Methoxyethyl 1-(3-(4-cyanomethyl-1-piperazinyl)-phenyl)-benzimidazole-5-carboxylate;
Methyl 1-(3-(4-benzyl-1-piperazinyl)-phenyl)-benzimidazole-5-carboxylate;
2-Methoxyethyl 1-(3-(4-benzyloxyethyl-1-piperazinyl)-phenyl)-benzimidazole-5-carboxylate;
2-Methoxyethyl 1-(3-(4-ethyl-1-homopiperazinyl)-phenyl)-benzimidazole-5-carboxylate;
2-Methyl 1-(3-(4-ethyl-1-homopiperazinyl)-phenyl)-benzimidazole-5-carboxylate;
2-Methoxyethyl 1-(3-(4-ethyl-1-piperazinyl)-phenyl)-benzimidazole-5-carboxylate;
2-Hydroxyethyl 1-(3-(4-(2-hydroxyethyl)-1-piperazinyl)-phenyl)-benzimidazole-5-carboxylate;
Methyl 1-(3-(1-piperazinyl)-phenyl)-benzimidazole-5-carboxylate;
2-Methoxyethyl 1-(3-(1-piperazinyl)-phenyl)-benzimidazole-5-carboxylate;
2-Hydroxyethyl 1-(3-(4-methyl-1-piperazinyl)-phenyl)-benzimidazole-5-carboxylate;
2-Hydroxyethyl 1-(3-(4-methoxycarbonylmethyl-1-piperazinyl)-phenyl)-benzimidazole-5-carboxylate;
2-Hydroxyethyl 1-(3-(4-ethoxycarbonylmethyl-1-piperazinyl)-phenyl)-benzimidazole-5-carboxylate;
2-Methoxyethyl 1-(3-(4-diethylcarbamoylmethyl-1-piperazinyl)-phenyl)-benzimidazole-5-carboxylate;
2-Methoxyethyl 1-(3-(4-methoxycarbonylmethyl-1-piperazinyl)-phenyl)-benzimidazole-5-carboxylate;
2-Methoxyethyl 1-(3-(4-carbamoylmethyl-1-piperazinyl)-phenyl)-benzimidazole-5-carboxylate;
2-Hydroxyethyl 1-(3-(4-carbamoylmethyl-1-piperazinyl)-phenyl)-benzimidazole-5-carboxylate;
2-Hydroxyethyl 1-(3-(4-diethylcarbamoylmethyl-1-piperazinyl)-phenyl)-benzimidazole-5-carboxylate;
2-Hydroxyethyl 1-(3-(4-carboxymethyl-1-piperazinyl)-phenyl)-benzimidazole-5-carboxylate;
5-(3-Furanyl)-1-(3-((4-ethoxycarbonyl-1-piperazinyl)-methyl)-phenyl)-benzimidazole;

5-(3-Furanyl)-1-(3-(1-(ethoxy-carbonyl-methyl)-4-piperazinyl)-phenyl)-benzimidazole;
5-(3-Furanyl)-1-(3-(4-t-butoxycarbonylmethyl-1-piperazinyl)-phenyl)-benzimidazole;
5-(3-Furanyl)-1-(3-(1-ethoxycarbonylmethyl-4-piperazinylmethyl)-phenyl)-benzimidazole;
5-(3-Furanyl)-1-(3-(1-ethoxycarbonylmethyl-4-piperidyl)-phenyl)-benzimidazole;
5-(3-Furanyl)-1-(3-(4-ethoxycarbonylpiperid-1-ylmethyl)-phenyl)-benzimidazole; or
5-(3-Furanyl)-1-(3-(1-ethoxycarbonyl-4-piperazinyl)-phenyl)-benzimidazole;
or a pharmaceutically acceptable salt thereof.

Definition of Substituents

In the context of this invention halogen represents a fluorine, a chlorine, a bromine or an iodine atom.

In the context of this invention an alkyl group designates a univalent saturated, straight or branched hydrocarbon chain. The hydrocarbon chain preferably consists of from one to eight carbon atoms ($C_{1-8}$-alkyl), more preferred from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In a preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1,2- or 2,3-propenyl; or 1,2-, 2,3-, or 3,4-butenyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl, 1,2- or 2,3-propynyl, 1,2-, 2,3- or 3,4-butynyl.

In the context of this invention an alkoxy-alkyl group designates an "alkyl-O-alkyl-" group, wherein alkyl is as defined above.

In the context of this invention a thioalkoxy-alkyl group designates an "alkyl-S-alkyl" group wherein alkyl is as defined above;

In the context of this invention an alkoxyalkoxy group designates O-alkyl-O-alkyl wherein alkyl is as defined above.

In the context of this invention an thioalkoxy-alkoxy group designates O-alkyl-S-alkyl wherein alkyl is as defined above.

In the context of this invention an acyl group designates a carboxy group (HOOC—), an alkyl-carbonyl group (alkyl-CO—), or a cycloalkyl-carbonyl (cycloalkyl-CO—), wherein alkyl and cycloalkyl are as defined above. Examples of preferred acyl groups of the invention include carboxy, acetyl, and propionyl.

In the context of this invention an aryl group designates a monocyclic or polycyclic aromatic hydrocarbon group. Examples of preferred aryl groups of the invention include phenyl, naphthyl and anthracenyl.

In the context of this invention an aralkyl group designates a mono- or polycyclic aryl group as defined above, which aryl group is attached to an alkyl group as also defined above. Examples of preferred aralkyl groups of the invention include benzyl, and phenethyl.

In the context of this invention a "Heterocycle" designates a mono- or polycyclic heterocyclic group, which is a mono- or polycyclic group, and which group holds one or more heteroatoms in its ring structure. Preferred heteroatoms include nitrogen (N), oxygen (O), and sulphur (S). One or more of the ring structures may in particular be aromatic (i.e. a heteroaryl), saturated or partially saturated. Preferred heterocyclic monocyclic groups of the invention include 5- and 6-membered heterocyclic monocyclic groups. Preferred poly-heterocyclic groups of the invention are the bicyclic heterocyclic groups.

Examples of preferred aromatic heterocyclic 5-membered monocyclic groups of the invention include
furan, in particular 2- or 3-furanyl;
thiophene, in particular 2- or 3-thienyl;
pyrrole (azole), in particular 1-, 2- or 3-pyrrolyl;
oxazole, in particular oxazol-(2-,4- or 5-)yl;
thiazole, in particular thiazol-(2-,4-, or 5-)yl;
imidazole, in particular imidazol-(1-,2-,4- or 5-)yl;
pyrazole, in particular pyrazol-(1-,3-,4- or 5-)yl;
isoxazole, in particular isoxazol-(3-,4- or 5-)yl;
isothiazole, in particular isothiazol-(3-,4- or 5-)yl;
1,2,3-oxadiazole, in particular 1,2,3-oxadiazol-(4- or 5-)yl;
1,2,4-oxadiazole, in particular 1,2,4-oxadiazol-(3- or 5-)yl;
1,2,5-oxadiazole, in particular 1,2,5-oxadiazol-(3- or 4-)yl;
1,2,3-triazole, in particular 1,2,3-triazol-(1-,4- or 5-)yl;
1,2,4-thiadiazole, in particular 1,2,4-thiadiazol-(3- or 5-)yl;
1,2,5-thiadiazole, in particular 1,2,5-thiadiazol-(3- or 4-)yl; and
1,3,4-thiadiazole, in particular 1,3,4-thiadiazol-(2- or 5-)yl.

Examples of preferred saturated or partially saturated heterocyclic monocyclic 5-membered groups of the invention include
1,3-dioxolan, in particular 1,3-dioxolan-(2- or 4-)yl;
imidazolidine, in particular imidazolidin-(1-,2-,3-,4- or 5-)yl;
2-imidazoline, in particular 2-imidazolin-(1-,2-,4- or 5-)yl;
3-imidazoline, in particular 3-imidazolin-(1-,2-,4- or 5-)yl;
4-imidazoline, in particular 4-imidazolin-(1-,2-,4- or 5-)yl;
2H-oxazole (oxazoline), in particular 2H-oxazol-(2-,4- or 5-)yl;
4H-oxazole (oxazolidine), in particular 4H-oxazol-(2-,4- or 5-)yl;
1,2,3-oxadiazoline, in particular 1,2,3-oxadiazol-(4- or 5-)yl;
1,2,4-oxadiazoline, in particular 1,2,4-oxadiazol-(3- or 5-)yl;
1,2,5-oxadiazoline, in particular 1,2,5-oxadiazol-(3- or 4)yl;
1,2,3-oxadiazolidine, in particular 1,2,3-oxadiazol-(4- or 5-)yl;
1,2,4-oxadiazolidine, in particular 1,2,4-oxadiazol-(3- or 5-)yl;

1,2,5-oxadiazolidine, in particular 1,2,5-oxadiazol-(3- or 4-)yl;

2H-pyrrole (pyrroline), in particular 2H-pyrrol-(1-,2- or 3-)yl;

4H-pyrrole (pyrrolidine), in particular 4H-pyrrol-(1-,2- or 3-)yl;

pyrazolidine, in particular pyrazolidin-(1-,2-,3-,4- or 5-)yl;

2-pyrazoline, in particular 2-pyrazolin-(1-,3-,4- or 5-)yl; and 3-pyrazoline, in particular 3-pyrazolin-(11-,3-,4- or 5-)yl.

Examples of preferred aromatic heterocyclic 6-membered monocyclic groups of the invention include pyridine, in particular pyridin-(2-,3- or 4-)yl;

pyridazine, in particular pyridazin-(3- or 4-)yl;

pyrimidine, in particular pyrimidin-(2-,4- or 5-)yl;

pyrazine, in particular pyrazin-(2-,3-,5- or 6-)yl;

1,3,5-triazine, in particular 1,3,5-triazin-(2-,4- or 6-)yl; and phosphinine, in particular phosphinin-(2-,3- or 4-)yl.

Examples of preferred saturated or partially saturated heterocyclic monocyclic 6-membered groups of the invention include 1,4-dioxolane, in particular 1,4-dioxolan-(2- or 3-)yl;

1,4-dithiane, in particular 1,4-dithian-(2- or 3-)yl;

morpholine, in particular morpholin-(2-,3- or 4-)yl;

1,4-oxazine, in particular 1,4-oxazin-(2-)yl;

oxadiazine, in particular oxadiazin-(2-,3- or 5-)yl;

piperidine, in particular piperidin-(1-,2-,3- or 4-)yl;

piperazine, in particular piperazin-(1-,2-,3- or 4-)yl;

2H-pyrane, in particular 2H-pyran-(2-,3- or 4-)yl;

4H-pyrane, in particular 4H-pyran-(2-,3- or 4-)yl;

thiomorpholine, in particular thiomorpholin-(2-,3- or 4-)yl; and 1,3,5-trithiane, in particular 1,3,5-trithian-(2-)yl.

Examples of preferred saturated or partially saturated heterocyclic monocyclic 7-membered groups of the invention include homopiperidine, in particular homopiperidin-(1-,2-,3- or 4-)yl; and homopiperazine, in particular homopiperazin-(1-,2-,3- or 4-)yl.

Examples of preferred aromatic heterocyclic bi-cyclic groups of the invention include indolizine, in particular indolizin-(1-,2-,3-,5-,6-,7- or 8)yl;

indole, in particular indol-(1-,2-,3-,4-,5-,6- or 7)yl;

isoindole, in particular isoindol-(1-,2-,3-,4-,5-,6- or 7-)yl;

benzo[b]furan (benzofuran), in particular benzo[b]furan-(2-,3-,4-,5-,6- or 7-)yl;

benzo[c]furan (isobenzofuran), in particular benzo[c]furan-(1-,3-,4-,5-,6- or 7-)yl;

benzo[b]thiophene (benzothiophene), in particular benzo[b]thiophen-(2-, 3-,4-,5-,6- or 7-)yl;

benzo[c]thiophene (isobenzothiophene), in particular benzo[c]thiophen-(1-,3-,4-,5-,6- or 7-)yl;

benzimidazole, in particular benzimidazol-(1-,2,4-,5-,6- or 7-)yl;

benzthiazole, in particular benzthiazol-(2-,4-,5-,6- or 7-)yl;

purine, in particular purin-(2-,6- or 8-)yl;

quinoline, in particular quinolin-(2-,3-,4-,5-,6-,7- or 8-)yl;

isoquinoline, in particular isoquinolin-(1-,3-,4-,5-,6-,7- or 8-)yl;

cinnoline, in particular cinnolin-(3-,4-,5-,6-,7- or 8-)yl;

phthlazine, in particular phthlazin-(1-,4-,5-,6-,7- or 8-)yl;

quinazoline, in particular quinazolin-(2-,4-,5-,6-,7- or 8-)yl;

quinoxaline, in particular quinoxalin-(2-,3-,5-,6-,7- or 8-)yl;

1,8-naphyridine, in particular 1,8-naphthyridin-(2-,3-,4-,5-,6- or 7-)yl; and pteridine, in particular pteridin-(2-,4-,6- or 7-)yl.

Examples of preferred aromatic heterocyclic tri-cyclic groups of the invention include carbazole, in particular carbazol-(1-,2-,3-,4-,5-,6-,7-,8- or 9-)yl;

acridine, in particular acridin-(1-,2-,3-,4-,5-,6-,7-,8- or 9-)yl;

phenazine, in particular phenazin-(1-,2-,3-,4-,6-,7-,8- or 9-)yl;

phenothiazine, in particular phenothiazin-(1-,2-,3-,4-,6-,7-,8-,9- or 10-)yl; and phenoxazine, in particular phenoxazin-(1-,2-,3-,4-,6,7-,8-,9- or 10-)yl.

Examples of preferred saturated or partially saturated heterocyclic bi-cyclic groups of the invention include indoline, in particular indolin-(1-,2-,3-,4-,5-,6- or 7-)yl;

3H-indole, in particular 3H-indol-(2-,3-,4-,5-,6- or 7-)yl;

1H-indazole, in particular 1H-indazol-(3-,4-,5-,6- or 7-)yl;

4H-quinolizine, in particular 4H-quinolizin-(1-,2-,3-,4-6-,7-,8- or 9-)yl;

quinuclidine, in particular quinuclidin-(2-,3-,4-,5-,6-,7- or 8-)yl;

isoquinuclidine, in particular isoquinuclidin-(1-,2-,3-,4-,5-,6-,7- or 8-)yl;

tropane, in particular tropan-(1-,2-,3-,4-,5-,6-,7- or 8-)yl; and nortropane, in particular nortropan-(1-,2-,3-,4-,5-,6- or 7-)yl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

The chemical compound of the invention may be provided in dissoluble or indissoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J. Collet A, & Wilen S in *"Enantiomers, Racemates, and Resolutions"*, John Wiley and Sons, New York (1981).

Optical active compounds can also be prepared from optical active starting materials.

Moreover, some of the chemical compounds of the invention may exist in two forms, cis- and trans-form (Z- and E-form), depending on the arrangement of the substituents around the —C═C— double bond. A chemical compound of the present invention may thus be the cis- or the trans-form (Z- and E-form), or it may be a mixture hereof.

Methods of Preparation

The benzimidazole derivatives of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Pharmaceutical Compositions

In another aspect the invention provides novel pharmaceutical compositions comprising a therapeutically effective amount of the benzimidazole derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semi-permeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

As the preferred way of administration is intravenous and by infusion the dose ranges are from 0.01 µg/kg/h to about 10 mg/kg/h.

Biological Activity

It is an object of the present invention to provide compounds capable of modulating the $GABA_A$ receptor complex, which object is met by the provision of the novel benzimidazole derivatives of Formula I.

The benzimidazole derivatives of the invention are particularly useful as anaesthetics and/or pre-anaesthetics, for inducing and maintaining anaesthesia, as sedatives, as muscle relaxants, and for combating febrile convulsions in children, status epilepticus, for use to patients constrained to a respirator.

The benzimidazole derivatives of the invention show a short duration of action, they are water soluble at therapeutic relevant doses, and are particular well suited for intravenous administration.

The compounds of the invention may also be used by veterinarians.

As demonstrated in the working examples the benzimidazole derivatives of the invention show high to moderate affinity for the benzodiazepine receptor as measured by displacement at $^3$H-flunitrazepam in vitro as well as in vivo. The most preferred compounds are full agonists i.e. they exert a high maximal effect in the seizure test as described in the application.

Preferred compounds are full agonists on the $GABA_A$ receptor complex, e.g. as measured by the anticonvulsant activity in the ptz-test described in Example 14, and give rise to a 2–5 fold increase of the tolerated ptz dose. The most preferred compounds are those which increase the tolerated dose the most.

The benzimidazole derivatives of the invention show half-lives of below 30 minutes, which allows for a short duration of action. Preferred half-lives are in the range of from about 30 seconds to about 20 minutes. Most preferred half-lives are in the range of from about 2 to about 5 minutes.

The preferred compounds induce a rapid onset of anaesthesia, i.e. in less than 1–2 minutes. Most preferred is an onset of anaesthesia in less than 1 minute.

Awakening from anaesthesia following a bolus injection (i.v.), or following the attenuation of an infusion, should occur within a short period of time, i.e. of from about 5 to about 30 minutes, preferably of from about 5 to about 10 minutes, after which time the patient should normalise rapidly, i.e. in less than 40 minutes, preferably in less than 20 minutes, as measured from awakening.

The compounds of this invention can be used together with analgetic compounds such as Remifentanile, Fentanyl, or other opiods.

Methods of Therapy

In another aspect the invention provides a method for the treatment, prevention or alleviation of a disease or a disorder or a condition of a living animal body, including a human, which disease, disorder or condition is responsive to modulation of the GABA receptor complex, and which method comprises administering to such a living animal body, including a human, in need thereof an effective amount of benzimidazole derivative of the invention.

In a more preferred embodiment the invention provides a method for the induction or maintenance of anaesthesia or pre-anaesthesia, muscle relaxation or sedation, or for the treatment, prevention or alleviation of fewer cramps or status epilepticus.

It is at present contemplated that suitable infusion rates are in the range of from about 0.01 to about 100 mg/kg/hour, more preferred of from about 0.1 to about 15 mg/kg/hour, dependent upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples which are not intended to be in any way limiting to the scope of the invention as claimed.

Example 1

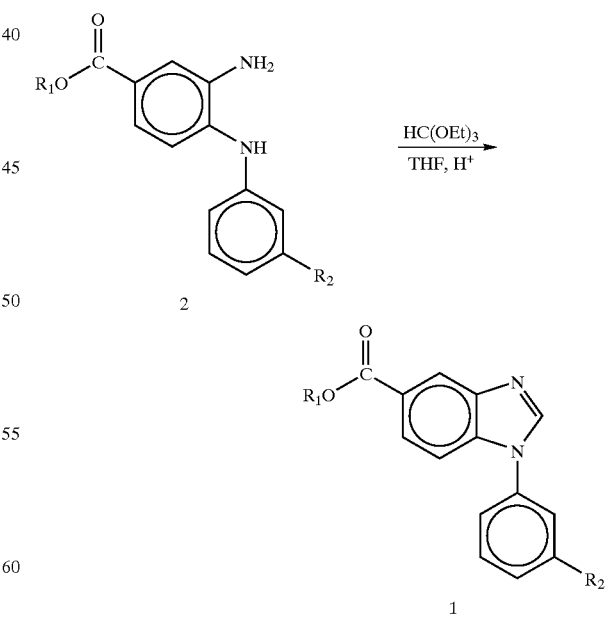

The benzimidazoles of Table 1 were all prepared according to the above scheme as exemplified for compound 1a, below.

TABLE 1

| Comp. No. | R₁ | R₂ | Mp (° C.) | Yield (%) | Starting material | Salt |
|---|---|---|---|---|---|---|
| 1a | MeO(CH$_2$)$_2$ | N-ethylpiperazine-CO$_2$Et | 171–173 | 48 | 2a | HCl |
| 1b | MeO(CH$_2$)$_2$ | N-methylpiperazine-CH$_2$CO$_2$Et | 161–163 | 64 | 2b | HCl |
| 1c | MeO(CH$_2$)$_2$ | N-methylimidazole-CO$_2$Me | 132–134 | 78 | 2c | HCl |
| 1d | MeO(CH$_2$)$_2$ | N-methylpiperazine-CH$_2$COOH | 105–110 | 43 | 2d | — |
| 1e | MeO(CH$_2$)$_2$ | N-methyl-N'-methylpiperazine | 136–137 | 29 | 2e | maleate |
| 1f | MeO(CH$_2$)$_2$ | N-methyl-N'-acetylpiperazine | 157–164 | 53 | 2f | HCl |
| 1g | MeO(CH$_2$)$_2$ | 4-methyl-N-methylpiperidine | 123–125 | 27ª | 2g | HCl |
| 1h | MeO(CH$_2$)$_2$ | 4-methyl-N-acetylpiperidine | 139–140 | 62 | 2h | HCl |
| 1i | MeO(CH$_2$)$_2$ | N-methylpiperazine-CH$_2$CO$_2$tBu | 218–224 | 100 | 2i | HCl |
| 1j | MeO(CH$_2$)$_2$ | N-methylpiperazine-CH$_2$CO$_2$iPr | 155–159 | 69 | 2j | HCl |
| 1k | Et | 3-methylisoxazoline-CH$_2$CO-O-CH$_2$CO-NEt$_2$ | 157–159 | 70 | 2k | HCl |

TABLE 1-continued

| Comp. No. | R₁ | R₂ | Mp (° C.) | Yield (%) | Starting material | Salt |
|---|---|---|---|---|---|---|
| 1l | Me | 1-ethylimidazol-yl | 241–244 | 42 | 2l | HCl |
| 1m | Me | 4-methylpiperazinyl-CH₂COOH | 210–220 | 2 | 2m | HCl |
| 1n | MeS(CH₂)₂ | 1-ethylimidazol-yl | 71–75 | 42 | 2n | — |
| 1o | MeS(CH₂)₂ | 4-methylpiperazinyl | 121–122 | 69 | 2o | — |
| 1p | Me₂N(CH₂)₂ | 4-methylpiperazinyl-CH₂COOH | 47 (decomp.) | 30 | 2p | — |
| 1q | MeO(CH₂)₂ | 4-methylpiperazinyl-CH(CO₂iPr) | 155–159 | 69 | 2q | HCl |
| 1r | MeO(CH₂)₂ | 4-methylpiperazinyl-CH(Ph) | 172–177 | 75 | 2r | HCl |
| 1s | Me | 4-methylpiperazinyl-CH(CN) | 160–162 | 53 | 2s | — |
| 1t | MeO(CH₂)₂ | 4-methylpiperazinyl-CH(CN) | 91–93 | 71 | 2t | — |
| 1u | Me | 4-methylpiperazinyl-CH(Ph) | 153–163 | 70 | 2u | HCl |
| 1v | MeO(CH₂)₂ | 4-methylpiperazinyl-CH₂CH₂OBz | 139–141 | 45 | 2v | HCl |

TABLE 1-continued
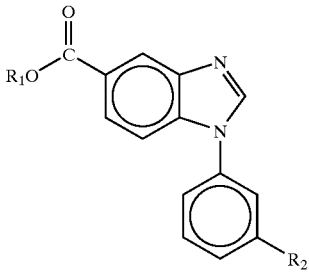
| Comp. No. | $R_1$ | $R_2$ | Mp (° C.) | Yield (%) | Starting material | Salt |
|---|---|---|---|---|---|---|
| 1w | MeO(CH$_2$)$_2$ | 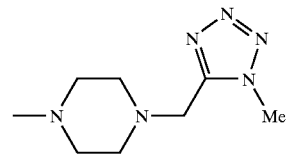 | 196–198 | 73 | 2w | HCl |
| 1x | MeO(CH$_2$)$_2$ | 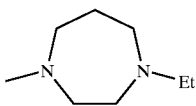 | undefined | 72 | 2x | HCl |
| 1y | Me |  | undefined | 66 | 2y | HCl |
| 1z | MeO(CH$_2$)$_2$ | 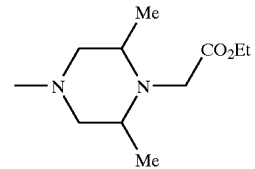 | 166–168 | 26 | 2z | HCl |
| 1aa | MeO(CH$_2$)$_2$ | 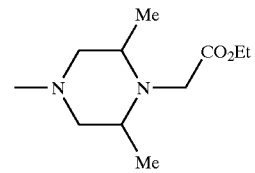 | 90–94 | 59 | 2aa | HCl |
| 1bb | Me | 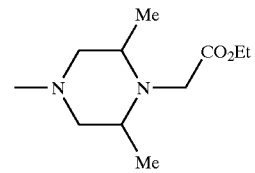 | 168–181 | 48 | 2bb | HCl |
| 1cc | HO(CH$_2$)$_2$ | 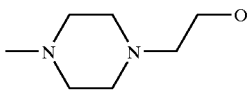 | 182–192 | 34 | 2cc | HCl |
| 1dd | MeO(CH$_2$)$_2$ | 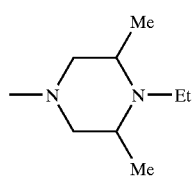 | 202–208 | 24 | 2dd | HCl |
| 1ee | MeO(CH$_2$)$_2$ | 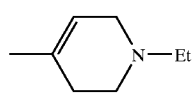 | 179–180 | 69 | 2ee | HCl |

TABLE 1-continued

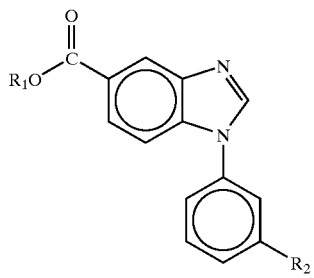

| Comp. No. | R₁ | R₂ | Mp (° C.) | Yield (%) | Starting material | Salt |
|---|---|---|---|---|---|---|
| 1ff | MeO(CH₂)₂ | (piperazinylmethyl-oxazolidinone) | oil | 54 | 2ff | HCl |
| 1gg | MeO(CH₂)₂ | (piperazinylmethyl-5-methyl-1,2,4-oxadiazole) | oil | 100 | 2gg | — |
| 1hh | Me | (methylpiperazine) | 179–202 | 81 | 2hh | 2HCl |
| 1ii | MeO(CH₂)₂ | (methylpiperazine) | 191–205 | 74 | 2ii | 2HCl |
| 1jj | MeO(CH₂)₂ | (piperazinylmethyl-3,5-dimethylisoxazole) | 219–223 | 50 | 2jj | HCl |
| 1kk | MeO(CH₂)₂ | (2,6-dimethylpiperazine) | 215–231 | 92 | 2kk | HCl |
| 1ll | MeO(CH₂)₂ | (piperazinyl-butyrolactone) | 225–254 | 60 | 2ll | HCl |
| 1mm | MeO(CH₂)₂ | (piperazinylmethyl-5-chlorothiophene) | 185–186 | 62 | 2mm | HCl |

TABLE 1-continued

[Structure: R₁O-C(=O)- attached to benzimidazole (carboxylate at 5-position); benzimidazole N1 connected to phenyl bearing R₂ at meta position]

| Comp. No. | R₁ | R₂ | Mp (° C.) | Yield (%) | Starting material | Salt |
|---|---|---|---|---|---|---|
| 1nn | HO(CH₂)₂ | —N(piperazinyl)N—Me | 128–139 | 17 | 2nn | HCl |
| 1oo | HO(CH₂)₂ | —N(piperazinyl)N—CH₂CO₂Me | 150–155 | 44 | 2oo | HCl |
| 1pp | HO(CH₂)₂ | —N(piperazinyl)N—CH₂CO₂Et | 103–125 | 45 | 2pp | HCl |
| 1qq | MeO(CH₂)₂ | —N(piperazinyl)N—CH₂CONEt₂ | 202–204 | 100 | 2qq | HCl |
| 1rr | MeO(CH₂)₂ | —N(piperazinyl)N—CH₂CO₂Me | 161–164 | 72 | 2rr | HCl |
| 1ss | MeO(CH₂)₂ | —N(piperazinyl)N—CH₂CONH₂ | 211–212 | 58 | 2ss | HCl |
| 1tt | HO(CH₂)₂ | —N(piperazinyl)N—CH₂CONH₂ | 268–270 | 79 | 2tt | HCl |
| 1uu | HO(CH₂)₂ | —N(piperazinyl)N—CH₂CONEt₂ | 149–154 | 64 | 2uu | HCl |
| 1vv | HO(CH₂)₂ | —N(piperazinyl)N—CH₂COOH | undefined | 50 | 2vv | HCl |

ᵃthe total yield from three steps.

2-Methoxyethyl 1-(3-(4-(ethoxy-carbonyl)-1-piperazinylmethyl)-phenyl)-benzimidazole-5-carboxylate (1a): A mixture of 2a (0.57 g; 1.25 mmol), triethylorthoformate (0.42 ml; 2.5 mmol) and a catalytic amount of p-toluenesulfonic acid in tetrahydrofurane (10 ml) was heated to reflux for 30 min. The cooled mixture was diluted with ethyl acetate and washed with aqueous sodium hydroxide (1 M). The organic phase was dried over magnesium sulphate and concentrated under reduced pressure. The residue was purified by column-chromatography on silica gel using ethyl acetate as the eluent. The product was precipitated as the hydrochloride by addition of etheral hydrogen chloride to the eluate. Yield: 0.4 g (64%). Mp. 171–173° C.

The following compound were prepared in analogy with Compound 1a:

2-Methoxyethyl 1-(3-(4-(ethoxy-carbonyl-methyl)-1-piperazinyl)-phenyl)-benzimidazole-5-carboxylate (1b) from 2b. A mixture of ethyl acetate and acetone (4:1 v/v) was used as the eluent. Mp. 161–163° C.

2-Methoxyethyl 1-(3-(4-methoxycarbonyl-1-imidazolyl)-phenyl)-benzimidazole-5-carboxylate (1c) from 2c. Mp. 132–134° C.

2-Methoxyethyl 1-(3-(4-carboxymethyl-1-piperazinyl)-phenyl)-benzimidazole-5-carboxylate (1d) from 2d. Mp. 105–110° C. A mixture of acetonitrile, acetic acid and water (8:1:1 v/v/v) was used as the eluent for the column chromatographic purification. No hydrogen chloride was added.

2-Methoxyethyl 1-(3-(4-methyl-1-piperazinyl)-phenyl)-benzimidazole-5-carboxylate (1e) from 2e. Mp. 136–137° C. isolated as the maleate. A mixture of ethyl acetate and acetone (4:1 v/v) was used as the eluent.

2-Metoxyethyl 1-(3-(4-acetyl-1-piperazinyl)-phenyl)-benzimidazole-5-carboxylate (1f) from 2f. Mp. 157–164° C. A mixture of ethyl acetate and acetone (4:1 v/v) was used as the eluent.

2-Methoxyethyl 1-(3-(1-methyl-4-piperidyl)-phenyl)-benzimidazole-5-carboxylate (1g) from 2g. Mp. 123–125° C. A mixture of ethyl acetate and acetone (4:1 v/v) was used as the eluent.

2-Methoxyethyl 1-(3-(1-acetyl-4-piperidyl)-phenyl)-benzimidazole-5-carboxylate (1h) from 2h. Mp. 139–140° C. Acetone was used as the eluent for the column-chromatographic purification.

2-Methoxyethyl 1-(3-(4-t-butoxycarbonylmethyl-1-piperazinyl)-phenyl)-benzimidazole-5-carboxylate (1i) from 2i. Mp. 218–224° C.

2-Methoxyethyl 1-(3-(4-1-propoxycarbonylmethyl-1-piperazinyl)-phenyl)-benzimidazole-5-carboxylate (1j) from 2j. Mp. 155–159° C.

((N,N-Diethylcarbamoyl)-methyl 2-(3-[3-(5-ethoxycarbonyl-1-benzimidazolyl)-phenyl]4,5-dihydroxyisoxazol-5-yl)-acetate (1k) from 2k. Mp. 157–159° C.

Methyl 1-(3-(1-imidazolylmethyl)-phenyl)-benzimidazole-5-carboxylate (1l) from 2l. Mp. 241–244° C. A mixture of dichloromethane and methanol (9:1 v/v) was used as the eluent.

2-[4-(3-(5-Methoxycarbonylbenzimidazol-1-yl)-phenyl)-1-piperazinyl]-acetic acid (1m) from 2m. Mp. 210–220° C. The product was chromatographied twice using a mixture of acetonitrile, water and acetic acid (8:1:1 v/v/v) as the eluent.

2-(Methylthio)-ethyl 1-(3-(1-imidazolylmethyl)-phenyl)-benzimidazole-5-carboxylate (1n) from 2n. Mp. 71–75° C. A mixture of dichloromethane, methanol and aqueous ammonia (90:10:1 v/v/v) was used as the eluent. Isolated as the free base.

2-(Methylthio)-ethyl 1-(3-(4-methyl-1-piperazinyl)-phenyl)-benzimidazole-5-carboxylate (1o) from 2o. Mp. 121–122° C.

2-(N,N-dimethylamino)-ethyl 1-(3-(1-carboxymethyl-4-piperazinyl)-phenyl)-benzimidazole-5-carboxylate (1p) from 2p. Mp. 47° C. (with decomposition). A mixture of acetonitrile, acetic acid, pyridine and water (7:1:1:1 v/v/v/v) was used as the eluent.

2-Methoxyethyl 1-(3-(1-isopropoxycarbonylmethyl-4-piperazinyl)-phenyl)-benzimidazole-5-carboxylate (1q) from 2q. Mp. 155–159° C.

2-Methoxyethyl 1-(3-(4-benzyl-1-piperazinyl)-phenyl)-benzimidazole-5-carboxylate (1r) from 2r. Mp. 172–177° C.

Methyl 1-(3-(4-cyanomethyl-1-piperazinyl)-phenyl)-benzimidazole-5-carboxylate (1s) from 2s. Mp. 160–162° C. The product was isolated as the free base.

2-Methoxyethyl 1-(3-(4-cyanomethyl-1-piperazinyl)-phenyl)-benzimidazole-5-carboxylate (1t) from 2t. Mp. 91–93° C. The product was isolated as the free base.

Methyl 1-(3-(4-benzyl-1-piperazinyl)-phenyl)-benzimidazole-5-carboxylate (1u) from 2u. Mp. 153–163° C.

2-Methoxyethyl 1-(3-(4-benzyloxyethyl-1-piperazinyl)-phenyl)-benzimidazole-5-carboxylate (1v) from 2v. Mp. 139–141° C.

2-Methoxyethyl 1-(3-(4-(1-methyl-5-tetrazolyl) methyl-1-piperazinyl)-phenyl)-benzimidazole-5-carboxylate (1w) from 2w. Mp. 196–198° C.

2-Methoxyethyl 1-(3-(4-ethyl-1-homopiperazinyl)-phenyl)-benzimidazole-5-carboxylate (1x) from 2x. Mp. undefined. A mixture of dichloromethane and methanol (9:1 v/v) was used as the eluent.

2-Methyl 1-(3-(4-ethyl-1-homopiperazinyl)-phenyl)-benzimidazole-5-carboxylate (1y) from 2y. Mp. undefined. A mixture of dichloromethane and methanol (9:1 v/v) was used as the eluent.

2-Methoxyethyl 1-(3-(4-ethyl-1-piperazinyl)-phenyl)-benzimidazole-5-carboxylate (1z) from 2z. Mp. 166–168° C.

2-Methoxyethyl 1-(3-(4-ethoxycarbonylmethyl-3,5-dimethyl-1-piperazinyl)-phenyl)-benzimidazole-5-carboxylate (1aa) from 2aa. Mp. 90–94° C.

2-Methyl 1-(3-(4-ethoxycarbonylmethyl-3,5-dimethyl-1-piperazinyl)-phenyl)-benzimidazole-5-carboxylate (1bb) from 2bb. Mp. 168–181° C.

2-Hydroxyethyl 1-(3-(4-(2-hydroxyethyl)-1-piperazinyl)-phenyl)-benzimidazole-5-carboxylate (1cc) from 2 cc. Mp. 182–192° C. A mixture of ethyl acetate and methanol (1:1 v/v) was used as the eluent.

2-Methoxyethyl 1-(3-(4-ethyl-3,5-dimethyl-1-piperazinyl)-phenyl)-benzimidazole-5-carboxylate (1dd) from 2dd. Mp. 202–208° C. A mixture of ethyl acetate and methanol (1:1 v/v) was used as the eluent.

2-Methoxyethyl 1-(3-(1 ethyl-1,2,5,6-tetrahydropyridin-4-yl)-phenyl)-benzimidazole-5-carboxylate (1ee) from 2ee. Mp. 179–180° C.

2-Methoxyethyl 1-(3-(4-(2-oxazolidinone-5-yl)methyl)1-piperazinyl)-phenyl)-benzimidazole-5-carboxylate (1ff) from 2ff. Isolated as an oil.

2-Methoxyethyl 1-(3-(4-(5-methyloxadiazol-3-yl) methyl)1-piperazinyl)-phenyl)-benzimidazole-5-carboxylate (1gg) from 2gg. Isolated as an oil.

Methyl 1-(3-(1-piperazinyl)-phenyl)-benzimidazole-5-carboxylate (1hh) from 2hh. Mp. 179–202° C. The Boc-group was removed subsequently to the ring closure by treatment with trifluoroacetic acid in dichloromethane.

2-Methoxyethyl 1-(3-(1-piperazinyl)-phenyl)-benzimidazole-5-carboxylate (1ii) from 2ii. Mp. 191–205° C. The Boc-group was removed subsequently to the ring closure by treatment with trifluoroacetic acid in dichloromethane.

2-Methoxyethyl 1-(3-(4-(3,5-dimethylisoxazol-4-yl) methyl)1-piperazinyl)-phenyl)-benzimidazole-5-carboxylate (1jj) was prepared from 1ii by alkylation with 4-chloromethyl-3,5-dimethylisoxazol. Mp. 219–223° C.

2-Methoxyethyl 1-(3-(3,5-dimethyl-1-piperazinyl)-phenyl)-benzimidazole-5-carboxylate (1kk) from 2kk. Mp. 215–231° C. The Boc-group was removed subsequently to the ring closure by treatment with trifluoroacetic acid in dichloromethane.

2-Methoxyethyl 1-(3-(4-(2-oxo-tetrahydrofuran-3-yl)-1-piperazinyl)-phenyl)-benzimidazole-5-carboxylate (1ll) from 2ll. Mp. 225–254° C.

2-Methoxyethyl 1-(3-(4-(2-chloro-5-thienyl)methyl-1-piperazinyl)-phenyl)-benzimidazole-5-carboxylate (1mm) was prepared from 1ii by alkylation with 2-chloromethyl-5-chlorothiophene. Mp. 185–186° C.

2-Hydroxyethyl 1-(3-(4-methyl-1-piperazinyl)-phenyl)-benzimidazole-5-carboxylate (1nn) from 2nn. Mp. A mixture of ethyl acetate and methanol (1:1v/v) was used as the eluent.

2-Hydroxyethyl 1-(3-(4-methoxycarbonylmethyl-1-piperazinyl)-phenyl)-benzimidazole-5-carboxylate (1oo) from 2oo. Mp. A mixture of ethyl acetate and methanol (9:1v/v) was used as the eluent.

2-Hydroxyethyl 1-(3-(4-ethoxycarbonylmethyl-1-piperazinyl)-phenyl)-benzimidazole-5-carboxylate (1pp) from 2pp. Mp. A mixture of ethyl acetate and methanol (9:1v/v) was used as the eluent.

2-Methoxyethyl 1-(3-(4-diethylcarbamoylmethyl-1-piperazinyl)-phenyl)-benzimidazole-5-carboxylate (1qq) from 2qq. Mp. 202–204° C. A mixture of ethyl acetate and methanol (9:1v/v) was used as the eluent.

2-Methoxyethyl 1-(3-(4-methoxycarbonylmethyl-1-piperazinyl)-phenyl)-benzimidazole-5-carboxylate (1rr) from 2rr. Mp. 161–164° C. A mixture of ethyl acetate and methanol (9:1 v/v) was used as the eluent.

2-Methoxyethyl 1-(3-(4-carbamoylmethyl-1-piperazinyl)-phenyl)-benzimidazole-5-carboxylate (1ss) from 2ss. Mp. 211–212° C. A mixture of ethyl acetate and methanol (9:1v/v) was used as the eluent.

2-Hydroxyethyl 1-(3-(4-carbamoylmethyl-1-piperazinyl)-phenyl)-benzimidazole-5-carboxylate (1tt) from 2tt. Mp. 268–270° C. A mixture of ethyl acetate and methanol (9:1v/v) was used as the eluent.

2-Hydroxyethyl 1-(3-(4-diethylcarbamoylmethyl-1-piperazinyl)-phenyl)-benzimidazole-5-carboxylate (1uu) from 2uu. Mp. 149–154° C. A mixture of ethyl acetate and methanol (9:1v/v) was used as the eluent.

2-Hydroxyethyl 1-(3-(4-carboxymethyl-1-piperazinyl)-phenyl)-benzimidazole-5-carboxylate (1vv) from 2vv. DMF was used as the solvent and a mixture of acetonitril, water and acetic acid (8:1:1 v/v/v) was used as the eluent.

Example 2

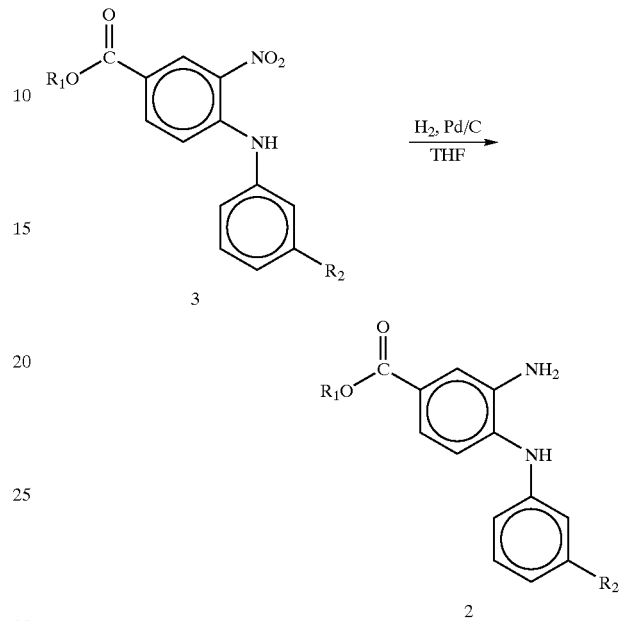

The diamines of Table 2 were all prepared quantitatively by hydrogenation of the corresponding nitroanilines (3), according to the above scheme as exemplified for 2a below.

TABLE 2

| Compound No. | $R_1$ | $R_2$ | Starting material |
|---|---|---|---|
| 2a | $MeO(CH_2)_2$ | piperazine-N-CH$_2$CO$_2$Et (2-position) | 3a |
| 2b | $MeO(CH_2)_2$ | 4-methylpiperazine-N-CH$_2$CO$_2$Et | 3b |
| 2c | $MeO(CH_2)_2$ | 1-methylimidazole-4-CO$_2$Me | 3c |

TABLE 2-continued

| Compound No. | R₁ | R₂ | Starting material |
|---|---|---|---|
| 2e | MeO(CH₂)₂ | 4-methylpiperazin-1-yl (N-Me, NMe) | 3e |
| 2f | MeO(CH₂)₂ | 4-acetylpiperazin-1-yl (N-Me, NAc) | 3f |
| 2g | MeO(CH₂)₂ | 4-methylpiperidin-1-yl (NMe) | 3g |
| 2h | MeO(CH₂)₂ | 4-acetylpiperidin-1-yl (NAc) | 3h |
| 2i | MeO(CH₂)₂ | 4-methylpiperazin-1-yl-CH₂CO₂tBu | 3i |
| 2j | MeO(CH₂)₂ | 4-methylpiperazin-1-yl-CH₂CO₂iPr | 3j |
| 2k | Et | 3-methyl-4,5-dihydroisoxazol-5-yl-CH₂C(O)OCH₂C(O)N(Et)₂ | 3k |
| 2l | Me | 1-ethylimidazol-2-yl | 3l |
| 2n | MeS(CH₂)₂ | 1-ethylimidazol-2-yl | 3n |
| 2o | MeS(CH₂)₂ | 4-methylpiperazin-1-yl (N-Me, NMe) | 3o |
| 2r | MeO(CH₂)₂ | 4-methyl-1-(benzyl)piperazin-1-yl (N-Me, NCH₂Ph) | 3r |

TABLE 2-continued
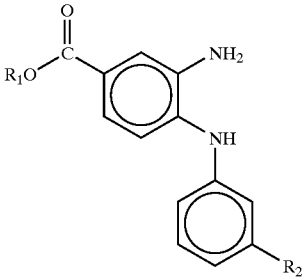
| Compound No. | R₁ | R₂ | Starting material |
|---|---|---|---|
| 2s | Me | 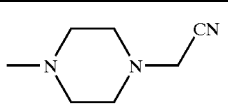 | 3s |
| 2t | MeO(CH₂)₂ | 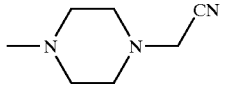 | 3t |
| 2u | Me | 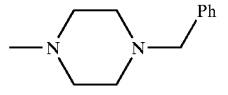 | 3u |
| 2v | MeO(CH₂)₂ | 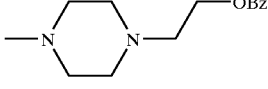 | 3v |
| 2w | MeO(CH₂)₂ | 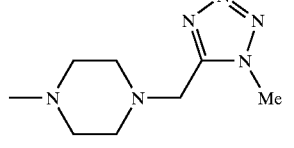 | 3w |
| 2x | MeO(CH₂)₂ | 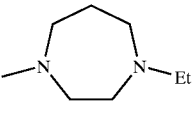 | 3x |
| 2y | Me | 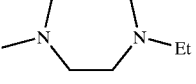 | 3y |
| 2z | MeO(CH₂)₂ | 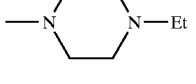 | 3z |
| 2aa | MeO(CH₂)₂ | 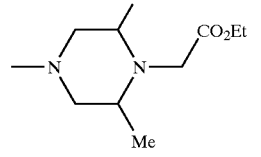 | 3aa |

TABLE 2-continued
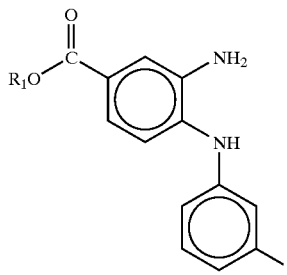
| Compound No. | R₁ | R₂ | Starting material |
|---|---|---|---|
| 2bb | Me | 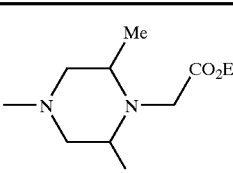 | 3bb |
| 2cc | HO(CH₂)₂ | 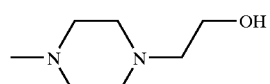 | 3cc |
| 2dd | MeO(CH₂)₂ | 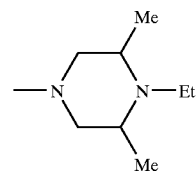 | 3dd |
| 2ee | MeO(CH₂)₂ | 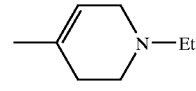 | 3ee |
| 2ff | MeO(CH₂)₂ | 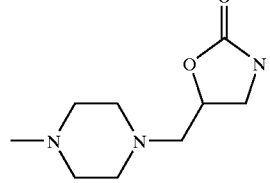 | 3ff |
| 2gg | MeO(CH₂)₂ | 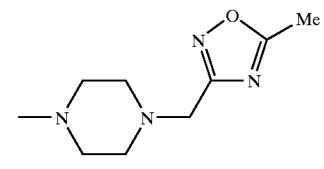 | 3gg |
| 2hh | Me | 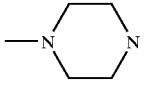 | 3hh |
| 2ii | MeO(CH₂)₂ | 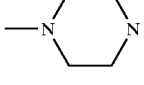 | 3ii |

TABLE 2-continued

| Compound No. | R₁ | R₂ | Starting material |
|---|---|---|---|
| 2jj | MeO(CH$_2$)$_2$ | (4-((3,5-dimethylisoxazol-4-yl)methyl)piperazin-1-yl) | 3jj |
| 2kk | MeO(CH$_2$)$_2$ | (3,5-dimethylpiperazin-1-yl) | 3kk |
| 2ll | MeO(CH$_2$)$_2$ | (4-(2-oxotetrahydrofuran-3-yl)piperazin-1-yl) | 3ll |
| 2mm | MeO(CH$_2$)$_2$ | (4-((5-chlorothiophen-2-yl)methyl)piperazin-1-yl) | 3mm |
| 2nn | HO(CH$_2$)$_2$ | (4-methylpiperazin-1-yl) | 3nn |
| 2oo | HO(CH$_2$)$_2$ | (4-(methoxycarbonylmethyl)piperazin-1-yl) | 3oo |
| 2pp | HO(CH$_2$)$_2$ | (4-(ethoxycarbonylmethyl)piperazin-1-yl) | 3pp |
| 2qq | MeO(CH$_2$)$_2$ | (4-(diethylcarbamoylmethyl)piperazin-1-yl) | 3qq |
| 2rr | MeO(CH$_2$)$_2$ | (4-(methoxycarbonylmethyl)piperazin-1-yl) | 3rr |

TABLE 2-continued

[Structure: benzoate with R1O-C(=O)- group, NH2, and NH-phenyl-R2 substituents]

| Compound No. | R₁ | R₂ | Starting material |
|---|---|---|---|
| 2ss | MeO(CH$_2$)$_2$ | —N(piperazine)N—CH$_2$CONH$_2$ | 3ss |
| 2tt | HO(CH$_2$)$_2$ | —N(piperazine)N—CH$_2$CONH$_2$ | 3tt |
| 2uu | HO(CH$_2$)$_2$ | —N(piperazine)N—CH$_2$CONEt$_2$ | 3uu |
| 2vv | HO(CH$_2$)$_2$ | —N(piperazine)N—CH$_2$COOH | 3vv |

2-Methoxyethyl 3-amino-4-(3-((1-ethoxycarbonyl-4-piperazinyl)-methyl)-phenylamino)-benzoate (2a). 3a (0.75 g; 1.54 mmol) was suspended in tetrahydrofurane. Palladium catalyst (50 mg, 5% on activated carbon) was added and the mixture was hydrogenated at ambient pressure until the hydrogen uptake had ceased. The mixture was filtered through celite and the filtrate was evaporated to dryness to leave 2a, quantitatively.

The following compound were prepared in analogy with Compound 2a:

2-Methoxyethyl 3-amino-4-(3-(1-(ethoxy-carbonyl-methyl)-4-piperazinylmethyl)-phenylamino)-benzoate (2b) from 3b.

2-Methoxyethyl 3-amino-4-(3-(4-methoxycarbonyl-1-imidazolyl)-phenylamino)-benzoate (2c) from 3c.

2-Methoxyethyl 3-amino-4-(3-(1-methyl-4-piperazinyl)-phenylamino)-benzoate (2e) from 3e.

2-Methoxyethyl 3-amino-4-(3-(1-acetyl-4-piperazinyl)-phenylamino)-benzoate (2f) from 3f.

2-Methoxyethyl 3-amino-4-(3-(1-methyl-4-piperidyl)-phenylamino)-benzoate (2g) from 3g.

2-Methoxyethyl 3-amino-4-(3-(1-acetyl-4-piperidyl)-phenylamino)-benzoate (2h) from 3h.

2-Methoxyethyl 3-amino-4-(3-(1-t-butoxycarbonylmethyl-4-piperazinyl)-Phenylamino)-benzoate (2i) from 3i.

2-Methoxyethyl 3-amino-4-(3-(1-1-propoxycarbonylmethyl-4-piperazinyl)-phenylamino)-benzoate (2j) from 3j.

(N,N-Diethylcarbamoyl)-methyl 2-[3-(3-((2-amino-4-ethoxycarbonylphenyl) amino)-phenyl)-4,5-dihydroisoxazol-5-yl]-acetate (2k) from 3k.

Methyl 3-amino-4-(3-((1-imidazolyl)-methyl)-phenylamino)-benzoate (2l) from 3l.

2-(Methylthio)-ethyl 3-amino-4-(3-(1-imidazolylmethyl)-phenylamino)-benzoate (2n) from 3n using raney nickel as the catalyst.

2-(Methylthio)-ethyl 3-amino-4-(3-(4-methyl-1-piperazinyl)-phenylamino)-benzoate (2o) from 3o.

2-Methoxyethyl 3-amino-4-(3-(1-benzyl-4-piperazinyl)-phenylamino)-benzoate (2r) from 3r. PtO$_2$ was used as the catalyst.

Methyl 3-amino-4-(3-(1-cyanomethyl-4-piperazinyl)-phenylamino)-benzoate (2s) from 3s.

2-Methoxyethyl 3-amino-4-(3-(1-cyanomethyl-4-piperazinyl)-phenylamino)-benzoate (2t) from 3t. PtO$_2$ was used as the catalyst.

Methyl 3-amino-4-(3-(1-benzyl-4-piperazinyl)-phenylamino)-benzoate (2u) from 3u. PtO$_2$ was used as the catalyst.

2-Methoxyethyl 3-amino-4-(3-(1-(2-benzyloxyethyl)-4-piperazinyl)-phenylamino)-benzoate (2v) from 3v. PtO$_2$ was used as the catalyst.

2-Methoxyethyl 3-amino-4-(3-(1-((1-methyl-5-tetrazolyl)-methyl)-4-piperazinyl)-phenylamino)-benzoate (2w) from 3w. PtO$_2$ was used as the catalyst.

2-Methoxyethyl 3-amino-4-(3-(1-ethyl-4-homopiperazinyl)-phenylamino)-benzoate (2x) from 3x.

Methyl 3-amino-4-(3-(1-ethyl-4-homopiperazinyl)-phenylamino)-benzoate (2y) from 3y.

2-Methoxyethyl 3-amino-4-(3-(1-ethyl-4-piperazinyl)-phenylamino)-benzoate (2z) from 3z.

2-Methoxyethyl 3-amino-4-(3-((1-(ethoxy-carbonyl-methyl)-2,6-dimethyl)-4-piperazinylmethyl)-phenylamino)-benzoate (2aa) from 3aa.

Methyl 3-amino-4-(3-((1-(ethoxy-carbonyl-methyl)-2,6-dimethyl)-4-piperazinylmethyl)-phenylamino)-benzoate (2bb) from 3bb.

2-Hydroxyethyl 3-amino-4-(3-(1-(2-hydroxyethyl)-4-piperazinyl)-phenylamino)-benzoate (2 cc) from 3 cc.

2-Methoxyethyl 3-amino-4-(3-((1-ethyl-2,6-dimethyl)-4-piperazinylmethyl)-phenylamino)-benzoate (2dd) from 3dd.

2-Methoxyethyl 3-amino-4-(3-(1-(2-oxazolinon-5-yl)methyl-4-piperazinyl)-phenylamino)-benzoate (2ff) from 3ff.

2-Methoxyethyl 3-amino-4-(3-(1-(5-methyloxadiazol-3-yl)methyl-4-piperazinyl)-phenylamino)-benzoate (2gg) from 3gg. $PtO_2$ was used as the catalyst.

Methyl 3-amino-4-(3-(1-boc-4-piperazinyl)-phenylamino)-benzoate (2hh) from 3hh.

2-Methoxyethyl 3-amino-4-(3-(1-boc-4-piperazinyl)-phenylamino)-benzoate (2ii) from 3ii.

2-Methoxyethyl 3-amino-4-(3-(1-boc-2,6-dimethyl-4-piperazinyl)-phenylamino)-benzoate (2kk) from 3kk.

2-Methoxyethyl 3-amino-4-(3-(1-(2-oxotetrahydrofuran-3-yl)-4-piperazinyl)-phenylamino)-benzoate (2ll) from 3ll.

2-Hydroxyethyl 3-amino-4-(3-(4-methyl-1-piperazinyl)-phenylamino)-benzoate (2nn) from 3nn.

2-Hydroxyethyl 3-amino-4-(3-(4-methoxycarbonylmethyl-1-piperazinyl)-phenylamino)-benzoate (2oo) from 3oo.

2-Hydroxyethyl 3-amino-4-(3-(4-ethoxycarbonylmethyl-1-piperazinyl)-phenylamino)-benzoate (2 pp) from 3 pp.

2-Methoxyethyl 3-amino-4-(3-(4-(N,N-diethyl-carbamoyl)methyl-1-piperazinyl)-phenylamino)-benzoate (2qq) from 3qq.

2-Methoxyethyl 3-amino-4-(3-(4-methoxycarbonylmethyl-1-piperazinyl)-phenylamino)-benzoate (2rr) from 3rr.

2-Methoxyethyl 3-amino-4-(3-(4-carbamoylmethyl-1-piperazinyl)-phenylamino)-benzoate (2ss) from 3ss.

2-Hydroxyethyl 3-amino-4-(3-(4-carbamoylmethyl-1-piperazinyl)-phenylamino)-benzoate (2tt) from 3tt.

2-Hydroxyethyl 3-amino-4-(3-(4-(N,N-diethyl-carbamoyl)-methyl-1-piperazinyl)-phenylamino)-benzoate (2uu) from 3uu.

Example 2a

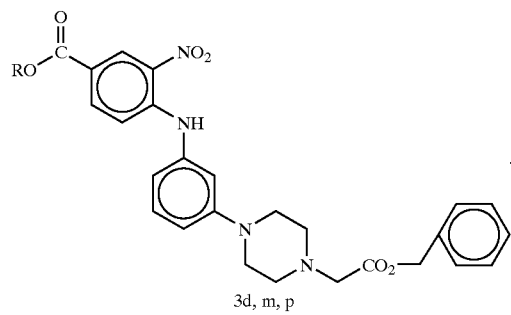

3d, m, p $H_2/Pd$

-continued

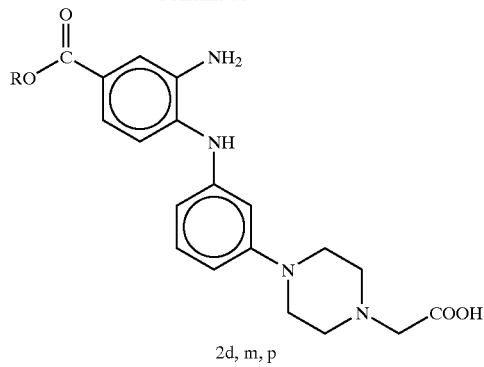

2d, m, p

2-Methoxyethyl 3-amino-4-(3-(1-carboxymethyl-4-piperazinyl)-phenylamino)-benzoate (2d). To a solution of 2-methoxyethyl 3-nitro-4-(3-(4-(benzyloxy-carbonyl-methyl)-1-piperazinyl)-phenylamino)-benzoate (3d) (3.5 g; 6.4 mmol) in a mixture of tetrahydrofurane (50 ml) and DMF (5 ml) was added palladium catalyst (0.9 g, 5% Pd on activated carbon) and ammonium formiate (0.8 g; 12.6 mmol) and the mixture was heated to reflux for 2 hours. The cooled mixture was filtered through celite and the solvent was removed under reduced pressure to leave 2d, quantitatively.

The following compound were prepared in analogy with Compound 2d

Methyl 3-amino-4-(3-(1-carboxymethyl-4-piperazinyl)-phenylamino)-benzoate (2m) from 3m.

2-(Dimethylamino)-ethyl 3-amino-4-(3-(1-carboxymethyl-4-piperazinyl)-phenylamino)-benzoate (2p) from 3p.

2-Hydroxyethyl 3-amino-4-(3-(1-carboxymethyl-4-piperazinyl)-phenylamino)-benzoate (2vv) from 3vv.

Example 2b

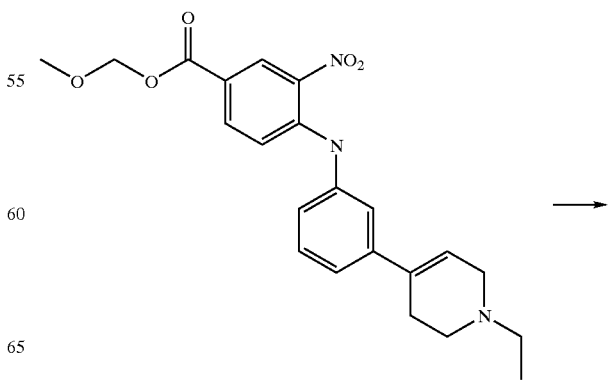

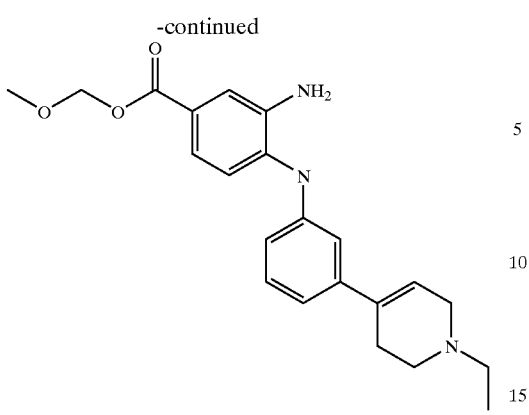

2-Methoxyethyl 3-amino-4-(3-(1-ethyl-1,2,5,6-tetrahydropyridin-4-yl)-phenylamino)-benzoate (2ee) from 3ee. A mixture of 3ee (0.97 g; 1.9 mmol), sodium sulphide nonahydrate (1.37 g; 5,71 mmol) and ammonium chloride (0.3 g; 5.61 mmol) in a mixture of THF (5 ml) and 2-methoxyethanol (5 ml) was heated to 80° C. for two hours. The cooled mixture was poured into ice-water and extracted with ethyl acetate. The extract was dried over magnesium sulphate, filtered and evaporated to dryness. The residue was purified on a silica gel column using a mixture of ethyl acetate and methanol (9:1 v/v) as the eluent. Yield: 0.21 g.

Example 3

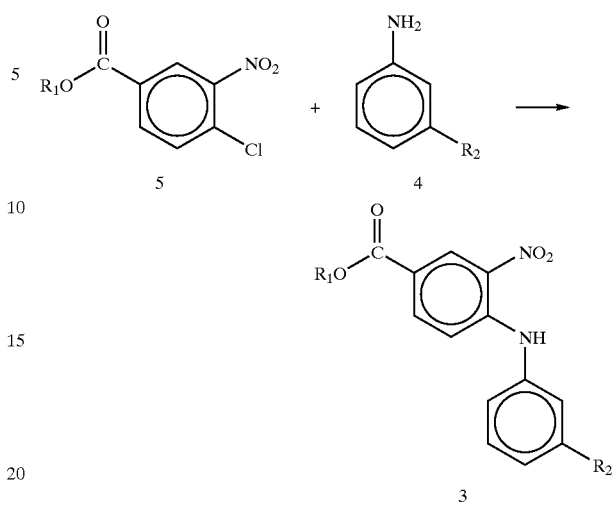

The nitroanilines of Table 3 were prepared by reaction of 4-chloro-3-nitrobenzoates 5 with substituted anilines (4), according to the above scheme as exemplified for compound 3a below.

TABLE 3

| Comp. No. | $R_1$ | $R_2$ | Starting materials | Yield (%) |
|---|---|---|---|---|
| 3a | MeO(CH$_2$)$_2$ | ethyl-piperazinyl-CO$_2$Et | 4a, 5a | 43 |
| 3b | MeO(CH$_2$)$_2$ | methyl-piperazinyl-CH$_2$CO$_2$Et | 4b, 5a | 67 |
| 3c | MeO(CH$_2$)$_2$ | 1-methyl-imidazol-4-yl-CO$_2$Me | 4c, 5a | 37 |
| 3d | MeO(CH$_2$)$_2$ | methyl-piperazinyl-CH$_2$CO$_2$Bz | 4d, 5a | 52 |
| 3e | MeO(CH$_2$)$_2$ | 4-methylpiperazinyl | 4e, 5a | 81 |

TABLE 3-continued
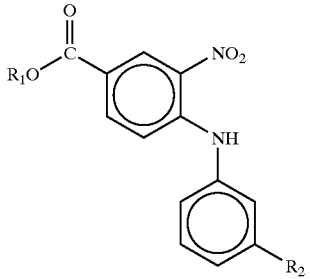
| Comp. No. | R₁ | R₂ | Starting materials | Yield (%) |
|---|---|---|---|---|
| 3f | MeO(CH₂)₂ | 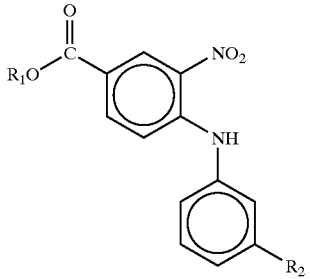 | 4f, 5a | 58 |
| 3g | MeO(CH₂)₂ |  | 4g, 5a | — |
| 3h | MeO(CH₂)₂ | 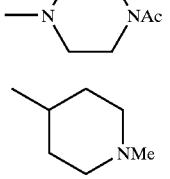 | 4h, 5a | 74 |
| 3i | MeO(CH₂)₂ | 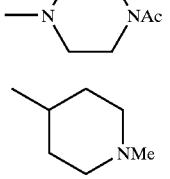 | 4i, 5a | 45 |
| 3j | MeO(CH₂)₂ |  | 4j, 5a | 57 |
| 3k | Et | 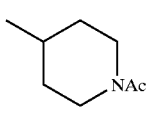 | 4k, 5b | 63 |
| 3l | Me | 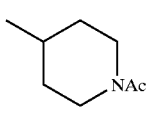 | 4l, 5c | 32 |
| 3m | Me |  | 4d, 5c | 88 |
| 3n | MeS(CH₂)₂ | 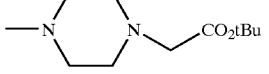 | 4l, 5d | 16 |
| 3o | MeS(CH₂)₂ | 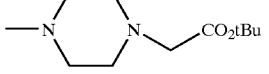 | 4e, 5d | 78 |
| 3p | Me₂N(CH₂)₂ |  | 4d, 5e | 63 |

TABLE 3-continued
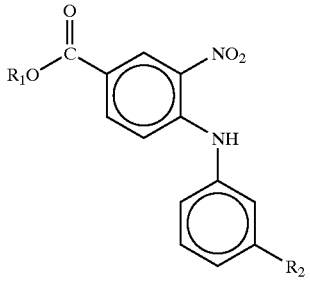
| Comp. No. | R₁ | R₂ | Starting materials | Yield (%) |
|---|---|---|---|---|
| 3p | Me₂N(CH₂)₂ | 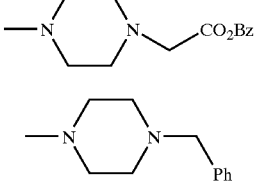 | 4d, 5e | 63 |
| 3r | MeO(CH₂)₂ | 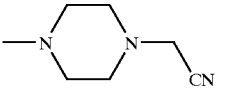 | 4s, 5a | 65 |
| 3s | Me | 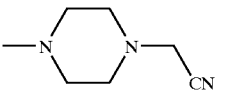 | 4t, 5c | 53 |
| 3t | MeO(CH₂)₂ | 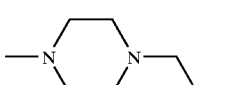 | 4t, 5a | 74 |
| 3u | Me | 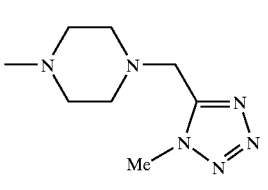 | 4s, 5c | 65 |
| 3w | MeO(CH₂)₂ | 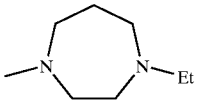 | 4u, 5a | 37 |
| 3x | MeO(CH₂)₂ | 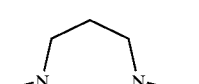 | 4v, 5a | 100 |
| 3y | Me | 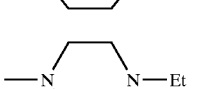 | 4v, 5c | 100 |
| 3z | MeO(CH₂)₂ | | 4x, 5a | 100 |
| 3aa | MeO(CH₂)₂ | 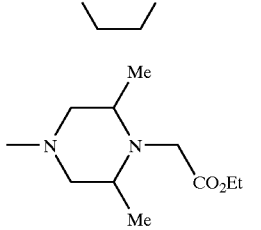 | 4y, 5a | 61 |

TABLE 3-continued

| Comp. No. | R$_1$ | R$_2$ | Starting materials | Yield (%) |
|---|---|---|---|---|
| 3bb | Me | piperazine with two Me groups, N-Me, N-CH$_2$CO$_2$Et | 4y, 5c | 33 |
| 3cc | HO(CH$_2$)$_2$ | N-methylpiperazine-N'-CH$_2$CH$_2$OH | 4z, 5f | 90 |
| 3dd | MeO(CH$_2$)$_2$ | piperazine with two Me groups, N-Me, N-Et | 4aa, 5a | 100 |
| 3ee | MeO(CH$_2$)$_2$ | 4-methyl-1-ethyl-tetrahydropyridine | 4bb, 5a | 70 |
| 3ff | MeO(CH$_2$)$_2$ | N-methylpiperazine-N'-CH$_2$-(oxazolidin-2-one) | 4cc, 5a | 50 |
| 3gg | MeO(CH$_2$)$_2$ | N-methylpiperazine-N'-CH$_2$-(5-methyl-1,2,4-oxadiazol-3-yl) | 4dd, 5a | 71 |
| 3hh | Me | N-methyl-N'-boc-piperazine | 4ee, 5c | 38 |
| 3ii | MeO(CH$_2$)$_2$ | N-methyl-N'-boc-piperazine | 4ee, 5a | 69 |

TABLE 3-continued

*[Structure: benzoate with $R_1O$-C(=O)- group, $NO_2$ substituent, NH linker to phenyl ring bearing $R_2$]*

| Comp. No. | $R_1$ | $R_2$ | Starting materials | Yield (%) |
|---|---|---|---|---|
| 3kk | MeO(CH$_2$)$_2$ | 2,6-dimethyl-4-boc-piperazin-1-yl (via CH$_2$) | 4ff, 5a | 89 |
| 3ll | MeO(CH$_2$)$_2$ | 4-methylpiperazin-1-yl attached to 3-(2-oxotetrahydrofuran-3-yl) | 4gg, 5a | 75 |
| 3nn | HO(CH$_2$)$_2$ | —N(piperazine)N—Me | 4e, 5f | 59 |
| 3oo | HO(CH$_2$)$_2$ | piperazinyl-CH$_2$-CO$_2$Me | 5f | 56 |
| 3pp | HO(CH$_2$)$_2$ | piperazinyl-CH$_2$-CO$_2$Et | 4b, 5f | 27 |
| 3qq | MeO(CH$_2$)$_2$ | piperazinyl-CH$_2$-CONEt$_2$ | 4ii, 5a | 24 |
| 3rr | MeO(CH$_2$)$_2$ | piperazinyl-CH$_2$-CO$_2$Me | 5a | 53 |
| 3ss | MeO(CH$_2$)$_2$ | piperazinyl-CH$_2$-CONH$_2$ | 4jj, 5a | 21 |
| 3uu | HO(CH$_2$)$_2$ | piperazinyl-CH$_2$-CONH$_2$ | 4jj, 5f | 82 |
| 3vv | HO(CH$_2$)$_2$ | piperazinyl-CH$_2$-CONEt$_2$ | 4ii, 5f | 41 |

2-Methoxyethyl 3-nitro-4-(3-(1-ethoxycarbonyl-4-piperazinylmethyl)-phenylamino)-benzoate 3a. A mixture of 5a (0.94 g; 3.62 mmol), 4a (1.0 g; 3.83 mmol) and triethylamine (0.53 ml; 3.80 mmol) in NMP (10 ml) was heated to 110° C. overnight. The cooled mixture was partitioned between water and ethyl acetate. The phases were separated and the aqueous phase was extracted with ethyl acetate. The combined organic phases were washed with brine, dried over magnesium sulphate and concentrated under reduced pressure. The residue was purified by column-chromatography on silica gel using a mixture of ethyl acetate and petroleum ether (1:1 v/v) as the eluent. Yield: 0.75 g (43%).

The following compound were prepared in analogy with Compound 3a:

2-Methoxyethyl 3-nitro-4-(3-(1-(ethoxy-carbonyl-methyl)-4-piperazinylmethyl)-phenylamino)-benzoate (3b) from 4b and 5a.

2-Methoxyethyl 3-nitro-4-(3-(4-methoxycarbonyl-1-imidazolyl)-phenylamino)-benzoate (3c) from 4c and 5a.

2-Methoxyethyl 3-nitro-4-(3-(1-(benzyloxy-carbonyl-methyl)-4-piperazinyl)-phenylamino)-benzoate (3d) from 4d and 5a.

2-Methoxyethyl 3-nitro-4-(3-(1-methyl-4-piperazinyl)-phenylamino)-benzoate (3e) from 4e and 5a.

2-Methoxyethyl 3-nitro-4-(3-(1-acetyl-4-piperazinyl)-phenylamino)-benzoate (3f) from 4f and 5a.

2-Methoxyethyl 3-nitro-4-(3-(1-methyl-4-piperidyl)-phenylamino)-benzoate (3g) from 4g and 5a.

2-Methoxyethyl 3-nitro-4-(3-(1-acetyl-4-piperidyl)-phenylamino)-benzoate (3h) from 4h and 5a.

2-Methoxyethyl 3-nitro-4-(3-(1-(t-butoxy-carbonyl-methyl)-4-piperazinyl)-phenylamino)-benzoate (3i) from 4i and 5a.

2-Methoxyethyl 3-nitro-4-(3-(1-(1-propoxy-carbonyl-methyl)-4-piperazinyl)-phenylamino)-benzoate (3j) from 4j and 5a.

(N,N-Diethylcarbamoyl)methyl 2-(3-(3-[N-(4-ethoxycarbonyl-3-nitrophenyl)-amino]-phenyl)-4,5-dihydroisoxazol-5-yl)-acetate (3k) from 4k and 5b.

Methyl 3-nitro-4-(3-(1-imidazolylmethyl)-phenylamino)-benzoate (3l) from 4l and 5c.

2-(Methylthio)-ethyl 3-nitro-4-(3-(1-imidazolylmethyl)-phenylamino)-benzoate (3n) from 4l and 5d.

2-(Methylthio)-ethyl 3-nitro-4-(3-(4-methyl-1-piperazinyl)-phenylamino)-benzoate (3o) from 4l and 5d.

2-Methoxyethyl 3-nitro-4-(3-(4-benzyl-1-piperazinyl)-phenylamino)-benzoate (3r) from 4s and 5a.

Methyl 3-nitro-4-(3-(4-(cyanomethyl)-1-piparazinyl)-phenylamino)-benzoate (3s) from 4t and 5c.

2-Methoxyethyl 3-nitro-4-(3-(4-(cyanomethyl)-1-piparazinyl)-phenylamino)-benzoate (3t) from 4t and 5a.

Methyl 3-nitro-4-(3-(4-benzyl-1-piparazinyl)-phenylamino)-benzoate (3u) from 4s and 5c.

2-Methoxyethyl 3-nitro-4-(3-(4-((1-methyl-5-tetrazolyl)methyl)-1-piparazinyl)-phenylamino)-(3w) from 4u and 5a.

2-Methoxyethyl 3-nitro-4-(3-(4-ethyl-1-homopiparazinyl)-phenylamino)-benzoate (3x) from 4v and 5a.

Methyl 3-nitro-4-(3-(4-ethyl-1-homopiparazinyl)-phenylamino)-benzoate (3y) from 4v and 5c.

2-Methoxyethyl 3-nitro-4-(3-(4-ethyl-1-piparazinyl)-phenylamino)-benzoate (3z) from 4v and 5a.

2-Methoxyethyl 3-nitro-4-(3-(4-ethoxycarbonylmethyl-3,5-dimethyl-1-piparazinyl)-phenylamino)-benzoate (3aa) from 4y and 5a.

Methyl 3-nitro-4-(3-(4-ethoxycarbonylmethyl-3,5-dimethyl-1-piparazinyl)-phenylamino)-benzoate (3bb) from 4y and 5c.

2-Hydroxyethyl 3-nitro-4-(3-(4-ethyl-3,5dimethyl-1-piparazinyl)-phenylamino)-benzoate (3dd) from 4aa and 5a.

2-Methoxyethyl 3-nitro-4-(3-(1-ethyl-1,2,5,6-tetrahydropyridin-4-yl)-phenylamino)-benzoate (3ee) from 4bb and 5a.

2-Methoxyethyl 3-nitro-4-(3-(2-oxo-oxazolidin-5-yl)methyl)-phenylamino)-benzoate (3ff) from 4 cc and 5a.

2-Methoxyethyl 3-nitro-4-(3-(4-((5-methyl-3-oxadiazolyl)methyl)-1-piperazinyl)-phenylamino)-benzoate (3gg) from 4dd and 5a.

Methyl 3-nitro-4-(3-(4-boc-piperazin-1-yl)-phenylamino)-benzoate (3hh) from 4ee and 5c.

2-Methoxyethyl 3-nitro-4-(3-(4-boc-piperazin-1-yl)-phenylamino)-benzoate (3ii) from 4ee and 5a.

2-Methoxyethyl 3-nitro-4-(3-(4-boc-3,5-dimethylpiperazin-1-yl)-phenylamino)-benzoate (3kk) from 4ff and 5a.

2-Methoxyethyl 3-nitro-4-(3-(4-(2-oxotetrahydrofuran-3-yl)-1-piperazinyl)-phenylamino)-benzoate (3ll) from 4gg and 5a.

2-Hydroxyethyl 3-nitro-4-(3-(4-methyl-1-piparazinyl)-phenylamino)-benzoate (3nn) from 4e and 5f.

2-Hydroxyethyl 3-nitro-4-(3-(4-methoxycarbonylmethyl-1-piparazinyl)-phenylamino)-benzoate (3oo) from methyl 3-nitro-4-chlorobenzoate and 5f.

2-Hydroxyethyl 3-nitro-4-(3-(4-ethoxycarbonylmethyl-1-piparazinyl)-phenylamino)-benzoate (3 pp) from 4b and 5f.

2-Methoxyethyl 3-nitro-4-(3-(4-(N,N-diethylcarbamoylmethyl)-piperazin-1-yl)-phenylamino)-benzoate (3qq) from 4ii and 5a.

2-Methoxyethyl 3-nitro-4-(3-(4-methoxycarbonylmethyl-1-piparazinyl)-phenylamino)-benzoate (3rr) from methyl 3-nitro-4-chlorobenzoate and 5a.

2-Methoxyethyl 3-nitro-4-(3-(4-(carbamoylmethyl)-piperazin-1-yl)-phenylamino)-benzoate (3ss) from 4jj and 5a.

2-Hydroxyethyl 3-nitro-4-(3-(4-(carbamoylmethyl)-piperazin-1-yl)-phenylamino)-benzoate (3 ft) from 4jj and 5f.

2-Hydroxyethyl 3-nitro-4-(3-(4-(N,N-diethylcarbamoylmethyl)-piperazin-1-yl)-phenylamino)-benzoate (3uu) from 4ii and 5f.

Example 4

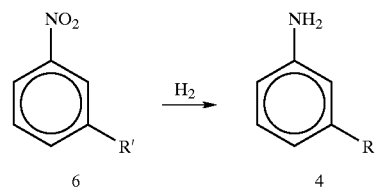

The substituted anilines of Table 4 were prepared by hydrogenation of the corresponding nitro compounds (6) as exemplified by compound 4a below.

TABLE 4

*[Structure: aniline with R substituent at meta position (3-R-aniline with NH₂)]*

| Comp. No. | R | Starting material | R' | Preparation of starting material |
|---|---|---|---|---|
| 4a | [ethyl-piperazine-CO₂Et] | 6a | R | Example 6a |
| 4b | [methyl-piperazine-CH₂CO₂Et] | 6b | R | Example 6b |
| 4c | [1-methyl-imidazole-4-CO₂Me] | 6c | R | Example 6c |
| 4d | [methyl-piperazine-CH₂CO₂Bz] | 6d | R | Example 6d |
| 4e | [methyl-piperazine-NMe] | 6e | R | Example 6e |
| 4f | [methyl-piperazine-NAc] | 6f | R | Example 6f |
| 4g | [4-methyl-piperidine-NMe] | 6g | [4-methyl-tetrahydropyridine-NMe] | Example 6g |
| 4h | [4-methyl-piperidine-NAc] | 6h | [4-methyl-tetrahydropyridine-NAc] | Example 6h |
| 4i | [methyl-piperazine-CH₂CO₂tBu] | 6i | R | Example 6b |
| 4j | [methyl-piperazine-CH₂CO₂iPr] | 6j | R | Example 6b |
| 4k | [3-methyl-isoxazoline-CH₂C(O)OCH₂C(O)NEt₂] | 6k | R | Example 6k |
| 4l | [1-ethyl-imidazole] | 6l | R | Example 6l |

TABLE 4-continued

| Comp. No. | R | Starting material | R' | Preparation of starting material |
|---|---|---|---|---|
| 4m | ethyl 2-(4-ethylpiperazin-1-yl)acetate group | 6m | R | Example 6m |
| 4n | ethyl 2-(4-methylpiperidin-1-yl)acetate group | 6n | ethyl 2-(4-methyl-3,6-dihydro-2H-pyridin-1-yl)acetate | Example 6n |
| 4o | ethyl 4-ethylpiperazine-1-carboxylate group | 6o | R | Example 6o |
| 4p | ethyl 4-methylpiperazine-1-carboxylate group | 6p | R | Example 6p |
| 4q | 2-(4-acetylpiperazin-1-yl)ethyl carboxylate group | 6q | R | Example 6q |
| 4r | (1-methylpyrrolidin-2-yl)methyl carboxylate group | 6r | R | Example 6r |
| 4s | 1-benzyl-4-methylpiperazine group | 6s | R | Example 6b |
| 4t | 2-(4-methylpiperazin-1-yl)acetonitrile group | 6t | R | Example 6b |
| 4u | 1-methyl-4-((1-methyl-1H-tetrazol-5-yl)methyl)piperazine group | 6u | R | Example 6u |
| 4v | 1-ethyl-4-methyl-1,4-diazepane group | 6v | R | Example 6b |
| 4x | 1-ethyl-4-methylpiperazine group | 6x | R | Example 6b |

TABLE 4-continued
| Comp. No. | R | Starting material | R' | Preparation of starting material |
|---|---|---|---|---|
| 4y | 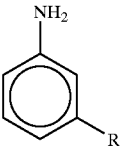 | 6y | R | Example 6b |
| 4z | 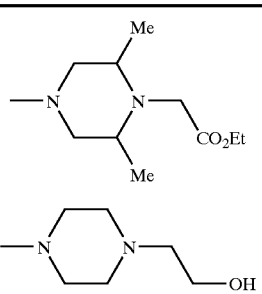 | 6z | R | Example 6b |
| 4aa | 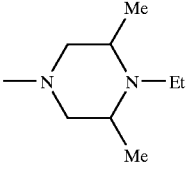 | 6aa | R | Example 6b |
| 4bb | 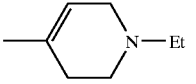 | 6bb | R | Example 6g |
| 4cc | 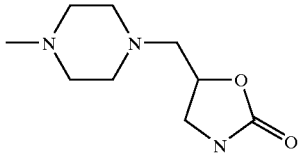 | 6cc | R | Example 6b |
| 4dd | 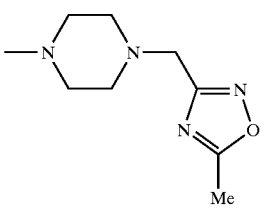 | 6dd | R | Example 6b |
| 4ee | 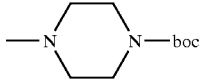 | 6ee | R | Example 6b |
| 4ff | 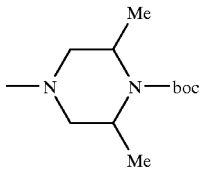 | 6ff | R | Example 6b |
| 4gg | 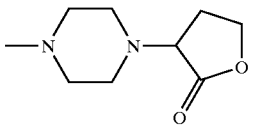 | 6gg | R | Example 6b |

TABLE 4-continued

Structure: aniline with NH₂ at one position and R at the 3-position on the benzene ring.

| Comp. No. | R | Starting material | R' | Preparation of starting material |
|---|---|---|---|---|
| 4ii | piperazine-N-CH₂-CONEt₂ (N-methyl on other nitrogen) | 6ii | R | Example 6b |
| 4jj | piperazine-N-CH₂-CONH₂ (N-methyl on other nitrogen) | 6jj | R | Example 6b |

1-Ethoxycarbonyl-4-(3-aminobenzyl)-piperazine 4a. To a solution of 6a (2.2 g; 7.5 mmol) in abs. ethanol (50 ml) was added palladium catalyst (100 mg, 5% Pd on activated carbon) and the mixture was hydrogenated at ambient pressure until the hydrogen uptake had ceased. Filtration through celite and evaporation of solvent left 4a, quantitatively.

The following compound were prepared in analogy with Compound 4a:

Ethyl 2-(4-(3-aminophenyl)-1-piperazinyl)-acetate (4b) from 6b.

Methyl 1-(3-aminophenyl)-4-imidazolecarboxylate (4c) from 6c.

Benzyl 2-(4-(3-aminophenyl)-1-piperazinyl)-acetate (4d) from 6d. PtO₂ was used as the catalyst.

3-(4-Methyl-1-piperazinyl)-aniline (4e) from 6e.

3-(4-Acetyl-1-piperazinyl)-aniline (4f) from 6f.

3-(1-Methyl-4-piperidyl)-aniline (4g) from 6g.

3-(1-Acetyl-4-piperidyl)-aniline (4h) from 6h.

t-Butyl 2-(4-(3-aminophenyl)-1-piperazinyl)-acetate (4i) from 6i.

i-Propyl 2-(4-(3-aminophenyl)-1-piperazinyl)-acetate (4j) from 6j.

(N,N-Diethylcarbamoyl)-methyl 2-(3-(3-aminophenyl)-4,5-dihydroisoxazol-5-yl)-acetate (4k) from 6k.

1-[(3-aminophenyl)-methyl]-imidazole (4l) from 6l.

Ethyl 2-(4-[(3-aminophenyl)-methyl]-1-piperazinyl)-acetate (4m) from 6m.

Ethyl 2-(4-(3-aminophenyl)-1-piperidyl)-acetate (4n) from 6n.

Ethyl 2-(4-(3-aminophenyl)-methyl)-1-piperidyl)-acetate (4o) from 6o.

Ethyl 2-(4-(3-aminophenyl)-1-piperazinyl)-acetate (4p) from 6p.

2-(4-Acetyl-1-pierazinyl)-ethyl 3-aminobenzoate (4q) from 6q. THF was used as solvent.

1-Methyl-2-pyrrolidylmethyl 3-aminobenzoate (4r) from 6r. THF was used as solvent.

3-(4-benzyl-1-piperazinyl)-aniline (4s) from 6s. PtO₂ was used as the catalyst. 2-(4-(3-aminophenyl)-1-piperazinyl)-acetonitril (4t) from 6t.

3-(4-((1-methyltetrazol-5-yl)methyl)-1-piperazinyl)-aniline (4u) from 6u. PtO₂ was used as the catalyst.

3-(4-ethyl-1-homopiperazinyl)-aniline (4v) from 6v.

3-(4-ethyl-1-piperazinyl)-aniline (4x) from 6x.

3-(4-ethoxycarbonylmethyl-3,5-dimethyl-1-piperazinyl)-aniline (4y) from 6y.

3-(4-(2-hydroxyethyl)-1-piperazinyl)-aniline (4z) from 6z.

3-(4-ethyl-3,5-dimethyl-1-piperazinyl)-aniline (4aa) from 6aa.

3-(4-(2-oxo-oxazolidin-5-yl)methyl)-1-Diperazinyl)-aniline (4 cc) from 6 cc.

3-(4-(5-methyloxadiazol-3-yl)methyl)-1-piperazinyl)-aniline (4dd) from 6dd.

3-(4-boc-1-piperazinyl)-aniline (4ee) from 6ee.

3-(4-boc-3,5-dimethyl-1-piperazinyl)-aniline (4ff) from 6ff.

3-(4-(2-oxotetrahydrofuran-3-yl)-1-piperazinyl)-aniline (4gg) from 6gg.

3-(4-methoxycarbonylmethyl-1-piperazinyl)-aniline (4hh) as described in WO 98/17651.

3-(4-((N,N-diethylcarbamoyl)methyl)-1-piperazinyl)-aniline (4ii) from 6ii.

3-(4-(carbamoylmethyl)-1-piperazinyl)-aniline (4jj) from 6jj.

Example 4a 3-(4-(1-ethyl-1,2,5,6-tetrahydropyridin-4-yl)-1-piperazinyl)-aniline (4bb). A mixture of 6bb (Example 6g) (0.85 g; 3.66 mmol), sodium sulfide nonahydrate (2.64 g; 11.0 mmol) and ammonium chloride (0.58 g; 10.8 mmol) in abs. ethanol (25 ml) was heated to reflux for 4 hours. The cooled mixture was poured into ice-water and extracted with dichloromethane. The extract was dried over magnesium sulphate, filtered and evaporated to leave 4bb. Yield: 0.60 g (81%).

Example 5

Scheme: benzene ring with HOOC, NO₂, and Cl substituents → 1) SOCl₂ 2) MeOCH₂CH₂OH -continued

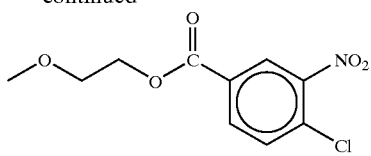

2-Methoxyethyl 4-chloro-3-nitrobenzoate 5a. A mixture of 4-chloro-3-nitrobenzoic acid (10.0 g; 49.6 mmol) and thionylchloride (50 ml) was heated to reflux overnight. The excess of thionylchloride was removed by evaporation and 2-methoxyethanol (50 ml) was added. The resulting mixture was stirred at 80° C. for 4 hours. The cooled solution was diluted with water (500 ml) and extracted with ethyl acetate (2×100 ml). The organic extract was dried over magnesium sulphate and concentrated under reduced pressure. Trituration of the residue with petroleum ether left 5a (8.0 g; 62%) as a low melting solid (Mp. 33–35° C.).

The following compound were prepared in analogy with Compound 5a:
Ethyl 4-chloro-3-nitrobenzoate (5b);
Methyl 4-chloro-3-nitrobenzoate (5c);
2-(Methylthio)ethyl 4-chloro-3-nitrobenzoate (5d);
2-(N,N-dimethylamino)ethyl 4-chloro-3-nitrobenzoate (5e); and
2-Hydroxyethyl 4-chloro-3-nitrobenzoate (6f).

Example 6a

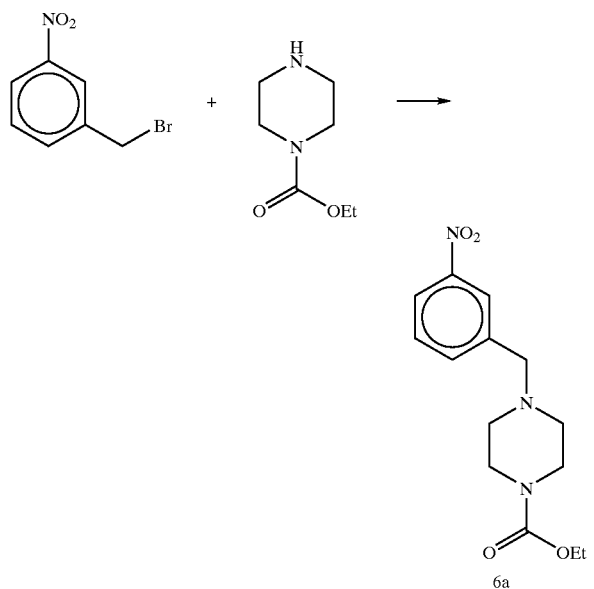

1-Ethoxycarbonyl 4-(3-nitrobenzyl)-piperazine (6a). To a solution of 3-nitrobenzylbromide (2.2 g; 10.0 mmol) in NMP (5 ml) was added ethyl piperazine-1-carboxylate dropwise with stirring. At the end of the addition the temperature had reached 35° C. Triethylamine (1.39 ml) was added causing the temperature to rise to 40° C. The mixture was stirred for additionally 30 min. prior to dilution with diethyl ether (25 ml). The mixture was filtered and the filtrate was washed with water, dried over magnesium sulphate and concentrated under reduced pressure. The concentrate was suspended in diethyl ether and filtered. The filtrate was diluted with ethyl acetate and extracted with diluted hydrochloric acid. The aqueous phase was rendered alkaline by addition of saturated aqueous sodium bicarbonate and extracted with ethyl acetate. The organic phase was dried over magnesium sulphate and evaporated to dryness to leave 6a (1.72 g; 59%).

Example 6b

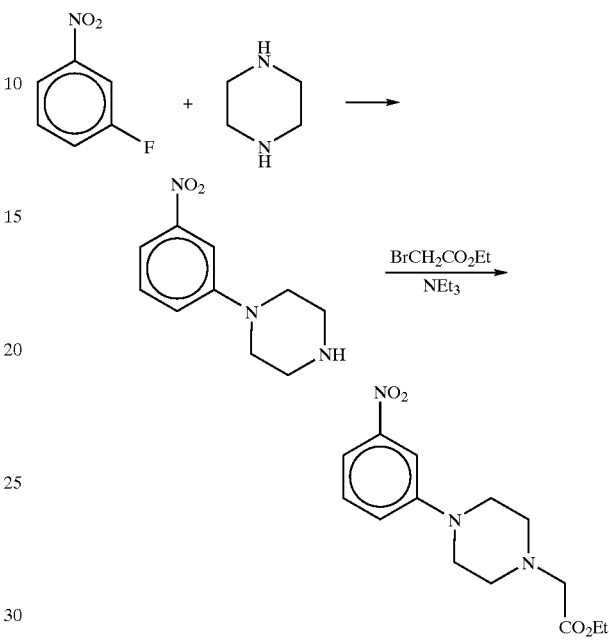

1-(3-Nitrophenyl)-piperazine. A suspension of 3-fluoronitrobenzene (23 ml; 0.21 mol) and piperazine (55.5 g; 0.64 mol) in anhydrous NMP (30 ml) was heated to 70° C. for five days. The cooled mixture was diluted with water (250 ml) and extracted with dichloromethane. The combined extracts were dried over magnesium sulphate and concentrated under reduced pressure. The residue was purified by column-chromatography on silica gel eluting subsequently with mixtures of ethyl acetate and methanol (4:1 v/v) and (1:1 v/v) to leave the desired product as oily crystals (30.7 g; 71%).

Ethyl 2-(4-(3-nitrophenyl)-1-piperazinyl)-acetate (6b). To a solution of 1-(3-nitrophenyl)piperazine (12.0 g; 58 mmol) in DMF (60 ml) was added sodium hydride (2.55 g; 64 mmol, 60% dispersion in mineral oil) in portions over 30 min. The mixture was kept under nitrogen. Ethyl 2-bromoacetate (7.1 ml; 64 mmol) was added, the mixture was stirred at ambient temperature for one hour and then poured into water (250 ml). The oily precipitate was filtered off, re-dissolved in ethyl acetate and washed with water. The organic phase was dried over magnesium sulphate and evaporated to dryness to leave 6b (11.0 g; 65%).

The following compound were prepared in analogy with Compound 6b:
Isopropyl 2-(4-(3-nitrophenyl)-1-piperazinyl)-acetate (6j) from 1-(3-nitrophenyl)piperazine and isopropyl 2-bromoacetate.
t-Butyl 2-(4-(3-nitrophenyl)-1-piperazinyl)-acetate (6i) from 1-(3-nitrophenyl)piperazine and t-butyl 2-bromoacetate.
1-(3-Nitrophenyl)-4-benzylpiperazine (6s) from 1-(3-nitrophenyl)piperazine and benzylchloride.
2-(1-(3-Nitrophenyl)-4-piperazinyl)-acetonitrile (6t) from 1-(3-nitrophenyl)piperazine and 2-bromoacetonitrile.

1-(3-Nitrophenyl)-4-ethylhomopiperazine (6v) from 1-(3-nitrophenyl)homopiperazine (prepared analogously to 1-(3-nitrophenyl)piperazine) and iodoethane.

1-(3-Nitrophenyl)-4-methylpiperazine (6x) from 1-(3-nitrophenyl)piperazine and iodomethane.

1-(3-Nitrophenyl)-4-ethoxycarbonylmethyl-3,5-dimethylpiperazine (6y) from 1-(3-nitrophenyl)-2,6-dimethylpiperazine (prepared analogously to 1-(3-nitrophenyl)piperazine) and ethyl 2-bromoacetate.

1-(3-Nitrophenyl)-4-(2-hydroxyethyl)-piperazine (6z) from 1-(3-nitrophenyl)piperazine and 2-bromoethanol.

1-(3-Nitrophenyl)-4-ethyl-3,5-dimethylpiperazine (6aa) from 1-(3-nitrophenyl)-2,6-dimethylpiperazine (prepared analogously to 1-(3-nitrophenyl)-piperazine) and iodoethane.

1-(3-Nitrophenyl)-4-((2-oxo-oxazolidin-5-71)-methyl)-piperazine (6 cc) from 1-(3-nitrophenyl)-piperazine and 5-chloromethyl-2-oxazolidinone.

1-(3-Nitrophenyl)-4-((5-methyloxadiazol-3-yl)-methyl)-piperazine (6dd) from 1-(3-nitrophenyl)piperazine and 3-chloromethyl-5-methyloxadizole.

1-(3-Nitrophenyl)-4-boc-piperazine (6ee) from 1-(3-nitrophenyl)-piperazine and Boc-anhydride.

1-(3-Nitrophenyl)-4-boc-3,5-dimethylpiperazine (6ff) from 1-(3-nitrophenyl)-2,6-dimethylpiperazine (prepared analogously to 1-(3-nitrophenyl)-piperazine) and Boc-anhydride.

1-(3-Nitrophenyl)-4-(2-oxotetrahydrofuran-3-yl)-piperazine (6gg) from 1-(3-nitrophenyl)-piperazine and a-bromobutyrolactone.

1-(3-Nitrophenyl)-4-((N,N-diethylarbamoyl)-methyl)-piperazine (6ii) from 1-(3-nitrophenyl)-piperazine and 2-chloro-N,N-diethylacetamide.

1-(3-Nitrophenyl)-4-(carbamoylmethyl)-piperazine (6jj) from 1-(3-nitrophenyl)-piperazine and 2-chloroacetamide.

Example 6c

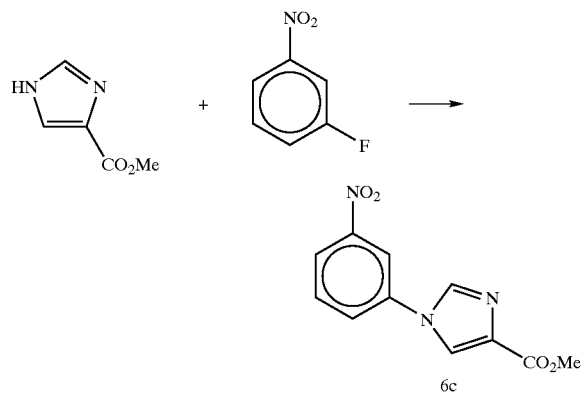

Methyl 1-(3-nitrophenyl)-imidazole-4-carboxylate (6c). A mixture of 3-fluoronitrobenzene (1.78 ml; 16.7 mmol), methyl imidazole-4-carboxylate and potassium carbonate (2.3 g; 16.7 mmol) in 10 ml NMP was heated to 120° C. in a nitrogen atmosphere overnight. The cooled mixture was poured into water (100 ml), the precipitate was filtered off, washed with water and dried to yield 6c (2.38 g; 58%).

Example 6d

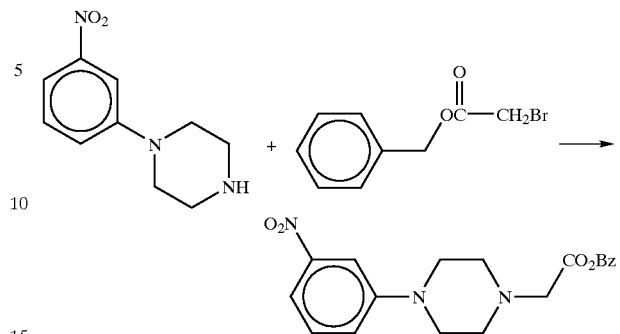

Benzyl 2-(4-(3-nitrophenyl)-1-piperazinyl)-acetate (6d). To a solution of 1-(3-nitrophenyl)piperazine (Example 6a) (10.0 g; 48.3 mmol) in anhydrous DMF (50 ml) was added sodium hydride (2.12 g, 60% dispersion in mineral oil; 53.1 mmol) in small portions. The mixture was stirred and benzyl 2-bromoacetate was added. The addition was extremely exothermic. The reaction mixture was left with stirring at ambient temperature overnight. The mixture was poured into water (200 ml) and extracted with ethyl acetate. The combined extracts were dried over magnesium sulphate and concentrated under reduced pressure. The residue was purified by column-chromatography on silica gel using ethyl acetate as the eluent to yield 6c (14.4 g; 84%).

Example 6e

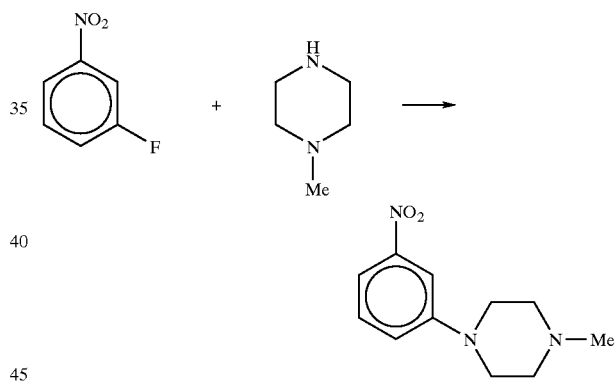

1-(3-Nitrophenyl)-4-methylpiperazine (6e). A mixture of 3-fluoronitrobenzene (20 ml; 0.19 mol) and 1-methylpiperazine (40 ml; 0.36 mol) was heated to 120° C. for a week. The cooled mixture was purified by column-chromatography on silica gel using a mixture of ethyl acetate and methanol (9:1 v/1) as the eluent. Yield: 33 g (79%).

Example 6f

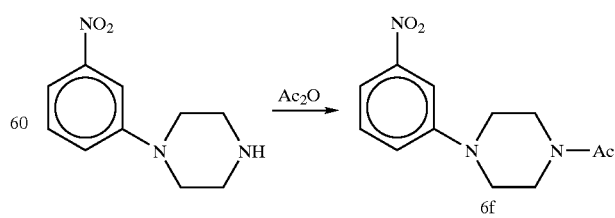

1-Acetyl-4-(3-nitrophenyl)-piperazine (6f). A mixture of 1-(3-nitrophenyl)piperazine (Example 6a) (33.0 g; 0.16 mol)

and acetic anhydride (130 ml) was stirred at ambient temperature overnight. The excess of acetic anhydride was removed by evaporation and saturated aqueous sodium carbonate was added to the residue with stirring. The precipitate was filtered off, washed with water and dried to leave 6f (39 g; 98%).

Example 6g

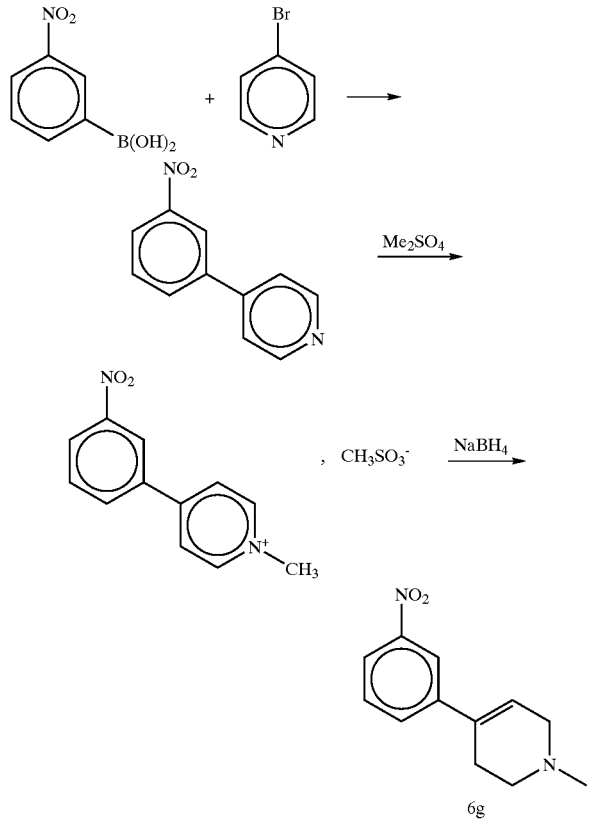

4-(3-Nitrophenyl)-pyridine. A mixture of 4-bromopyridine, hydrochloride (8.03; 41.3 mmol), 3-nitrophenylboronic acid (6.85 g; 41.0 mmol), potassium carbonate (34.2 g; 0.25 mol), 1,3-propandiol (14.9 ml; 0.21 mol) and tetrakis(triphenylphosphine)palladium (0.2 g) in a mixture of dimethoxyethane (80 ml) and water (40 ml) was stirred at 80° C. in a nitrogen atmosphere overnight. The cooled mixture was diluted with ethyl acetate and filtered through celite. The filtrate was evaporated to dryness and water was added to the residue. Vigorously stirring caused the product to precipitate. The product was filtered off, washed with water, dried and subsequently washed with petroleum ether. Yield: 8.15 g (99%).

1-Methyl-4-(3-nitrophenyl)-pyridinium monomethylsulphate. A mixture of 4-(3-nitrophenyl)pyridine (4.0 g; 20 mmol) and dimethylsulphate (10 ml) was heated to 100° C. for five days. The cooled mixture wad diluted with diethyl ether (50 ml) and stirred thoroughly. The mixture was decanted and the oily bottom layer was washed additionally three times with diethyl ether and once with ethanol to leave the crystalline product (2.9 g; 47%).

1-Methyl-4-(3nitrophenyl)-1,2,5,6-tetrahydropyridine (6g). To a suspension of 1-methyl-4-(3-nitrophenyl) pyridinium monomethylsulphate (2.8 g; 9.03 mmol) in methanol (50 ml) was added sodium borohydride (0.68 g; 18.0 mmol) in portions over 30 min. Following the addition the mixture was stirred at ambient temperature overnight. The mixture was diluted with water (200 ml) and extracted with ethyl acetate (2×100 ml). The combined extracts were washed with brine, dried over magnesium sulphate and evaporated to dryness. Trituration of the residue with diethyl ether left the crystalline product (1.7 g; 86%).

1-Ethyl-4-(3-nitrophenyl)-1,2,5,6-tetrahydropyridine (6bb) was prepared analogously by alkylation with iodoethane.

Example 6h

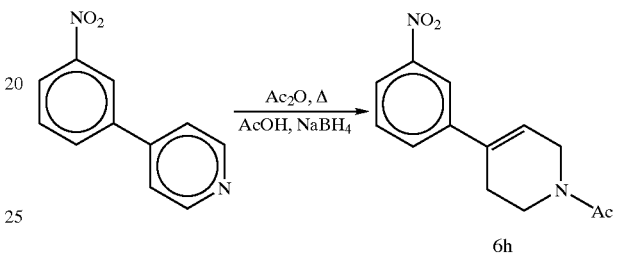

1-Acetyl-4-(3-nitrophenyl)-1,2,5,6-tetrahydropyridine (6h). To a mixture of 4-(3-nitrophenyl)pyridine (Example 6g) (4.0 g; 20.0 mmol) and acetic anhydride (20 ml) in glacial acetic acid (30 ml) was added sodium borohydride (1.51 g; 40.0 mmol) in portions over one hour. The resulting mixture was stirred at ambient temperature for five days and then poured into ice-water. The mixture was extracted with ethyl acetate, the organic phase was washed with water, dried over magnesium sulphate and concentrated under reduced pressure. The residue was eluted through silica gel with ethyl acetate to yield 6h (1.29 g; 26%).

Example 6k

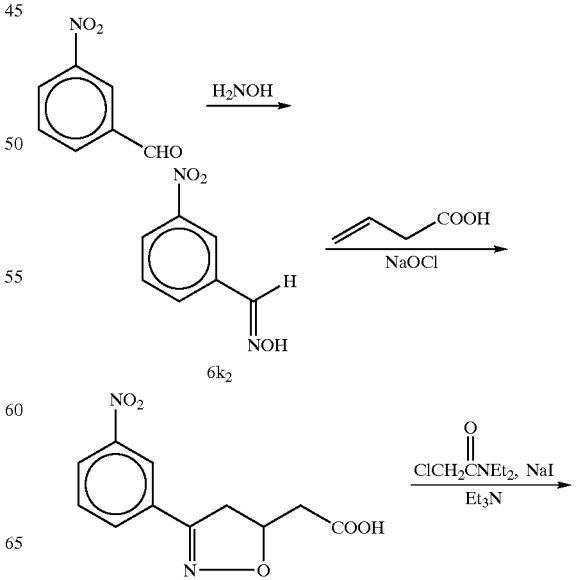

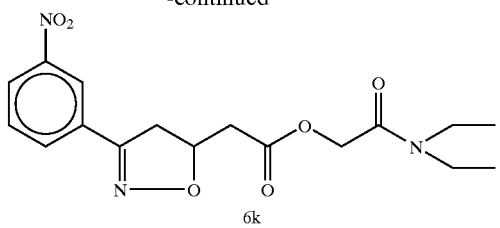

3-Nitrobenzaldehyde oxime (6k$_2$). To a solution of 3-nitrobenzaldehyde (5.0 g; 33.1 mmol) in abs. ethanol (40 ml) was added hydroxylamine, hydrochloride (3.45 g; 49.6 mmol) and the resulting suspension was heated to reflux overnight. The cooled mixture was poured into water (100 ml) and the product was filtered off and dried. Yield: 4.5 g (82%).

2-(3-(3-Nitrophenyl)-4,5-dihydroisoxazol-5-yl)-acetic acid. To a solution of 6k$_2$ (3.1 g; 18.8 mmol) in THF (30 ml) was added vinylacetic acid (3.41 ml; 56.4 mmol). An aqueous solution of sodium hypochlorite (47 ml; 0.2 M) was added dropwise keeping the temperature between 25–30° C. Following the addition the mixture was stirred at ambient temperature overnight. pH was adjusted to 4 by addition of aqueous citric acid and the mixture was extracted thrice with diethyl ether. The combined extracts were dried over sodium sulphate and concentrated under reduced pressure. The concentrate was purified by column-chromatography on silica gel using a mixture of ethyl acetate and methanol (9:1 v/v) as the eluent. Yield: 4.7 g (98%).

N,N-Diethylcarbamoylmethyl 2-(3-(3-nitrophenyl)-4,5-dihydroisoxazole-5-yl)-acetate (6k). A mixture of 6k$_2$ (4.6 g; 18.4 mmol), 2-chloro N,N-diethylacetamide (2.53 ml; 18.4 mmol), triethylamine (5.1 ml; 36.6 mmol) and a catalytic amount of sodium iodide in anhydrous DMF (25 ml) was stirred at ambient temperature overnight. The solvent was removed by evaporation under reduced pressure and the residue was partitioned between water and ethyl acetate. The organic phase was dried over sodium sulphate and concentrated under reduced pressure.

Example 6l

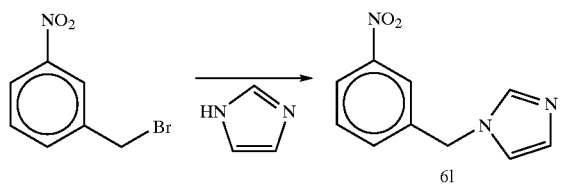

1-(3-Nitrobenzyl)-imidazole (6k). A mixture of 3-nitrobenzylbromide (10 g; 46.3 mmol) and imidazole (6.3 g; 92.5 mmol) in NMP (10 ml) was stirred at 80° C. overnight. The cooled mixture was poured into ice-water and rendered alkaline by addition of aqueous sodium hydroxide (4 M). The precipitate was filtered off, washed with water and dried to yield 6l (6.9 g; 73%).

Example 6m

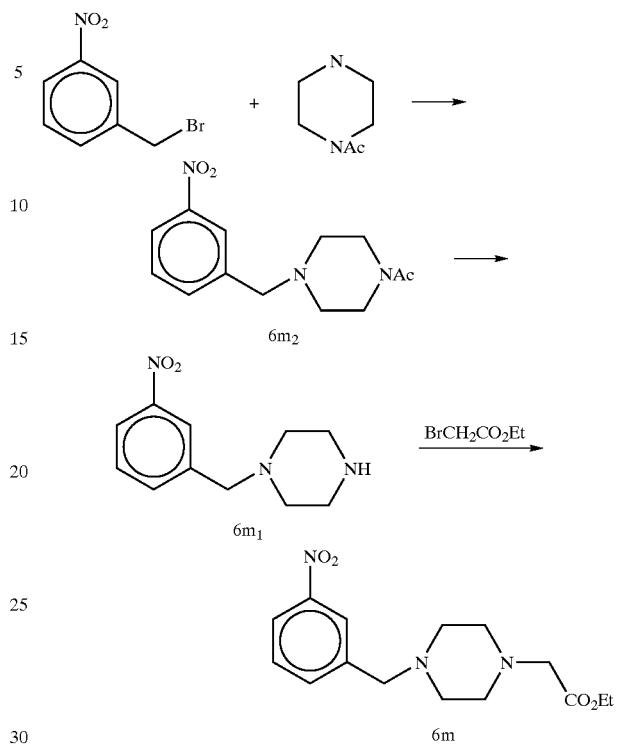

1-Acetyl-4-(3-nitrobenzyl)-piperazine (6m$_2$). To a solution of 1-acetylpiperazine (5.0 g; 39.0 mmol) in THF (50 ml) was added triethylamine (5.6 ml; 39.0 mmol) and 3-nitrobenzylbromide (8.4 g; 39.0 mmol). The mixture was stirred at ambient temperature for 1 hour and the solvent was removed by evaporation. The residue was partitioned between water and ethyl acetate. The organic phase was dried over sodium sulphate and evaporated under reduced pressure to leave 6m$_2$, quantitatively.

1-(3-Nitrobenzyl)-piperazine (6m$_1$). To a solution of 6m$_2$ (10.2 g; 39.0 mmol) in dimethoxyethane (100 ml) was added aqueous sodium hydroxide (120 ml; 1 M) and the mixture heated to reflux overnight. The mixture was evaporated to dryness and the residue was extracted with a mixture of ethanol and dichloromethane (2:1 v/v). The extract was evaporated to dryness to leave 6m$_1$ (6.1 g; 71%).

Ethyl 2-(4-(3-nitrobenzyl)-1-piperazinyl)-acetate (6m). To a solution of 6m$_1$ (2.5 g; 11.3 mmol) in anhydrous DMF (20 ml) was added sodium hydride (13.6 mmol; 0.54 g 60% dispersion in mineral oil) and ethyl 2-bromoacetate (1.25 ml; 11.3 mmol). The exothermic reaction was completed in 15 min. The mixture was poured into ice-water and extracted with ethyl acetate. The organic extract was dried over sodium sulphate and evaporated to dryness to leave 6m quantitatively,

Example 6n

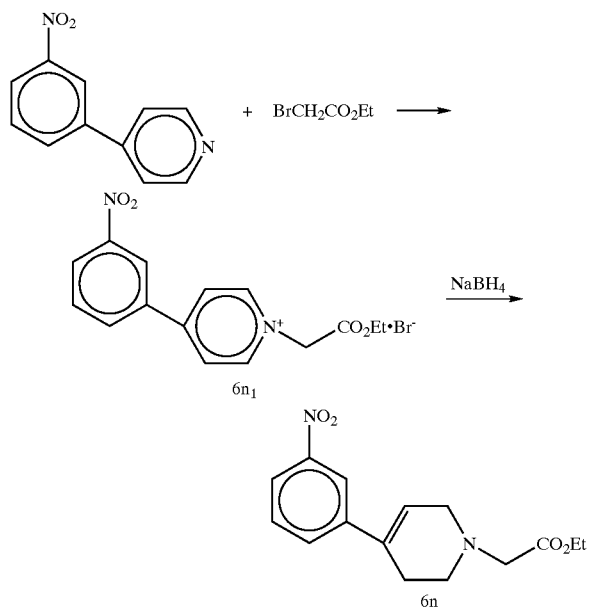

1-(Ethoxy-carbonyl-methyl)-4-(3-nitrophenyl)-pyridinium bromide (6n₁). A mixture of 4-(3-nitrophenyl) pyridine (2.25 g; 11.3 mmol) and ethyl 2-bromoacetate (1.5 ml; 13.5 mmol) in THF (10 ml) was heated to reflux overnight. The cooled mixture was filtered and the crystalline product was washed with THF and dried to leave 6n₁ (3.49 g; 84%).

1-(Ethoxy-carbonyl-methyl)-4-(3-nitrophenyl)-1,2,5,6-tetrahydropyridine (6n). To a suspension of 6n₁ (2.90 g; 7.88 mmol) in abs. ethanol (50 ml) was added sodium borohydride (0.60 g; 15.9 mmol) in portions over 1 hour. The mixture was stirred at ambient temperature for two days, poured into ice-water and extracted with ethyl acetate. The extract was dried over sodium sulphate, concentrated and eluted through silica gel with ethyl acetate to yield 6n (1.65 g; 72%).

Example 6o

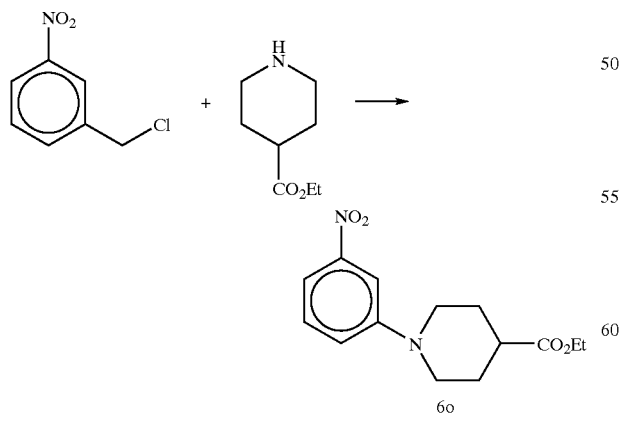

Ethyl 1-(3-nitrophenyl)-piperidine-4-carboxylate (6o). To a solution of 3-nitrobenzylchloride (2.0 g; 11.7 mmol) and triethylamine (1.65 ml; 11.7 mmol) in NMP (3 ml) was added ethyl isonipecotate (1.8 ml; 11.7 mmol). The mixture was heated to 80° C. overnight. The cooled mixture was poured into water and extracted with ethyl acetate. The organic extract was washed with brine, dried over sodium sulphate and evaporated to dryness to leave 6o, quantitatively.

Example 6p

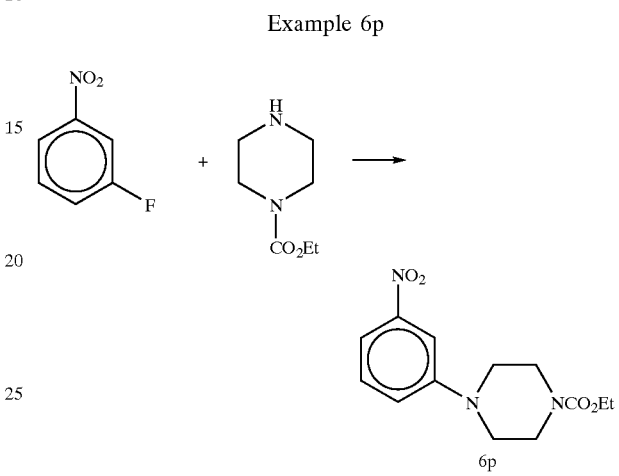

1-Ethoxycarbonyl-4-(3-nitrophenyl)-piperazine (6p). To a solution of 3-fluoro-1-nitrobenzene (3.37 ml; 31.6 mmol) in NMP (5 ml) was added triethylamine (4.38 ml; 31.6 mmol) and ethyl 1-piperazinecarboxylate (4.63 ml; 31.6 mmol) and the mixture was heated to 120° C. for five days. The cooled mixture was poured into ice-water and a small volume of ethanol was added. Vigorous stirring caused the product to precipitate. The product was filtered off, washed with petroleum ether and dried to leave 6p (3.34 g; 38%).

Example 6q

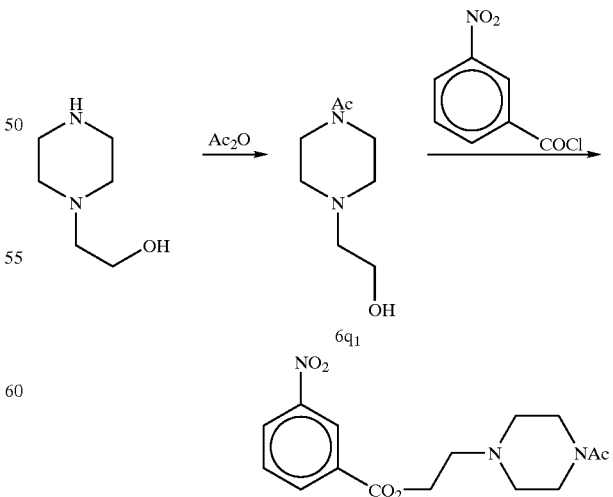

1-Acetyl-4-(2-hydroxyethyl)-piperazine (6q₁). To a solution of 1-(2-hydroxyethyl)piperazine (5.5 ml; 42.3 mmol) in toluene (50 ml) was added acetic anhydride (4.0 ml; 42.4 mmol). The mixture was heated to 80° C. overnight. The solvent was removed under reduced pressure and the residue was washed several times with a mixture of diethyl ether and petroleum ether (1:1 v/v) to leave 6q₁ as an oil (5.2 g; 72%).

2-(1-Acetyl-4-piperazinyl)-ethyl 3-nitrobenzoate (6q). To a solution of 3-nitrobenzoyl chloride (2.5 g; 13.5 mmol) in a mixture of THF (25 ml) and DMF (5 ml) was added triethylamine (1.87 ml; 13.5 mmol), a catalytic amount of 4-(N,N-dimethylamino)pyridine and 6q₁ (2.32 g; 13.5 mmol). The mixture was heated to 80° C. for 2 hours whereafter the solvent was removed under reduced pressure. The residue was re-dissolved in dichloromethane and extracted with diluted hydrochloride acid (4 M). The aqueous phase was rendered alkaline by addition of aqueous sodium hydroxide (4 M) and extracted with dichloromethane. This extract was dried over sodium sulphate and concentrated under reduced pressure. The concentrate was purified by column-chromatography on silica gel using a mixture of dichloromethane, methanol and aqueous ammonia (90:10:1 v/v/v) as the eluent. Yield: 1.0 g (23%).

Example 6r

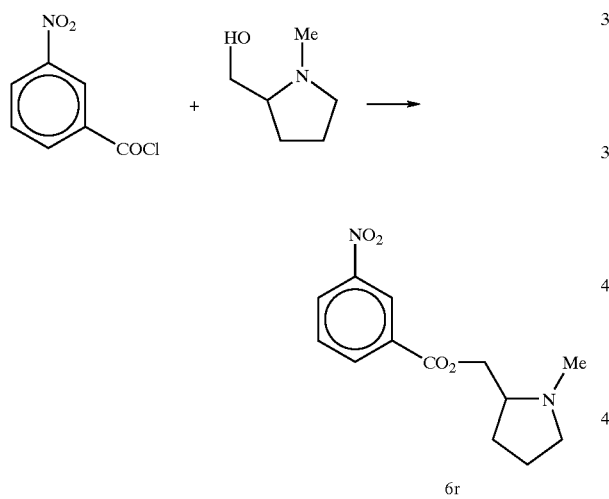

6r (1-Methyl-2-pyrrolidyl)-methyl 3-nitrobenzoate (6r). To a solution of 3-nitrobenzoylchloride (2.5 g; 13.5 mmol) in THF (25 ml) was added triethylamine (1.87 ml; 13.5 mmol), a catalytic amount of 4-(N,N-dimethylamino)pyridine and (S)-(−)-1-methyl-2-pyrrolidinemethanol (1.61 ml; 13.5 mmol). The mixture was heated to reflux for 1.5 hours and left with stirring at ambient temperature overnight. The solvent was removed by evaporation and the residue was partitioned between dichloromethane and diluted hydrochloric acid (4 M). The aqueous phase was rendered alkaline by addition of aqueous sodium hydroxide (4 M) and extracted with dichloromethane. The organic extract was dried over sodium sulphate and evaporated to leave 6r (2.8 g; 78%).

The concentrate was purified by column-chromatography on silica gel using a mixture of ethyl acetate and petroleum ether as the eluent (9:1 v/v). Yield: 2.6 g (38%).

Example 6u 1-(3-Nitrophenyl)-4-((1-methyl-5-tetrazolyl)-methyl)-piperazine (6u). A solution of 6t (2.40 g; 10.0 mmol), sodium azide (1.43 g; 22.0 mmol) and ammonium chloride (0.64 g; 12.0 mmol) in DMF (25 ml) was heated to 120° C. over night. The cooled mixture was poured into ice-water and the precipitate was filtered off, washed with water and air-dried to leave a tetrazole (2.03 g).

This intermediary product was suspended in DMF (25 ml) in a nitrogen atmosphere and sodium hydride (0.28 g, 7.0 mmol) was added. When the evolution of hydrogen had ceased iodo-methane (0.44 ml; 7.1 mmol) was added and the mixture was stirred at ambient temperature for 4 hours. The mixture was diluted with four volumes of water and extracted with ethyl acetate. The extract was dried over magnesium sulphate and evaporated to dryness. The residue was trituated with a mixture of diethyl ether and petroleum ether (1:1 v/v) to leave 6u. Yield: 0.95 g.

Example 7

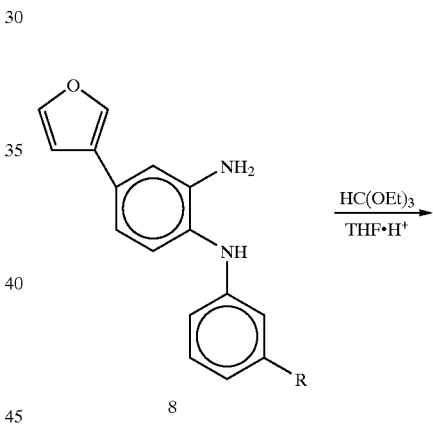

The furanyl substituted benzimidazoles of Table 5 were all prepared according to the above scheme as exemplified for compound 7a below.

TABLE 5
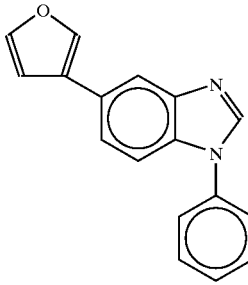
| Comp. No. | R | Mp (° C.) | Yield (%) | Starting material | Salt |
|---|---|---|---|---|---|
| 7a | 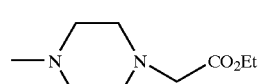 | 248–250 | 100 | 8a | HCl |
| 7b | 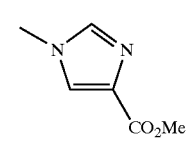 | 113–114.5 | 83 | 8b | |
| 7c | 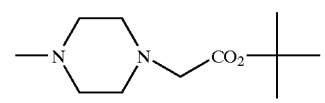 | 221–223 | 100 | 8c | |
| 7d | 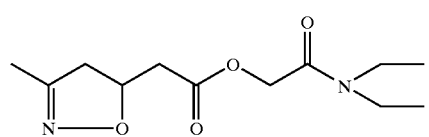 | 131–132 | 37 | 8d | |
| 7e | 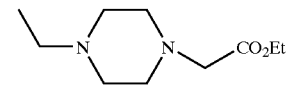 | oil | 77 | 8e | |
| 7f | 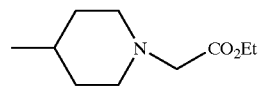 | oil | 47 | 8f | |
| 7g |  | 114–115 | 29 | 8g | |
| 7h | 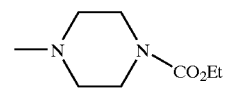 | oil | 82 | 8h | |
| 7i | 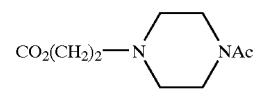 | 131–132 | 48 | 8i | |
| 7j | CO$_2$(CH$_2$)$_2$—N⌒NAc | 167–168 | 78 | 8j | HCl |
| 7k | 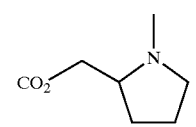 | 198–200 | 38 | 8k | HCl |

5-(3-Furanyl)-1-(3-((4-ethoxycarbonyl-1-piperazinyl)-methyl)-phenyl)-benzimidazole (7a). To a solution of 8a (0.13 g; 0.31 mmol) in THF was added triethyl orthoformiate (0.1 ml; 0.62 mmol) and a catalytic amount of p-toluenesulfonic acid. The mixture was heated to 80° C. for 30 min. The cooled mixture was diluted with ethyl acetate and washed with aqueous sodium hydroxide and water, successively. The organic phase was dried over sodium sulphate and concentrated to a small volume. The product precipitated as the hydrochloride upon addition of ethereal hydrogen chloride. Filtration left the product, quantitatively. Mp. 248–250° C.

The following compound were prepared in analogy with Compound 7a:

5-(3-Furanyl)-1-(3-(1-(ethoxy-carbonyl-methyl)-4-piperazinyl)-phenyl)-benzimidazole (7b) from 8b. The product was purified on silica gel using a mixture of ethyl acetate and ethanol (9:1 v/v) and was isolated as the free base. Mp. 113–114.5° C.

5-(3-Furanyl)-1-(3-(4-methoxycarbonyl-1-imidazolyl)-phenyl)-benzimidazole (7c) from 8c. Mp. 221–223° C.

5-(3-Furanyl)-1-(3-(4-t-butoxycarbonylmethyl-1-piperazinyl)-phenyl)-benzimidazole (7d) from 8d. The product was purified on silica gel using ethyl acetate as the eluent and was isolated as the free base. Mp. 131–132° C.

N,N-Diethylcarbamoylmethyl 2-(3-(3-(5-(3-furanyl)-1-benzimidazolyl)-phenyl)-4,5-dihydroisoxazole-5-yl)-acetate (7e) from 8e. The product was purified on silica gel using ethyl acetate as the eluent and was isolated as the free base.

5-(3-Furanyl)-1-(3-(1-ethoxycarbonylmethyl-4-piperazinylmethyl)-phenyl)-benzimidazole (7f) from 8f. The product was purified on silica gel using a mixture of ethyl acetate and ethanol (9:1 v/v) as the eluent and was isolated as the free base.

5-(3-Furanyl)-1-(3-(1-ethoxycarbonylmethyl-4-piperidyl)-phenyl)-benzimidazole (7g) from 8g. The product was purified on silica gel using ethyl acetate as the eluent and was isolated as the free base. Mp. 114.5–115° C.

5-(3-Furanyl)-1-(3-(4-ethoxycarbonylpiperid-1-ylmethyl)-phenyl)-benzimidazole (7h) from 8h. The product was purified on silica gel using a mixture of ethyl acetate and ethanol (9:1 v/v) as the eluent and was isolated as the free base.

5-(3-Furanyl)-1-(3-(4-ethoxycarbonyl-4-piperazinyl)-phenyl)-benzimidazole (7i) from 8i. The product was purified on silica gel using ethyl acetate as the eluent and isolated as the free base. Mp. 131–132° C.

2-(1-Acetyl-4-piperazinyl)-ethyl 3-(5-(3-furanyl)-1-benzimidazolyl)-benzoate (7j) from 8j. Mp. 167–168° C.

1-Methyl-2-pyrrolidylmethyl 3-(5-(3-furanyl)-1-benzimidazolyl)-benzoate (7k) from 8k. Mp. 198–200° C.

Example 8

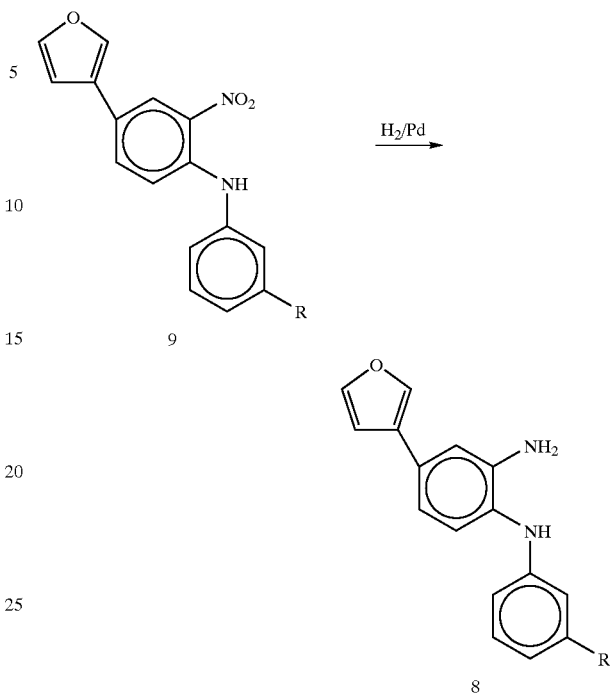

The furanyl substituted phenylenediamines of Table 6 were all prepared quantitatively by hydrogenation of the corresponding nitro compounds (9) as exemplified for compound 8a below.

TABLE 6

| Comp. No. | R | Starting material |
|---|---|---|
| 8a | —CH₂—N(piperazine)N—CO₂Et | 9a |
| 8b | —N(piperazine)N—CH₂—CO₂Et | 9b |
| 8c | N-methylimidazole-CO₂Me | 9c |

TABLE 6-continued

| Comp. No. | R | Starting material |
|---|---|---|
| 8d | -N(piperazine)N-CH2-CO2-tBu | 9d |
| 8e | methyl-dihydroisoxazole-CH2-C(O)-O-CH2-C(O)-N(Et)2 | 9e |
| 8f | Et-N(piperazine)N-CH2-CO2Et | 9f |
| 8g | Me-piperidine-N-CH2-CO2Et | 9g |
| 8h | Et-N-piperidine-CO2Et | 8h |
| 8i | Me-N(piperazine)N-CO2Et | 9i |
| 8j | CO2(CH2)2-N(piperazine)N-Ac | 9j |
| 8k | N-methyl-pyrrolidine-CH2-CO2- | 9k |

2-Amino-4-(3-furanyl)-N-(3-(1-ethoxycarbonyl-4-piperazinylmethyl)-phenyl)-aniline (8a). To a suspension of 9a (0.37 g; 0.82 mmol) in ethanol (10 ml) was added Pd-catalyst (5% Pd on activated carbon) and the mixture was hydrogenated until the hydrogen uptake had ceased. The mixture was filtered through celite and the solvent removed by evaporation to leave the desired product, quantitatively.

The following compound were prepared in analogy with Compound 8a:

2-Amino-4-(3-furanyl)-N-(3-(1-ethoxycarbonylmethyl-4-piperazinyl)-phenyl)-aniline. (8b) from 9b.

2-Amino-4-(3-furanyl)-N-(3-(4-methoxycarbonyl-1-imidazolyl)-phenyl)-aniline (8c) from 9c using methanol as the solvent.

2-Amino-4-(3-furanyl)-N-(3-(1-t-butoxycarbonyl-4-piperazinyl)-phenyl)-aniline (8d) from 9d using THF as the solvent.

N,N-Diethylcarbamoylmethyl 2-(3-(3-(2-amino-4-(3-furanyl)-phenylamino)-phenyl)-4,5-dihydroisoxazolin-5-yl)-acetate (8e) from 9e using THF as the solvent.

2-Amino-4-(3-furanyl)-N-(3-(1-ethoxycarbonylmethyl-4-piperazinylmethyl)-phenyl)-aniline (8f) from 9f.

2-Amino-4-(3-furanyl)-N-(3-(1-ethoxycarbonyl-4-piperidyl)-phenyl)-aniline (8g) from 9g.

2-Amino-4-(3-furanyl)-N-(3-(4-ethoxycarbonyl-1-piperidylmethyl)-phenyl)-aniline (8h) from 9h.

2-Amino-4-(3-furanyl)-N-(3-(4-ethoxycarbonyl-piperazinyl)-phenyl)-aniline (8i) from 9i.

2-(4-Acetyl-1-piperazinyl)ethyl 3-(N-(2-amino-4-(3-furanyl)-phenyl)-amino)-benzoate (8j) from 9j using THF as the solvent.

1-Methyl-2-pyrrolidylmethyl 3-(N-(2-amino-4-(3-furanyl)-phenyl)-amino)-benzoate (8k) from 9k using THF as the solvent.

Example 9

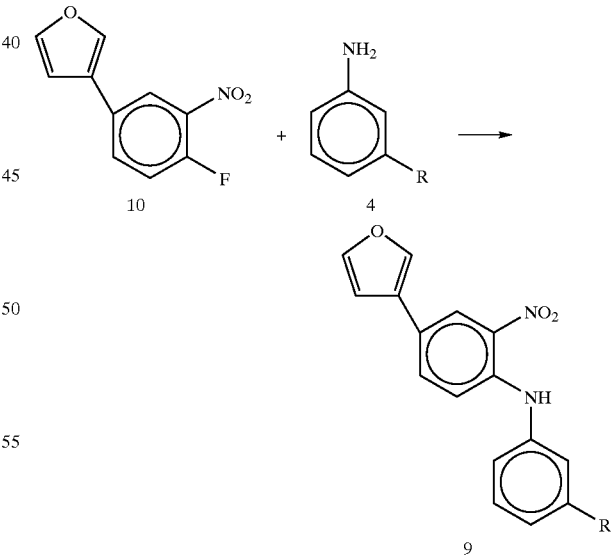

The furanyl substituted nitroanilines of Table 7 were all prepared by reaction of 10 (prepared as described in WO 96/33194) with substituted anilines (4 (see Example 4)) as described for compound 9a below.

TABLE 7

| Compound No. | R | Starting materials | Yield |
|---|---|---|---|
| 9a | ethyl-piperazine-CO₂Et | 10, 4a | 23 |
| 9b | methyl-piperazine-CH₂CO₂Et | 10, 4b | 10 |
| 9c | 1-methyl-imidazole-CO₂Me | 10, 4c | 10 |
| 9d | methyl-piperazine-CH₂CO₂tBu | 10, 4i | 61 |
| 9e | 3-methyl-isoxazoline-CH₂C(O)OCH₂C(O)N(Et)₂ | 10, 4k | 15 |
| 9f | ethyl-piperazine-CH₂CO₂Et | 10, 4m | 13 |
| 9g | 4-methyl-piperidine-CH₂CO₂Et | 10, 4n | 34 |
| 9h | 1-ethyl-piperidine-4-CO₂Et | 10, 4o | 38 |
| 9i | methyl-piperazine-CO₂Et | 10, 4p | 29 |
| 9j | CO₂(CH₂)₂-piperazine-NAc | 10, 4q | 51 |
| 9k | 1-methyl-pyrrolidine-CH₂CO₂- | 10, 4r | 34 |

2-Nitro-4-(3-furanyl)-N-(3-(1-ethoxycarbonyl-4-piperazinylmethyl)-phenyl)-aniline (9a). To a solution of 10 (0.75 g; 3.61 mmol) in NMP (5 ml) was added triethylamine (0.53 ml; 3.61 mmol) and 4a (1.0 g; 3.83 mmol). The mixture was heated to 110° C. for two days and then poured into water and extracted with ethyl acetate. The organic extract was washed with brine, dried over magnesium sulphate and concentrated under reduced pressure. The concentrate was purified by column-chromatography on silica gel using a mixture of ethyl acetate and petroleum ether (1:1 v/v) as the eluent. Yield: 23%.

The following compound were prepared in analogy with Compound 9a:

2-Nitro-4-(3-furanyl)-N-(3-(1-ethoxycarbonyl methyl-4-piperazinyl)-phenyl)-aniline (9b) from 10 and 4b.

2-Nitro-4-(3-furanyl)-N-(3-(4-methoxycarbonyl-1-imidazolyl)-phenyl)-aniline (9c) from 10 and 4c. Ethyl acetate was used as the eluent.

2-Nitro-4-(3-furanyl)-N-(3-(1-t-butoxycarbonyl-4-piperazinyl)-phenyl)-aniline (9d) from 10 and 4i.

N,N-Diethylcarbamoylmethyl 2-(3-(3-(N-(2-nitro-4-(3-furanyl)-phenyl)-amino)-phenyl)-4,5-dihydroisoxazolin-5-yl)-acetate (9e) from 10 and 4k. A mixture of ethyl acetate and petroleum ether (9:1 v/v) was used as the eluent.

2-Nitro-4-(3-furanyl)-N-(3-(1-ethoxycarbonylmethyl-4-piperazinylmethyl)-phenyl)-aniline (9F) from 10 and 4m.

2-Nitro-4-(3-furanyl)-N-(3-(1-ethoxycarbonyl-4-piperidyl)-phenyl)-aniline (9g) from 10 and 4n. Ethyl acetate was used as the eluent.

2-Nitro-4-(3-furanyl)-N-(3-(4-ethoxycarbonyl-1-piperidylmethyl)-phenyl)-aniline 9h from 10 and 4o.

2-Nitro-4-(3-furanyl)-N-(3-(4-ethoxycarbonyl-1-piperazinyl)-phenyl)-aniline (9i) from 10 and 4p.

2-(4-Acetyl-1-piperazinyl)ethyl 3-(N-(2-nitro-4-(3-furanyl)-phenyl)-amino)-benzoate (9j) from 10 and 4q. Ethyl acetate was used as the eluent.

1-Methyl-2-pyrrolidylmethyl 3-(N-(2-nitro-4-(3-furanyl)-phenyl)-amino)-benzoate (9k) from 10 and 4r. A mixture of dichloromethane, methanol and aqueous ammonia (90:10;1) was used as the eluent.

Example 10

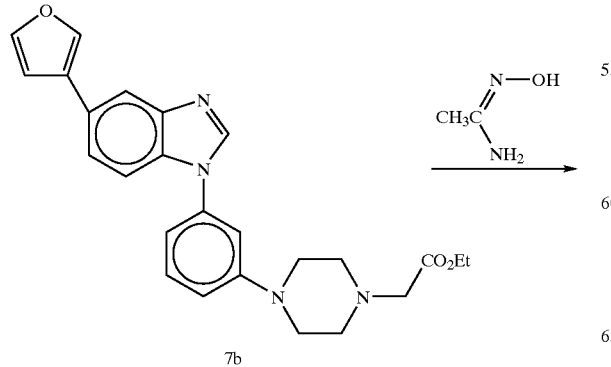

7b

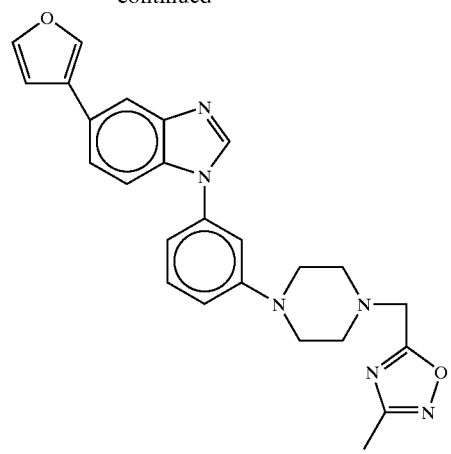

11

5-(3-Furanyl)-1-(3-(1-(3-methyl-5-oxadiazolylmethyl)-4-piperazine)-phenyl)-benzimidazole (11). To a solution of sodium (0.12 g; 5.2 mmol) in abs. ethanol (10 ml) was added molecular sieves (0.5 g), acetamide-oxime (0.19 g; 2.57 mmol) and 7b (1.0 g; 2.32 mmol). The mixture was heated to reflux overnight. The cooled suspension was diluted with dichloromethane (50 ml) and stirred until all organic material had dissolved. The molecular sieves were filtered off and the filtrate was washed with water and brine, dried over sodium sulphate and evaporated to dryness. The residue was dissolved in toluene and a catalytic amount of p-toluenesulfonic acid was added. The mixture was heated to 100° C. overnight, whereafter the cooled mixture was washed with aqueous sodium carbonate, dried over sodium sulphate and evaporated to dryness. The residue was triturated with diethyl ether to yield 11 (0.47 g; 46%). Mp. 129–130° C.

Example 11

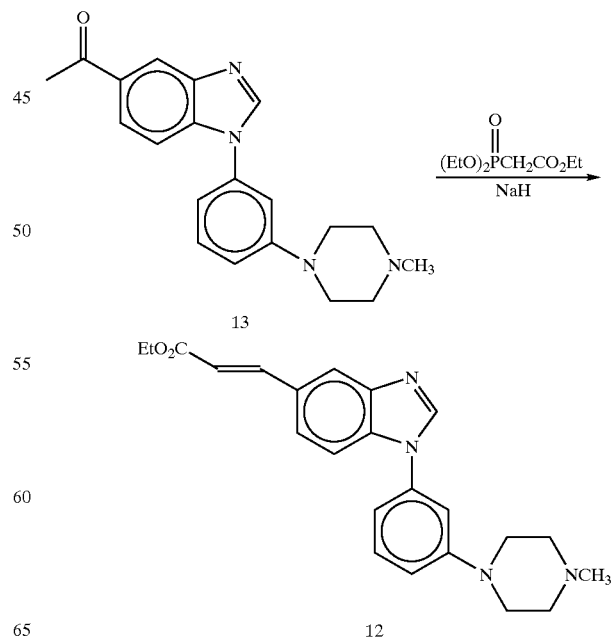

Ethyl (E)-3-(1-(3-(4-methyl-1-piperazinyl)-phenyl)-benzimidazol-5-yl)-Propenoate (12). To a suspension of sodium hydride (40 mg, 60% dispersion in mineral oil, 1.0 mmol) kept in an inert atmosphere was added triethylphosphone-acetate (0.2 ml; 1.0 mmol). The mixture was stirred at ambient temperature until a clear solution had formed. A solution 13 (0.33 g; 0.94 mmol) in anhydrous toluene (5 ml) was added. Stirring was continued for 15 min at room temperature whereafter the temperature was raised to 60–65° C. overnight. The solvents were removed under reduced pressure and the residue was partitioned between ethyl acetate and water. The phases were separated and the aqueous phase was extracted thrice with ethyl acetate. The combined organic extracts were dried over magnesium sulphate and concentrated. The concentrate was purified by column-chromatography on silica gel using a mixture of dichloromethane, methanol and aqueous ammonia (90:10:1 v/v/v) as the eluent. The product-containing fractions were evaporated to dryness, re-dissolved in abs. ethanol and precipitated as the hydrochloride by addition of ethereal hydrogen chloride. Yield: 0.28 g (68%). Mp. 180–190° C. (with decomposition).

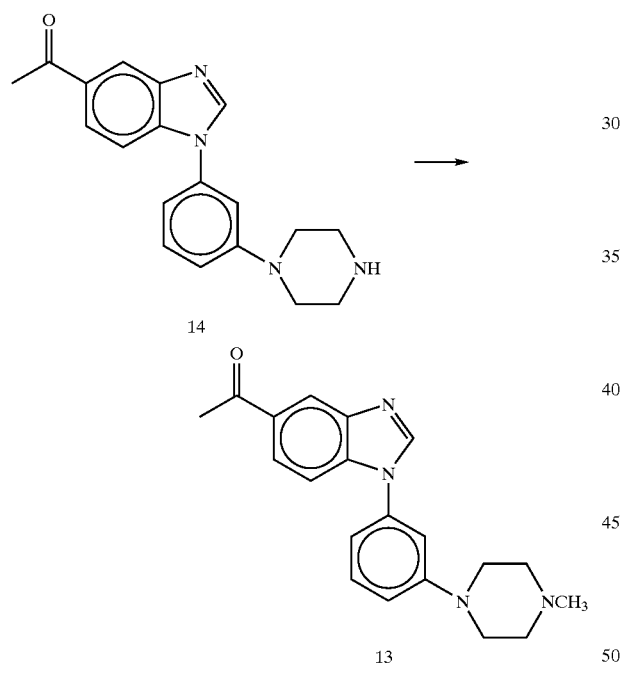

5-Acetyl-1-(3-(4-methyl-1-piperazinyl)-phenyl)-benzimidazole (13). To a solution of 14 (0.75 g; 2.34 mmol) in anhydrous DMF (10 ml) was added sodium hydride (0.1 g, 60% dispersion in mineral oil). The mixture was stirred for 30 min and iodo-methane (0.15 ml; 2.34 mmol) was added. After one hour the mixture was poured into ice-water and extracted with ethyl acetate. The extract was dried over magnesium sulphate and concentrated under reduced pressure. The concentrate was purified by column-chromatography using mixtures of ethyl acetate and methanol (9:1 v/v, 1:1 v/v), successively as eluents. Yield: 0.34 g (41%).

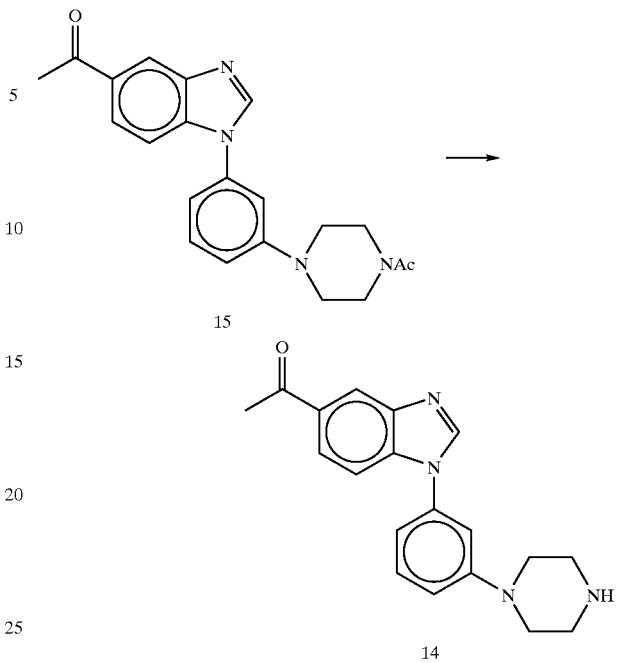

5-Acetyl-1-(3-(1-piperazinyl)-phenyl)-benzimidazole (14). To a solution of 15 (8.3 g; 23.0 mmol) in dimethoxyethane (140 ml) was added aqueous sodium hydroxide (70 ml; 1 M) and the mixture was heated to reflux overnight. The volatile solvent was removed and the aqueous suspension was extracted with dichloromethane. This extract was dried over sodium sulphate, concentrated and eluted through a silica gel column with a mixture of dichloromethane, methanol and aqueous ammonia (90:10:1 v/v/v). Yield: 4.8 g (65%).

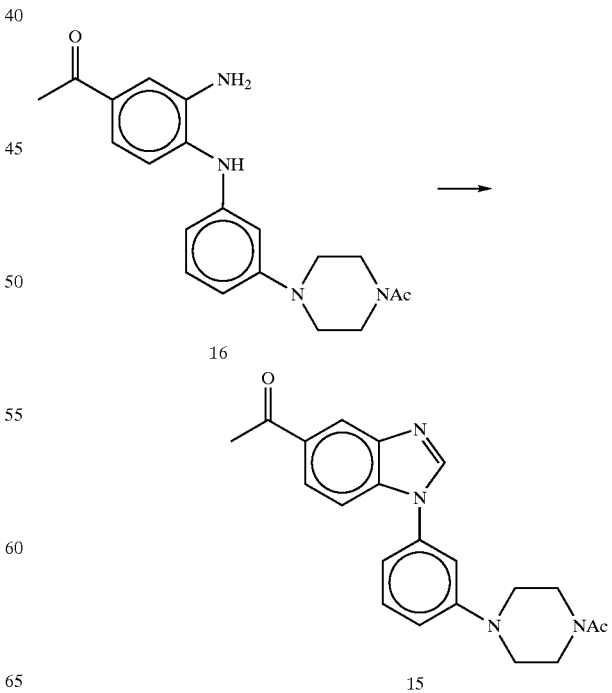

5-Acetyl-1-(3-(1-acetyl-4-piperazinyl)-phenyl)-benzimidazole (15). 16 (17.7 g; 50.3 mmol) was treated with triethyl orthoformiate as described in Example 1. The product was purified by column-chromatography on silica gel using a mixture of dichloromethane, methanol and aqueous ammonia (90:10:1 v/v/v) as the eluent.

Yield: 16.0 g (88%).

2-(3,5-dimethyl-1-Diperazinyl)ethyl 3-(5-acetylbenzimidazol-1-yl)-benzoate was prepared analogously to 15. The compound was treated hydroxylamine hydrochloride in abs. ethanol to yield 2-(3,5-dimethyl-1-piperazinyl)ethyl 3-(5-acetylbenzimidazol-1-yl)-benzoate oxime (15a) Mp. 255–260° C.

2-(2-pyridyl)methyl 3-(5-acetylbenzimidazol-1-yl)-benzoate was prepared analogously to 15. This compound was treated hydroxylamine hydrochloride in abs. ethanol to yield 2-(2-pyridyl)-methyl 3-(5-acetylbenzimidazol-1-yl)-benzoate oxime (15b) Mp. 162–163° C.

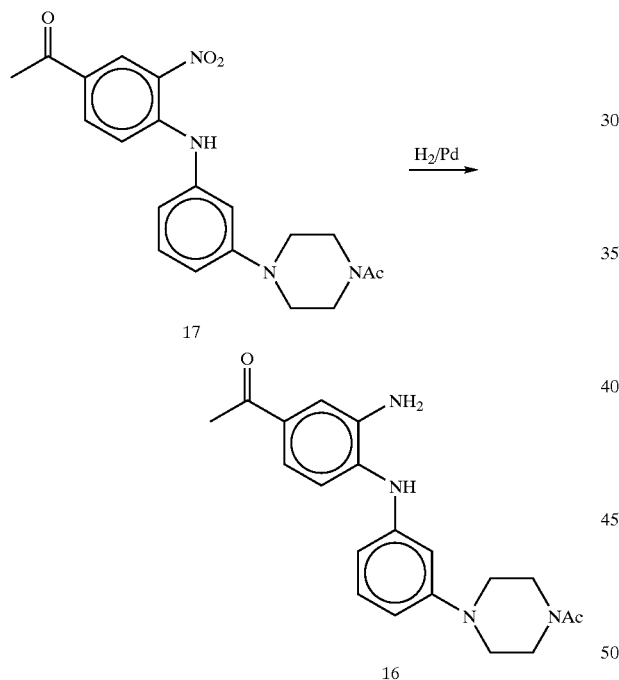

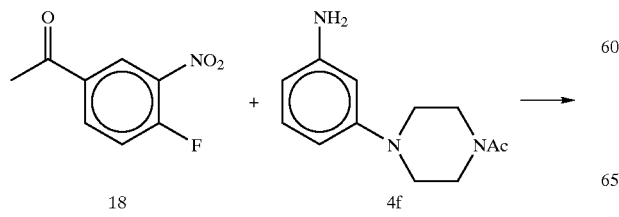

N-(4-Acetyl-2-aminophenyl)-3-(1-acetyl-4-piperazinyl)-aniline (16). 17 (45 g; 93.6 mmol) was hydrogenated as described in Example 2 to yield 16, quantitatively.

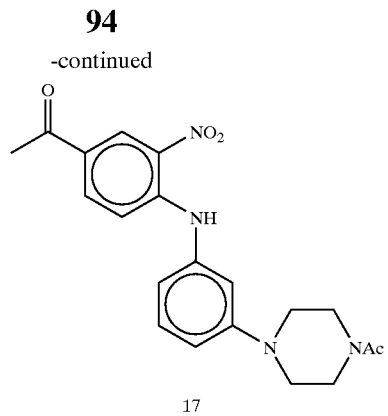

N-(4-Acetyl-2-nitrophenyl)-3-(1-acetyl-4-piperazinyl)-aniline (17). To a solution of 18 (17.1 g; 93.6 mmol) (prepared as previously described: WO 96/33191) and triethylamine (13 ml; 93.6 mmol) in anhydrous NMP (50 ml) was added 4f and the mixture was heated to 80° C. for four hours. The cooled mixture was poured into ice-water and extracted thrice with ethyl acetate. The organic extract was dried over sodium sulphate and evaporated to dryness to leave 17, quantitatively.

Example 12

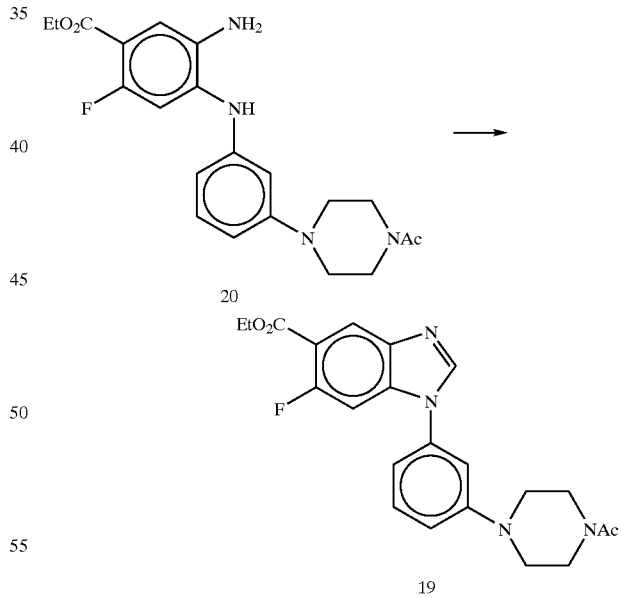

Ethyl 1-(3-(4-acetyl-1-piperazinyl)-phenyl)-6-fluorobenzimidazole-5-carboxylate (19) was prepared analogously to Example 1 from 20. A mixture of ethyl acetate and ethanol (9:1 v/v) was used as the eluent. Yield: 55%. Mp. undefined.

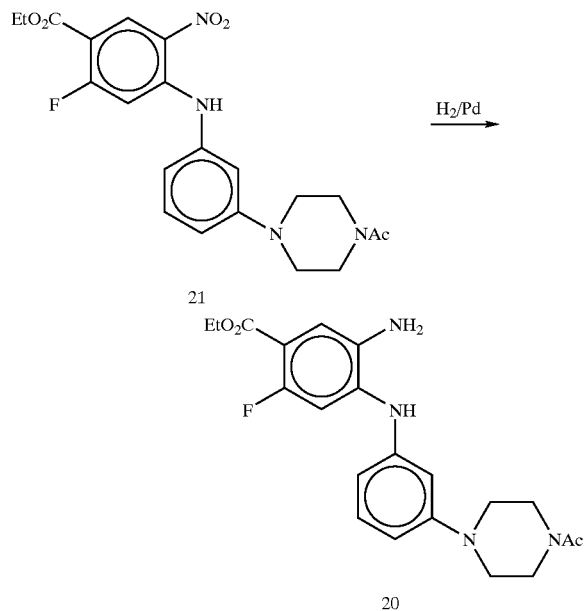

Ethyl 3-amino-4-(3-(4-acetyl-1-piperazinyl)-phenyl)-amino-6-fluorobenzoate (20) was prepared from 21 in analogy with Example 2. Abs. ethanol was used as solvent. Quantitative yield.

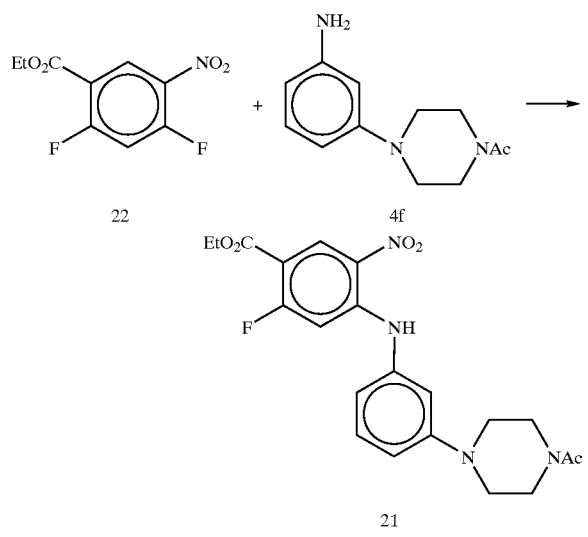

Ethyl 4-(3-(4-acetyl-1-piperazinyl)-phenyl)-amino-6-fluoro-3-nitrobenzoate (21). A mixture of ethyl 2,4-difluoro-5-nitrobenzoate (22) (1.0 g; 4.33 mmol), 4f (0.95 g; 4.33 mmol) and triethylamine (0.6 ml; 0.33 mmol) in anhydrous NMP (10 ml) was heated to 80° C. for one hour. The cooled mixture was poured into water and extracted with ethyl acetate. The organic extract was dried over magnesium sulphate, concentrated under reduced pressure and purified by column-chromatography on silica gel using ethyl acetate as the eluent. Yield: 1.53 g (82%).

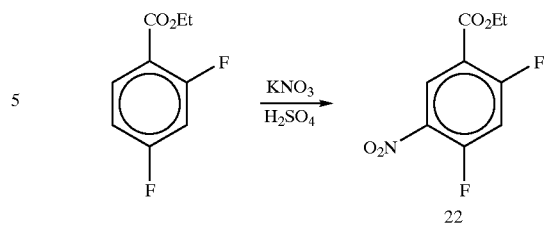

Ethyl 2,4-difluoro-5-nitrobenzoate (22). To a cooled (−5–0° C.) solution of ethyl 2,4-difluorobenzoate (3.4 g; 18.3 mmol) in conc. sulphuric acid (6 ml) was added potassium nitrate (1.94 g; 19.2 mmol) in small portions over one hour −5° C. Following the addition the temperature was allowed to raise to 20° C. over 4.5 hours. The mixture was poured into ice-water with vigorous stirring. The product was filtered off, washed with water and air-dried. Yield: 3.2 g (76%).

Example 13
In Vitro and In Vivo Binding Activity

The GABA recognition site and the benzodiazepine modulatory unit can selectively be labelled with $^3$H-muscimol and $^3$H-flunitrazepam, respectively.

13A: In Vitro Inhibition of $^3$H-flunitrazepam (3H-FNM) Binding

Tissue Preparation

Preparations are performed at 0–4° C. unless otherwise indicated. Cerebral cortex from male Wistar rats (150–200 g) is homogenised for 5–10 sec in 20 ml Tris-HCl (30 mM, pH 7.4) using an Ultra-Turrax homogeniser. The suspension is centrifuged at 27,000×g for 15 min and the pellet is washed three times with buffer (centrifuged at 27,000×g for 10 min). The washed pellet is homogenized in 20 ml of buffer and incubated on a water bath (37° C.) for 30 min to remove endogenous GABA and then centrifuged for 10 min at 27,000×g. The pellet is then homogenized in buffer and centrifuged for 10 min at 27,000×g. The final pellet is resuspended in 30 ml buffer and the preparation is frozen and stored at −20° C.

Assay

The membrane preparation is thawed and centrifuged at 2° C. for 10 min at 27,000×g. The pellet is washed twice with 20 ml 50 mM Tris-citrate, pH 7.1 using an Ultra-Turrax homogeniser and centrifuged for 10 min at 27,000×g. The final pellet is resuspended in 50 mM Tris-citrate, pH 7.1 (500 ml buffer per g of original tissue), and then used for binding assays. Aliquots of 0.5 ml tissue are added to 25 μl of test solution and 25 μl of $^3$H-FNM (1 nM, final concentration), mixed and incubated for 40 min at 2° C. Non-specific binding is determined using Clonazepam (1 μM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

Results

25–75% inhibition of specific binding must be obtained, before calculation of an $IC_{50}$.

The test value will be given as $IC_{50}$ (the concentration (μM) of the test substance which inhibits the specific binding of $^3$H-FNM by 50%).

$$IC_{50} = \text{(applied test substance concentration, μM)} \times \frac{1}{\left(\frac{C_o}{C_x} - 1\right)}$$

where
  $C_o$ is specific binding in control assays, and
  $C_x$ is the specific binding in the test assay.
  (The calculations assume normal mass-action kinetics).
The results from these experiments are shown in Table 8 below.

13B: In Vivo Inhibition of $^3$H-FNM Binding

Introduction

In vitro binding studies have demonstrated that the benzodiazepine [$^3$H]FNM binds selectively and with high-affinity to the GABA$_A$ receptor-ion channel complex. [$^3$H]FNM can also be used for in vivo receptor labelling studies in mouse. Accumulation of [$^3$H]FNM binding will occur all over the brain as GABA$_A$ receptors are widely distributed. The specific binding of [$^3$H]FNM can be partly or completely prevented by simultaneous or prior administration of pharmacologically active benzodiazepines or by some benzodiazepine-like compounds.

Method

All test substances used are solutions prepared in 10% TWEEN 80. Groups of three female NMRI mice (25 g) are injected i.v. via the tail vein with 5.0 μCi of [$^3$H]FNM in 0.2 ml saline. Fifteen min after injection with [$^3$H]FNM the test substance is administered i.v. Twenty min after injection with [$^3$H]FNM, mice are killed by decapitation, the forebrains rapidly excised and homogenized in 12 ml of ice-cold 50 mM Tris-citrate, pH 7.1 using an Ultra-Turrax homogenizer. Three aliquots of 1 ml are immediately filtered through GF/C glass fibre filters and washed with 2×5 ml of ice-cold buffer. The amounts of radioactivity on the filters and in 200 μl of the homogenate are determined by conventional scintillation counting. Groups of untreated mice serves as controls. To determine non-specific binding groups of mice are injected with Clonazepam (25 mg/kg) i.p. 10 min before [$^3$H]FNM injection. Specific binding is the amount of binding in controls minus the amount of binding in Clonazepam treated mice.

Results

The ED$_{50}$ value is determined from dose response curves. If only one dose of test substance is administered, the ED$_{50}$ value is calculated as follows, provided that the inhibition of specific binding is within the range of 25–75%.

$$ED_{50} = \text{(administered dose, mg/kg)} \times \frac{1}{\left(\frac{C_o}{C_x} - 1\right)}$$

where $C_o$ is specific binding in controls and $C_x$ is the specific binding in mice treated with test substance.

The results from these experiments are shown in Table 8 below.

TABLE 8

| Test compound | In vitro binding IC$_{50}$ (μM) | In vivo binding ED$_{50}$ (mg/kg) |
| --- | --- | --- |
| Of the invention: | | |
| 1b | 0.26 | 0.9 |
| 7j | 0.0028 | 1.9 |

TABLE 8-continued

| Test compound | In vitro binding IC$_{50}$ (μM) | In vivo binding ED$_{50}$ (mg/kg) |
| --- | --- | --- |
| 7i | 0.0008 | 1.8 |
| 7g | 0.0009 | 1.4 |
| 7c | 0.0007 | 0.43 |
| 11 | 0.012 | 0.75 |
| 7f | 0.0006 | 0.17 |
| Reference compounds: | | |
| Compound 4d$_3$ of WO 98/17651 | 0.06 | 0.22 |
| Compound 4j of WO 98/17651 | 1.1 | 13.3 |
| Compound 4m of WO 98/17651 | 1.0 | 6 |

Example 14

PTZ Clonic Convulsions

The purpose of this test is to show antagonism of clonic convulsions induced by pentylenetetrazol (PTZ). PTZ induces clonic convulsions in mice after i.v. infusion. Antagonism of PTZ-induced convulsions is a measure for the agonistic character of ligands for the benzodiazepine recognition site.

Procedure

Female NMRI mice (Bomholdtgaard, Ry), 20 g, 6 mice in each group are administered i.v. with vehicle or test substance. After five minutes the PTZ-solution is infused intravenously at a speed of 0.7 ml/minute through a cannula placed in the tail vein. The time from initiation of the infusion to appearance of clonic convulsions is recorded.

The dose of PTZ required for inducing convulsion in each mouse is calculated as PTZ/kg body weight. Means ±sd for each experimental group of 6 mice is calculated. ED$_{100}$ is calculated by linear regression expressing the dose increasing the PTZ threshold to 100 mg PTZ/kg.

The threshold of vehicle treated controls is in the range of 37–39 mg PTZ/kg. As a control in each series of experiments PTZ is infused into 6 vehicle treated mice.

The results from these experiments are shown in Table 9 below.

TABLE 9

| Test compound | ED$_{100}$ (mg/kg) | ptz threshold at 30 mg/kg (mg/kg) |
| --- | --- | --- |
| Of the invention: | | |
| 1b | 1.6 | 200 |
| 7j | 13 | 170 |
| 7i | 2.5 | 140 |
| 7g | 1.2 | 200 |
| 7c | 20 | 110 |
| 11 | 17 | 120 |
| 7f | 2.7 | 120 |
| Reference compounds: | | |
| Compound 4d$_3$ of WO 98/17651 | 0.16 | 230 |
| Compound 4j of WO 98/17651 | 16 | 140 |
| Compound 4m of WO 98/17651 | 9 | 175 |

Example 15

Evaluation of Efficacy

Selected compounds exhibiting a promising profile in the above tests were evaluated with respect to efficacy and duration of action and compared to prior art as follows.

Aqueous solutions of the test substances (50 mg/ml isotonic glucose) were administered to pigs (25–30 kg) as bolus injections. The actual dose of each substance is included in the table below. The pigs were observed with respect to the time of induction of anaesthesia, the duration of anaesthesia and the normalising time following awakening from anaesthesia.

These observations are compiled in Table 10 below. This table also provides comparative data for compounds of the prior art (WO 98/17651).

TABLE 10

| Compound No. | Bolus dose (mg/kg) | Induction Time (min.) | Maintained anaesthesia (min.) | Normalising time following awakening (min.) |
|---|---|---|---|---|
| 7j | 3 | 0.5 | 8[a] | 20 |
| 1b | 0.6 | 1.3 | 10 | 15 |
| Compound 4d$_3$ of WO 98/17651 | 0.03 | 0.75 | 60 | 120 |
| Compound 4j of WO 98/17651 | 3 | 1.0 | 0[b] | — |
| Compound 4m of WO 98/17651 | 3 | — | 0[c] | — |

[a]Uneasy sleep
[b]light sleep/sedation
[c]only mild sedation observed

From the table it can be concluded, that the compounds of the present invention has a very advantageous profile regarding the induction time, duration of action and recovery time. Compared to the compounds of prior art, which shows either a too weak anaesthesising effect or a too long recovery time, the compounds provided by the present invention meet the criteria for promising anaesthetics.

What is claimed is:

1. A benzimidazole derivative represented by the general Formula I,

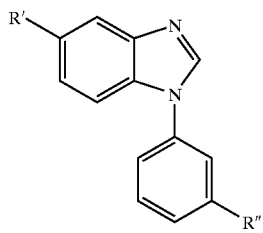

(I)

or a pharmaceutically acceptable salt thereof, wherein,
R' represents a group of the formula -(alk)$_q$-R$^1$, wherein (alk) represents alkyl, alkenyl or alkynyl, q is 0 or 1, R$^1$ represents a group of the formula —CO$_2$R$^2$, wherein R$^2$ represents hydrogen, alkyl, hydroxy-alkyl, alkoxy-alkyl, thioalkoxy-alkyl, alkyl-"Heterocycle", or -alkyl-NR$^3$R$^4$, wherein "Heterocycle" represents a mono- or polycyclic heterocyclic group, which heterocyclic group is optionally substituted one or more times with substituents selected from the group consisting of halogen, alkyl, hydroxy, oxo, cyano, hydroxy-alkyl, alkoxy-alkyl, carboxyl and acyl, and a group of the formula -(alkyl)$_p$-CN, -(alkyl)$_p$-aryl, -(alkyl)$_p$-"Heterocycle", -(alkyl)$_p$-CO$_2$-"Heterocycle" or -(alkyl-CO$_2$)$_s$-(alkyl)$_t$-COR$^5$, in which formulas p, s and t independently of each another is 0 or 1, "Heterocycle" represents a mono- or polycyclic heterocyclic group, which heterocyclic group is optionally substituted one or more times with substituents selected from the group consisting of halogen, alkyl, hydroxy, oxo, cyano, hydroxy-alkyl, alkoxy-alkyl, carboxyl and acyl, R$^5$ represents hydroxy, alkoxy, hydroxy-alkoxy, alkoxy-alkoxy, thioalkoxy-alkoxy, or a group of the formula —NR$^6$R$^7$ or —O-alkyl-NR$^6$R$^7$, in which formulas R$^6$ and R$^7$ independently of each another represent hydrogen, alkyl, cycloalkyl or a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl, or R$^6$ and R$^7$ together with the nitrogen to which they are attached form a mono- or polycyclic heterocyclic group, which heterocyclic group may be substituted one or more times with substituents selected from the group consisting of halogen, alkyl, hydroxy, oxo, hydroxy-alkyl, alkoxy-alkyl, carboxyl and acyl; and R$^3$ and R$^4$ independently of each another represent hydrogen, alkyl or cycloalkyl, or R$^3$ and R$^4$ together with the nitrogen to which they are attached form a mono- or poly-cyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl;
R" represents -(alkyl)$_o$-"Heterocycle" wherein o is 1 and "Heterocycle" represents a monocyclic heterocyclic group selected from a thienyl group, a pyrrolyl group, an imidazolyl group, an oxazolyl group, and isoxazolyl group, an oxadiazolyl group, a pyridinyl group, or a tetrazolyl group, which heterocyclic group is optionally substituted one or more times with substituents selected from the group consisting of halogen, alkyl, hydroxy, oxo, cyano, hydroxy-alkyl, alkoxy-alkyl, carboxyl, and acyl, and a group of the formula -(alkyl)$_p$-CN, -(alkyl)$_p$-aryl, -(alkyl)$_p$-aralkyl, -(alkyl)$_p$-O-aryl, -(alkyl)$_p$-O-aralky, -(alkyl)$_p$-CO$_2$-aryl, -(alkyl)$_p$-CO$_2$-aralkyl, -(alkyl)$_p$-"Heterocycle", -(alkyl)$_p$-CO$_2$-"Heterocycle" or -(alkyl-CO$_2$)$_s$-(alkyl)$_t$-COR$^5$, in which formulas p, s and t independently of each another is 0 or 1, "Heterocycle" represents a mono- or polycyclic heterocyclic group, which heterocyclic group is optionally substituted one or more times with substituents selected from the group consisting of halogen, alkyl, hydroxy, oxo, cyano, hydroxy-alkyl, alkoxy-alkyl, carboxyl and acyl, R$^5$ represents hydrogen, hydroxy, alkyl, alkoxy, hydroxy-alkyl, hydroxy-alkoxy, alkoxy-alkyl, alkoxy-alkoxy, thioalkoxy-alkyl, thioalkoxy-alkoxy, or a group of the formula —NR$^6$R$^7$ or —O-alkyl-NR$^6$R$^7$, in which formulas R$^6$ and R$^7$ independently of each another represent hydrogen, alkyl, cycloalkyl or a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl, or R$^6$ and R$^7$ together with the nitrogen to which they are attached form a mono- or polycyclic heterocyclic group, which heterocyclic group is optionally substituted one or more times with substituents selected from the group consisting of halogen, alkyl, hydroxy, oxo, hydroxy-alkyl, alkoxy-alkyl, carboxyl and acyl.

2. The benzimidazole derivative of claim 1, wherein R$^1$ represents a group of the formula —CO$_2$R$^2$, wherein R$^2$ represents alkyl, hydroxy-alkyl, alkoxy-alkyl, thioalkoxy-alkyl, or alkyl-N (alkyl)$_2$.

3. The benzimidazole derivative of claim 2, wherein $R^1$ represents a group of the formula —COOH, —CO$_2$—CH$_3$, —CO$_2$—C$_2$H$_5$, —CO$_2$—CH$_2$—CH(OH), —CO$_2$(CH$_2$)$_2$OCH$_3$, —CO$_2$(CH$_2$)$_2$SCH$_3$, —CO$_2$(CH$_2$)$_2$SC$_2$H$_5$, or —CO$_2$(CH$_2$)$_2$N(CH$_3$).

4. The benzimidazole derivative of either of claims 2–3, wherein R" represents a group of the formula -(alkyl)$_o$-"Heterocycle", wherein o is 1, and "Heterocycle" represents a furanyl group, a thienyl group, a pyrrolyl group, an imidazolyl group, an oxazolyl group, an isoxazolyl group, an oxadiazolyl group, a pyridinyl group, or a tetrazolyl group, which heterocyclic groups may be substituted one or more times with substituents selected from the group consisting of halogen, alkyl, oxo, acyl, alkyl-CO$_2$H, alkyl-CO$_2$-alkyl -(alkyl)$_p$-CO$_2$-aryl, -(alkyl)$_p$-CO$_2$-aralkyl and alkyl-CO$_2$-alkyl-CONR$^6$R$^7$, wherein R$^6$ and R$^7$ independently of each another represent hydrogen or alkyl.

5. The benzimidazole derivative of claim 4, wherein "Heterocycle" represents an imidazol-1-yl; a pyridin-4-yl; or a piperidin-4-yl group.

6. The benzimidazole derivative of claim 5, wherein R" represents 1-imidazolylmethyl.

7. The benziznidazole derivative of claim 6, which is
Methyl 1-(3-(1-imidazolylmethyl)-phenyl)-benzimidazole-5-carboxylate;

2-(Methylthio)-ethyl 1-(3-(1-imidazolylmethyl)-phenyl)-benzimidazole-5-carboxylate;

or a pharmaceutically acceptable salt thereof.

8. A pharmaceutical composition containing a therapeutically effective amount of a benzimidazole derivative according to claim 1, or a pharmaceutically acceptable addition salt thereof, together with at least one pharmaceutically acceptable carrier, excipient or diluent.

9. A method for treatment or alleviation of fever cramps or status epilepticus of a living animal body, including a human, wherein said fever cramps or status epilepticus is responsive to modulation of the GABA receptor complex, which method comprises the step of administering to such a living animal body in need thereof a therapeutically effective amount of a benzimidazole derivative according to claim 1.

10. A method for the induction or maintenance of anaesthesia or pre-anaesthesia in a living animal body, including a human, which method comprises the step of administering to such a living animal an amount of a benzimidazole derivative according to claim 1 effective to induce or maintain anaesthesia or pre-anaesthesia.

* * * * *